US010093929B2

(12) United States Patent
Liang

(10) Patent No.: US 10,093,929 B2
(45) Date of Patent: Oct. 9, 2018

(54) MODULAR RNA REGULATORS AND METHODS

(71) Applicant: STC.UNM, Albuquerque, NM (US)

(72) Inventor: Fu-Sen Liang, Albuquerque, NM (US)

( * ) Notice: Subject to any disclaimer, the term of this patent is extended or adjusted under 35 U.S.C. 154(b) by 19 days.

(21) Appl. No.: 15/029,307

(22) PCT Filed: Oct. 10, 2014

(86) PCT No.: PCT/US2014/060052
§ 371 (c)(1),
(2) Date: Apr. 14, 2016

(87) PCT Pub. No.: WO2015/057511
PCT Pub. Date: Apr. 23, 2015

(65) Prior Publication Data
US 2016/0237439 A1    Aug. 18, 2016

Related U.S. Application Data

(60) Provisional application No. 61/890,552, filed on Oct. 14, 2013, provisional application No. 61/971,142, filed on Mar. 27, 2014.

(51) Int. Cl.
*C07H 21/04* (2006.01)
*C07H 21/02* (2006.01)
*C12N 15/113* (2010.01)
*C12N 15/11* (2006.01)

(52) U.S. Cl.
CPC ........ *C12N 15/1137* (2013.01); *C12N 15/111* (2013.01); *C12N 2310/141* (2013.01); *C12N 2310/315* (2013.01); *C12N 2310/3181* (2013.01); *C12N 2310/3231* (2013.01); *C12N 2310/3233* (2013.01); *C12N 2320/50* (2013.01); *C12Y 301/00* (2013.01)

(58) Field of Classification Search
CPC .............................. C12N 15/113; A61K 48/00
See application file for complete search history.

(56) References Cited

U.S. PATENT DOCUMENTS

| 2008/0199961 A1 | 8/2008 | Rasko et al. | |
| 2009/0092980 A1 | 4/2009 | Arenz et al. | |
| 2011/0178281 A1* | 7/2011 | Chen et al. | ........ C12N 2310/11 |

FOREIGN PATENT DOCUMENTS

| WO | WO 2005/023986 A2 * | 3/2005 | ........... C12N 15/113 |

OTHER PUBLICATIONS

Ardekani et al., "The Role of MicroRNAs in Human Diseases" 2010 *Avicenna Journal of Medical Biotechnology*, 2(4):161-179.
Ashley et al., "The targeted delivery of multicomponent cargos to cancer cells by nanoporous particle-supported lipid bilayers" May 2011 *Nature Materials*, 10:389-397.
Callaway et al., "Photostimulation using caged glutamate reveals functional circuitry in living brain slices" Aug. 1993 *Proc. Natl. Acad. Sci.*, 90:7661-7665.
Choi et al., "A photochemical approach for controlled drug release in targeted drug delivery" Feb. 2012 *Bioorganic & Medicinal Chemistry*, 20(3):1281-1290.
Diver et al., "Single-Step Synthesis of Cell-Permeable Protein Dimerizers That Activate Signal Transduction and Gene Expression" Jun. 1997 *Journal of the American Chemical Society*, 119(22):5106-5109.
Guo et al., "Facile functionalization of FK506 for biological studies by the thiol—ene 'click' reaction" 2014 *Royal Society of Chemistry*, 4:11400-11403.
He et al., "MicroRNAs: small RNAs with a big role in gene regulation" Jul. 2004 *Nature Reviews Genetics*, 5:522-531.
Kolb et al., "Click Chemistry: Diverse Chemical Function from a Few Good Reactions" 2001 *Angew. Chem. Int. Ed.*, 40:2004-2021.
Lee et al., "Differential roles of human Dicer-binding proteins TRBP and PACT in small RNA processing" May 2013 *Nucleic Acids Research*, 41(13):6568-6576.
Liang et al., "Engineering the ABA Plant Stress Pathway for Regulation of Induced Proximity" Mar. 2011 *Science Signaling*, 4(164): 18 pgs.
Macrae et al., "Structural Basis for Double-Stranded RNA Processing by Dicer" Jan. 2006 *Science*, 311(5758):195-198.
Ouyang et al., "Versatile Synthesis and Rational Design of Caged Morpholinos" 2009 *Journal of the American Chemical Society*, 131(37): 13255-13269.
Parkes et al., "Use of a Pharmacophore Model to Discover a New Class of Influenza Endonuclease Inhibitors" Feb. 2003 *Journal of Medicinal Chemistry*, 46(7):1153-1164.
Ponia et al., "Arginine rich short linear motif of HIV-1 regulatory proteins inhibits Dicer dependent RNA interference" Sep. 2013 *Retrovirology*, 10(97): 17 pgs.
Sharma et al., "Glucose-based amphiphilic telomers designed to keep membrane proteins soluble in aqueous solutions: synthesis and physicochemical characterization" 2008 *Langmuir*, 24(23): 13581-13590.
Shembekar et al., "A Protecting Group for Carboxylic Acids That Can Be Photolyzed by Visible Light" 2005 *Biochemistry*, 44:7107-7114.
Van Rooij et al., "Developing MicroRNA Therapeutics" Feb. 2012 *Circulation Research*, 110(3):496-507.

(Continued)

*Primary Examiner* — Amy H Bowman
(74) *Attorney, Agent, or Firm* — Mueting, Raasch & Gebhardt, P.A.

(57) ABSTRACT

This disclosure describes modular miRNA regulator molecules and methods of using modular miRNA regulator molecules. Generally, the modular miRNA regulator molecules include a recognition module and an inhibition module. Generally, the recognition module includes a polynucleotide in which at least a portion of the polynucleotide recognizes at least a portion of a preselected pre-miRNA. Generally, the inhibition module includes a moiety that inhibits nuclease processing of the preselected pre-RNA to a mature RNA.

15 Claims, 55 Drawing Sheets

Specification includes a Sequence Listing.

(56) References Cited

OTHER PUBLICATIONS

Wu, Terry, "Formulation of Stable Dry Powder Live Vaccines by Spray Drying *Listeria monocytogenes*," Grant Abstract, Grant No. #HDTRA-1-12-C-0046. *Defense Threat Reduction Agency*.

PCT Patent Application No. PCT/US2014/060052, filed Oct. 10, 2014; International Search Report and Written Opinion dated Jan. 14, 2015; 15 pages.

PCT Patent Application No. PCT/US2014/060052, filed Oct. 10, 2014; International Preliminary Report on Patentability dated Apr. 28, 2016; 11 pages.

* cited by examiner

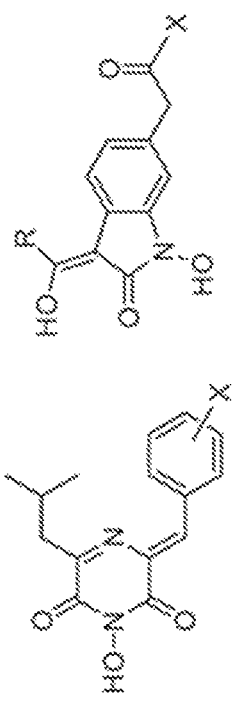
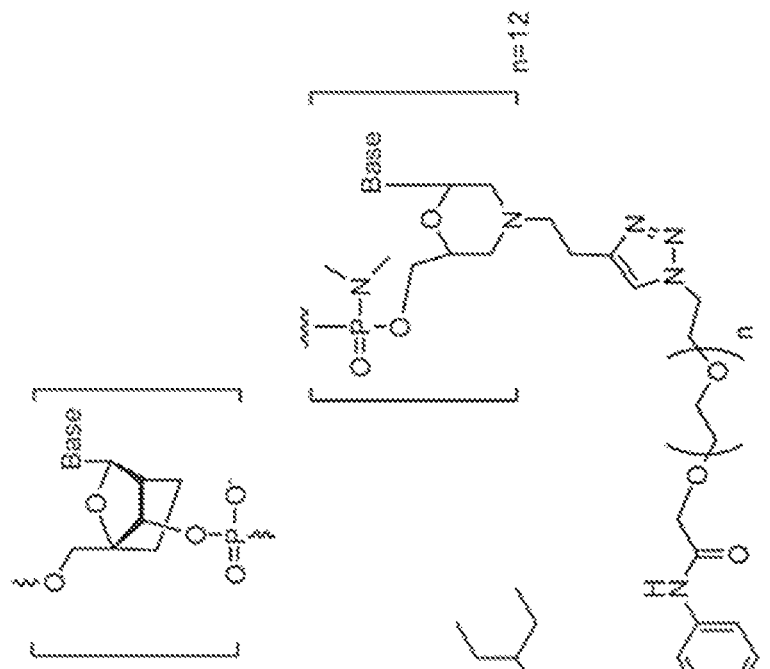
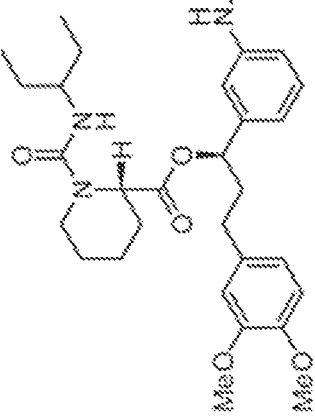
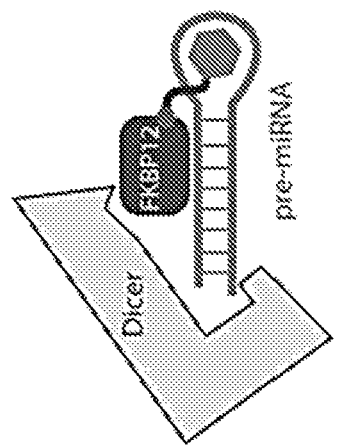
FIG. 4A
FIG. 4B
FIG. 4C
FIG. 4D

FIG. 30A
FIG. 30B
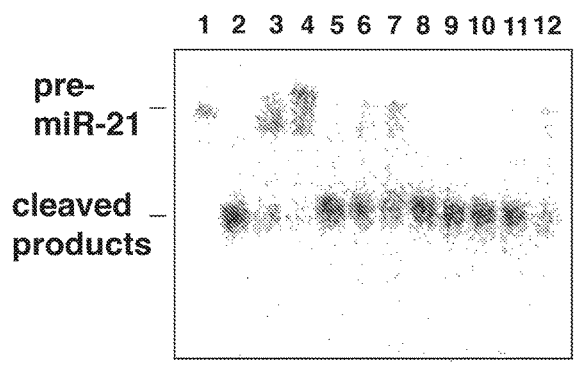
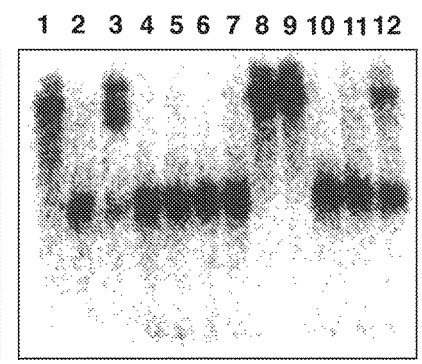

MODULAR RNA REGULATORS AND METHODS

CROSS-REFERENCE TO RELATED APPLICATION

This application is the § 371 U.S. National Stage of International Application No. PCT/US2014/060052 filed 10 Oct. 2014, which claims priority to U.S. Provisional Patent Application Ser. No. 61/890,552, filed Oct. 14, 2013, and U.S. Provisional Patent Application Ser. No. 61/971,142, filed Mar. 27, 2014, each of which is incorporated herein by reference.

SEQUENCE LISTING

This application contains a Sequence Listing electronically submitted to the United States Patent and Trademark Office via EFS-Web as an ASCII text file entitled "310-00780201_SequenceListing_ST25.txt" having a size of 5 KB and created on Oct. 10, 2014. Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein.

SUMMARY

This disclosure describes, in one aspect, a modular RNA regulator molecule. Generally, the modular RNA regulator molecule includes a recognition module and an inhibition module.

Generally, the recognition module includes a polynucleotide in which at least a portion of the polynucleotide recognizes at least a portion of a preselected pre-RNA. Generally, the inhibition module includes a moiety that inhibits nuclease processing of the preselected pre-RNA to a mature RNA.

In some embodiments, the RNA regulator molecule can be designed to recognize and regulate any target RNA. In certain embodiments, the target RNA can be a miRNA. In other embodiments, the RNA may be mRNA or a non-coding RNA.

In some embodiments, the recognition module can include a morpholino, a locked nucleic acid (LNA), a peptide nucleic acid (PNA), a phosphorothioate (S-oligo), or any synthetic/natural molecule that specifically recognizes unique pre-RNA sequences.

In some embodiments, the recognition module polynucleotide can include no more than 16 nucleotides.

In some embodiments, the inhibition module can include a moiety that directly interferes with the an enzymatic activity such as, for example, nuclease activity. In other embodiments, the inhibition module can include a moiety that indirectly interferes with an enzyme.

In some embodiments, the inhibition module can include a combination of two or more inhibition domains.

In some embodiments, the modular RNA regulator molecule can further include a linker module. In some of these embodiments, the linker module can be light-cleavable.

In some embodiments, the modular RNA regulator molecule can further include an accessory module.

In another aspect, this disclosure describes a method of inhibiting processing of a pre-RNA to a mature RNA. Generally, the method includes contacting a modular RNA regulator molecule with a sample that includes a targeted pre-RNA and nuclease capable of processing the targeted pre-RNA to a mature RNA in an amount effective to inhibit the nuclease from processing the pre-RNA to a mature miRNA.

In another aspect, this disclosure describes a method of inhibiting processing of a pre-RNA to a mature RNA in a cell. Generally, the method includes introducing into a cell a modular RNA regulator molecule in an amount effective to inhibit a nuclease from processing a preselected target pre-RNA to a mature RNA. In practicing this method, one can specifically inhibit processing of one RNA without adversely affecting processing of other RNAs.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 4. (A) Exemplary alternative Dicer inhibitors; (B) an exemplary alternative miRNA recognition antisense oligonucleotide, LNA; (C) an exemplary embodiment of modular miRNA regulator in which the inhibition module include a ligand that recruits and binds an endogenous protein FKBP12, which, when tethered to the recognition module through the ligand, sterically inhibits Dice nuclease activity; (D) an exemplary alternative design for a modular miRNA regulator.

FIG. 30. Dicer-mediated pre-miRNA cleavage assay. (A) Effects of MOs and inhibition modules. (B) Effects of inhibition module vs. bi-modular molecules.

DETAILED DESCRIPTION OF ILLUSTRATIVE EMBODIMENTS

Figure 1:
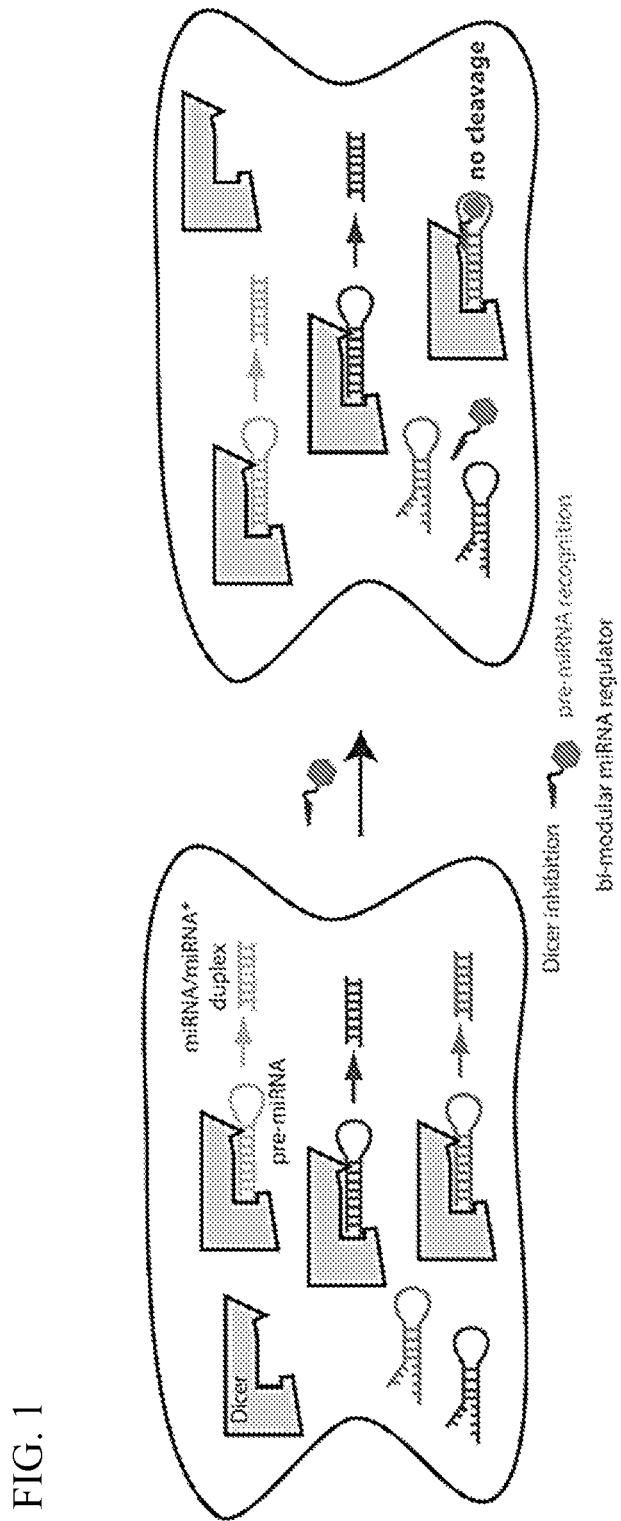
FIG. 1. A schematic diagram illustrating activity of one embodiment of a modular miRNA regulator.

MicroRNAs (miRNAs) are 21-25 nucleotide (nt)-noncoding RNAs that are encoded by distinct genes and regulate diverse cellular processes through epigenetic, transcriptional, translational, and/or posttranslational controls. Abnormal miRNA expression patterns correlate with various conditions including, for example, cardiomyopathies, various types of cancers, and various stages of cancers. For example, certain miRNAs—e.g., miR-21 and miR-155—affect cellular transformation, carcinogenesis and metastasis, and act as oncogenes (oncomiRs). Other miRNAs—e.g., miR-195 and miR-208a—are involved in cardiovascular development and abnormal expression of these miRNAs can result in, for example, congenital heart abnormalities.

While sometimes described in detail below in the context of inhibiting processing of miRNAs, the bi-functional regulators may be designed to regulate processing of any target RNA and the methods described herein may be practiced to regulate processing of any target RNA.

One approach used to control the levels of RNAs, including miRNAs, uses antisense oligonucleotide derivatives including, for example, phosphorothioates, peptide nucleic acids (PNAs), morpholinos (MOs), and/or locked nucleic acids (LNAs). The antisense oligonucleotide derivatives generally inhibit RNA function or production by steric disruption of interactions between, on the one hand, RNAs or pre-RNAs and, on the other hand, their associated biomolecule partners such as the RNA-induced silencing complex (RISC) or Dicer. To effectively control RNA levels, antisense oligonucleotides must compete successfully against macromolecular interactions between RNAs and their associated biomolecule partners. To ensure consistently successful competition, long antisense oligonucleotides, typically 25 nucleotides (nts) or more, are often used to provide high affinity.

Although using long oligonucleotides can ensure consistency and efficacy, it also increases the chances of off-target recognition. Each miRNA (21 to 25 nts) typically recognizes and regulates multiple mRNA sequences through imperfect pairing, where a 6-nucleotide to 8-nucleotide conserved seed sequence of each miRNA is complementary to at least a portion of its mRNA target, while different combinations of partial sequences outside the seed region can engage in co-recognizing various sequence-diverse mRNAs regulated by each miRNA. Similarly, such imperfect pairing and multi-target recognition can occur in cells when using similar length of antisense oligonucleotides to target miRNAs and can contribute to the unwanted off-target inhibition.

Besides lacking specificity, conventional methods can fail to precisely distinguish various miRNA functions. Many mature miRNAs are encoded by more than one precursor (i.e., pre-miRNA), each of which may be expressed from a different genomic locus. Each precursor may be under distinct regulatory control and each can contribute unequally to the mature miRNA level. It is unclear whether elevated levels of some miRNAs in diseased states result from the overexpression of a miRNA that is responsible for normal cellular processes or, alternatively, are caused by aberrant expression of a miRNA that is normally silent. Existing methods that sequester or disrupt mature miRNAs generally fail to differentiate the functional contributions of individual precursors. In addition, functions of miRNAs are often cellular context-dependent. Methods that allow one to precisely manipulate miRNA levels spatiotemporally can reveal and/or exploit miRNA functions in different cellular and environmental contexts.

Here, we describe a systematic approach to develop a new class of modular RNA regulators to address currently encountered off-target recognition problems in RNA regulation. The RNA regulators generally include a small molecule "inhibition module" and an oligonucleotide "recognition module" designed to target a specific pre-RNA. To decrease the extent of off-target recognition and inhibition, the modular RNA regulator molecules can control the maturation of chosen RNAs by controlling the activity of selective populations of nucleases that are responsible for converting a pre-RNA into the mature RNA. Global disruption of some nucleases (e.g., Dicer) can cause the loss of necessary mature RNAs and can consequently cause serious biological defects. In contrast, the modular RNA regulators disrupt the maturation of a chosen RNA by selectively inhibiting the catalytic turnover of the corresponding nuclease-pre-RNA complex (FIG. 1).

This disclosure describes exemplary modular miRNA regulators in which a nuclease inhibitor—an exemplary inhibition module—is covalently linked to a high affinity sequence-specific pre-miRNA recognition molecule—an exemplary recognition module. Despite being described in the context of the exemplary embodiment that includes the exemplary inhibition module and exemplary recognition molecule just described, the miRNA regulators may be designed to possess any desired recognition module and/or any desired inhibition module suitable for a particular application.

In one embodiment, the inhibition module can include a low affinity inhibitor of Dicer, a ribonuclease that processes short stem-loop, double-stranded pre-miRNAs (~70 nts) into mature miRNAs. As noted above, global disruption of Dicer—as may occur if one uses a high affinity Dicer inhibitor—can interfere with desired and necessary Dicer function. When used alone at low concentration, a weak-binding Dicer inhibitor can fail to inhibit Dicer activity and, therefore, fail to disrupt Dicer cellular function. In contrast, this embodiment of the modular miRNA regulator molecule is targeted to a preselected pre-miRNA whose cleavage by Dicer one may want to control. In the absence of the modular miRNA regulator, Dicer is able to cleave the preselected pre-miRNA. With the modular miRNA regulator selectively targeted to the preselected pre-miRNA, however, the low affinity Dicer inhibitor is in position to inhibit Dicer catalysis of the targeted pre-miRNA (FIG. 1). Moreover, in certain embodiments that include a cleavable linker between the inhibition module and the recognition module, described in more detail below, one can controllably restore Dicer activity if desired.

The modular miRNA regulator system described herein can, therefore, selectively inhibit nuclease function. Selective binding between the recognition module and the preselected pre-miRNA places the inhibition module in position to inhibit nuclease cleavage and, therefore, maturation of the pre-miRNA to mature miRNA. Moreover, the modular nature of the miRNA regulator molecules, in combination with the design and assembly methods described herein, allows one to readily design and produce unlimited adaptations to generate custom regulators against any miRNA of interest.

The recognition module generally includes a polynucleotide designed to selectively recognize a preselected precursor RNA (i.e., pre-RNA). Typically, the pre-RNA is preselected because one may desire to decrease levels—or at least control the level—of the mature RNA that is produced when the pre-RNA is processed. The bi-functional RNA regulators and methods described herein can be used to regulate function of any RNA such as, for example, a preselected mRNA, a preselected miRNA, or another preselected non-coding RNA.

Figure 2:
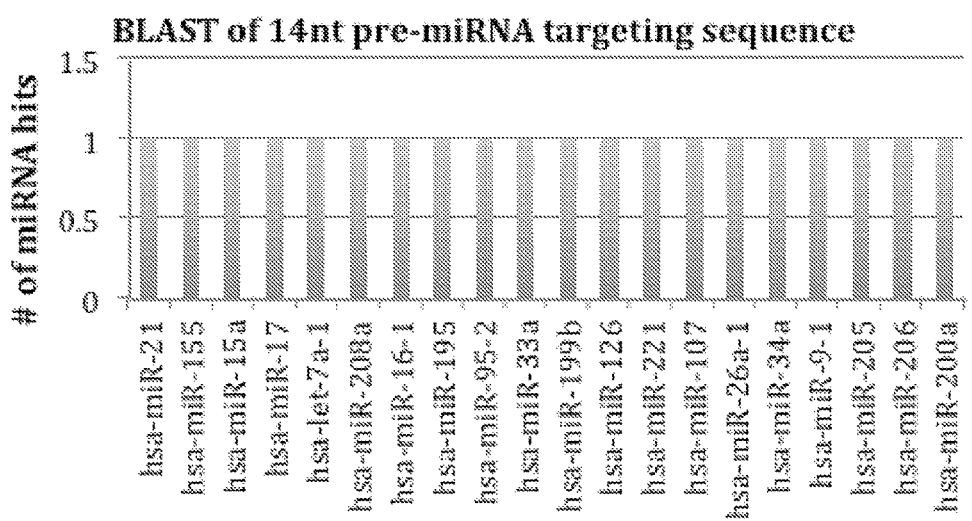
FIG. 2. BLAST analysis of 14-nucleotide pre-miRNA targeting sequences.

We first investigated whether 14-nucleotide pre-miRNA targeting sequences are unique and sufficient to recognize each chosen pre-miRNA. We performed a BLAST analysis using 14-nucleotide pre-miRNA hairpin-loop sequences chosen from 20 reported miRNAs associated with various human diseases, including cardiovascular disease, metabolic disease, cancer, and others. We found that among all tested pre-miRNA sequences, only the intended pre-miRNA is recognized for each input sequence (FIG. 2). This result confirmed the feasibility of using a 14-nucletide antisense oligonucleotide as the recognition modules to selectively recognize a unique pre-miRNA the cells.

One feature of the recognition module is designed to decrease off-target inhibition. In some embodiments, the recognition module can include a nucleotide designed to target a unique single-strand hairpin loop region of a chosen pre-RNA. Targeting exposed single-strand regions can expedite binding of recognition module to the targeted sequences without competing with existing double-stranded sequences. As noted above, different pre-RNAs expressed from different genomic loci can be processed to produce identical mature RNAs. The hairpin loop regions of the various pre-RNAs from different genomic loci are not conserved, however. Thus, by targeting genome locus-specific pre-RNA hairpin sequences, the modular inhibitors can selectively inhibit cleavage of a particular pre-RNA from among all of the pre-RNAs that produce a given mature RNA.

In some embodiments, a morpholino may be used as the recognition module. Morpholinos typically have standard nucleic acid bases linked to morpholine rings, which are connected through phosphorodiamidates instead of phosphodiester linkages. With such unnatural backbones and uncharged linkages, morpholinos can be less susceptible to nuclease degradation while maintaining high affinity to the targeted single strand RNAs. Also, a morpholino can invade a double-stranded RNA region from a morpholino-bound single-strand region, which can promote successful binding of the modular regulators to the targeted pre-miRNAs.

FIG. 2 shows that a 14-nucleotide sequence is sufficient to differentiate a unique pre-miRNA among all existing pre-miRNAs. The melting temperatures of typical 14-nucleotide DNA-DNA duplexes are in the range of physiological temperature. Since the stability of a morpholino-RNA duplex is typically higher than a DNA-DNA duplex, a 14-nucleotide morpholino can form duplexes with targeted pre-miRNA sequences in the cells that are sufficiently stable to deliver the inhibition module to sufficient proximity of the nuclease to elicit inhibition of the nuclease.

Importantly, polynucleotides of 14 nucleotides are shorter than the minimal inhibitory length of morpholinos, which is the shortest morpholino length to result in any observable morpholino-induced biological effects. A 25-nucleotide morpholino, for example, can induce morpholino-mediated effects if the morpholino binds to a cellular RNA species that forms a duplex with the morpholino that is longer than the minimal inhibitory length. In contrast, for example, a 14-nucleotide morpholino recognition module will not, in and of itself, interfere with the normal function of any bound cellular RNA species, but is sufficient for unique premiRNA recognition and stable binding. When the recognition module is linked to an inhibitor of a particular nuclease (e.g., Dicer), only pre-miRNAs that are processed by the specified nuclease will be affected. Other RNA species will not be affected—e.g., cellular mRNA or miRNA species processed by other nucleases. The recognition module therefore allows one to selectively control levels of miRNA based on a combination of (a) a particular pre-miRNA precursor and (b) the nuclease that processes the pre-miRNA into the mature miRNA, thereby reducing unwanted interference against other RNA species.

Although described above in the context of embodiments in which the recognition module includes a morpholino, the recognition modules can be any suitable polynucleotide including, for example, a locked nucleic acid (LNA), a peptide nucleic acid (PNA), a phosphorothioate (S-oligo), a single-stranded DNA, an unmodified RNA, or any modified/unmodified nucleic acid recognition molecules such as, for example, cyclic-peptides or synthetic small molecules or natural products.

Generally, the recognition module has a length that is sufficient to provide selective recognition of the intended target pre-miRNA. Thus, the recognition module can include a polynucleotide that has a minimum length of at least 5 nucleotides such as, for example, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides, at least 23 nucleotides, at least 24 nucleotides, at least 25 nucleotides, at least 26 nucleotides, at least 27 nucleotides, at least 28 nucleotides, at least 29 nucleotides, or at least 30 nucleotides. As used herein, "selective recognition" refers to the property of being able to differentiate between two or more alternatives such as, for example, two or more pre-miRNAs. "Selective recognition" is not intended to suggest that the recognition module necessarily possesses unitary specificity for the intended target pre-miRNA, although such a level of selective recognition is possible.

The recognition module also generally has a length that is short enough so that it limits direct but collateral biological effects. Thus, the recognition module can include a polynucleotide that has a maximum length of no more than 45 nucleotides such as, for example, no more than 40 nucleotides, no more than 35 nucleotides, no more than 30 nucleotides, no more than 29 nucleotides, no more than 28 nucleotides, no more than 27 nucleotides, no more than 26 nucleotides, no more than 25 nucleotides, no more than 24 nucleotides, no more than 23 nucleotides, no more than 22 nucleotides, no more than 21 nucleotides, no more than 20 nucleotides, no more than 19 nucleotides, no more than 18 nucleotides, no more than 17 nucleotides, no more than 16 nucleotides, no more than 15 nucleotides, no more than 14 nucleotides, no more than 13 nucleotides, no more than 12 nucleotides, no more than 11 nucleotides, or no more than 10 nucleotides.

In some embodiments, the recognition module may be a polynucleotide having a length defined by a range having endpoints any minimum length listed above and any maximum length listed above that is greater than the minimum length.

The recognition molecule may be modified so that it is detectable in a subsequent assay by, for example, incorporating a detectable marker to the recognition module polynucleotide. This may be accomplished by, for example, using a radiolabeled polynucleotide and/or coupling, for example, a fluorophore or a chromophore to the recognition module polynucleotides such as, for example, through the free amino group at the 5' end of the recognition module polynucleotide.

The modular design of the bi-functional RNA regulator molecules described herein means that any RNA recognition molecule can be transformed into an RNA inhibitor by linking a direct inhibitor module or an indirect inhibitor module to the recognition module.

The inhibition module may include any moiety capable of directly or indirectly interfering with a protein-RNA interaction. In many cases, the protein involved in the protein-RNA interaction may be an enzyme (e.g., a nuclease) so that the inhibition module interferes with the enzymatic activity of the enzyme, regardless of the mechanism by which the moiety interferes with the enzymatic activity. As used herein, the term "moiety" refers to a portion of a chemical compound—including, e.g., a short peptide—that exhibits a particular character such as, for example, a particular biological or chemical function (e.g., nuclease inhibition, ligand binding, etc.). As used herein, a moiety of an inhibition module (or "inhibition moiety") directly interferes with enzymatic activity if at least a portion of the moiety binds to any portion of the enzyme (e.g., an active site) in a manner that inhibits the ability of the enzyme to perform its catalytic function on the pre-RNA. The binding may be covalent or non-covalent (e.g., hydrogen bonding), permanent or reversible. An inhibition moiety also directly interferes with enzymatic activity if it sterically interferes with the ability of the enzyme to access the reactive site on the preselected pre-RNA such as, for example, if the inhibition moiety shields the pre-RNA site from access to the enzymatic binding site or active site.

An inhibition moiety indirectly interferes with enzymatic activity if it does not directly interact with the enzyme, but instead binds to another molecule and therefore places the other molecule in position to interfere with enzymatic activity. Like an inhibition moiety that directly interferes with enzymatic activity, a bound enzyme-interfering molecule may inhibit enzyme activity in any suitable manner including, for example, binding to the enzyme or providing steric interference.

In other embodiments, the inhibition module may inhibit a protein-RNA interaction that does not necessarily involve inhibiting enzymatic activity. Most RNAs, whether they encode a protein or are non-coding, exert their biological functions through the interactions with corresponding proteins. For example, the translation of an mRNA involves interactions between the mRNA and various translation regulating proteins and/or translation machinery including, for example, ribosomes and other associated proteins. Maturation of a non-coding RNA, including an miRNA, a lincRNA and/or others, involves interactions with other proteins/protein complexes to mature. Several human diseases are mediated through the interactions between proteins and RNAs. Blocking these interactions can prevent the progression of the diseases. For example, myotonic dystrophy type 1 (DM1) is caused when an expanded r(CUG) repeat binds the RNA splicing regulator muscleblind-like 1 protein (MBNL1). The human immunodeficiency virus (HIV) Rev responsive element (RRE) of the viral mRNA has to bind to the Rev protein to be exported to cytoplasm to allow the translation and to proceed with the infection cycle. The hepatitis C virus (HCV) internal ribosome entry site (IRES) has to recruit ribosome to produce essential viral proteins for infection. Interfering with such protein-RNA interactions can provide therapy for such diseases.

Thus, while described above in the context of an embodiment in which the inhibition module includes an inhibitor of the Dicer nuclease, the inhibition module can include an inhibitor of any particular protein-RNA interaction whose inhibition is desired for a particular application. Thus, the inhibition module can include an inhibitor of Dicer (e.g., N-hydroxyphthalimide), an inhibitor of Drosha (which processes pre-miRNA), or of any ribonuclease that processes dsRNAs (e.g., FIG. 4A). In some embodiments, the inhibition module can include any ligand that recruits and binds an endogenous molecule that sterically blocks a nuclease from processing the pre-miRNA (e.g. SLF/FK506 recruits FKBP, dexamethasone recruits DHFR) (FIG. 4C). In still other embodiments, the inhibition module can include a moiety that inhibits binding between an expanded r(CUG) repeat and MBNL1, inhibits binding between HIV RRE and Rev protein, inhibit binding between hepatitis C IRES and a ribosome, etc.

Moreover, in some embodiments, an inhibition module can include a combination of two or more inhibitor moieties. When an inhibition module includes two or more inhibitor moieties, each moiety may be selected and designed independently of the other inhibitor moiety or moieties.

By using this modular design, one can construct a modular regulator designed to control levels of any RNA of interest. Thus, for example, one can construct a modular RNA regulator designed to deliver Dicer inhibition using recognition modules designed to target miRNAs associated with, for example, cancer (e.g., miR-21 or miR-155), cardiovascular conditions (e.g., miR-195 or miR-208a), infectious diseases (e.g. miR-122), metabolic diseases (miR-33), neurological or neurodegenerative diseases (e.g. miR-146, miR-206), autoimmune diseases (e.g. miR-146a, miR-101), or any miRNA associated with any other condition. Exemplary conditions and miRNAs associated with the conditions are available from numerous public sources including, for example, the human microRNA disease database (HMDD).

In some embodiments, the RNA regulator molecule can further include a linker module selected to provide an appropriate spacing between the recognition module and the inhibition module to position the inhibition module in appropriate proximity to the nuclease after the recognition module selectively binds to the target pre-RNA. For example, a linker module can approximate the distance between a hairpin loop of the targeted pre-RNA and the active site of the nuclease so that when the modular RNA regulator molecule selectively binds to the targeted pre-RNA at the hairpin loop, the inhibition module will be in the appropriate vicinity of the active site of the nuclease. Exemplary linkers that may be used in a linker module include, for example, hydrophilic polymers such as, for example, ethylene glycol, synthetic rigid or flexible linkers or peptides.

In some embodiments, the linker may be selected to be controllably cleavable so that the nuclease inhibition provided by the modular RNA regulator molecule can be inactivated in a controlled manner. For example, the linker module can include a photo-cleavable linker (FIG. 1B). The illustrated photo-cleavable linkers include an embedded orthonitrobenzyl (ONB)-based group that can be synthesized by adapting reported procedures (Choi et. al. *Bioorg. Med. Chem.*, 20:1281-1290 (2012); Ouyang et. al. *J. Am. Chem. Soc.*, 131:13255-13269 (2009)). The photo-cleavable linker may be controllably cleaved by exposure to an appropriate light source. For example, the ONB linkers can be cleaved by UV light (365 nm) within seconds, or the brominated hydroxyquinoline (BHQ) linker can be cleaved by two-photon excitation. Upon light-induced cleavage of the linker, the inhibition module may be no longer tethered to the recognition module, thereby inactivating the RNA regulator molecule and allowing processing of the previously targeted pre-RNA to mature RNA. In other embodiments, a controllably cleavable linker may be cleaved by, for example, enzymatic activity (whether endogenous to the cell or introduced into the cell), or chemically.

The controlled inactivation of the modular RNA regulator molecule can be verified by treating cells with either a photo-cleavable modular RNA regulator targeting a specified RNA or a non-cleavable version the modular RNA regulator in an amount and for a time effective to knockdown endogenous levels of the targeted RNA. The cells may then be irradiated with UV light under appropriate photocleavage conditions for the photo-cleavable linker to be cleaved and then the cells may be cultured an appropriate length of time before the cells are harvested to isolate total RNA for QRT-PCR-based assays to analyze the level changes of the targeted RNA after photo-cleavage of the modular RNA regulator molecule.

In some embodiments, the modular RNA regulator molecule can further include an accessory module selected to provide a desired function to the molecule. For example, the RNA regulator can include an accessory module designed or selected to increase the speed and/or efficiency at which the RNA regulator molecule is taken up by the organ, tissue, and/or cells that express the pre-RNA whose processing to mature RNA is to be regulated. Such an accessory module may be attached via a linker, as described above, including a controllably cleavable linker so that once the RNA regulator molecule enters the targeted cells, the accessory module may be discarded. Alternative exemplary accessory modules can include an accessory module that temporarily inactivates or shields either the recognition module or the inhibition module until the RNA regulator molecule is delivered to the targeted cell. Such an accessory module can limit the extent to which the RNA regulator molecule is able to elicit undesired activity if taken up by cells, tissues, and/or organs that are not the cells, tissues, and/or organs to which the RNA regulator molecule is targeted. Other exemplary accessory modules can include, for example, an accessory module that modifies the pharmacokinetic/dynamic properties of the regulators in the body.

Figure 3A:
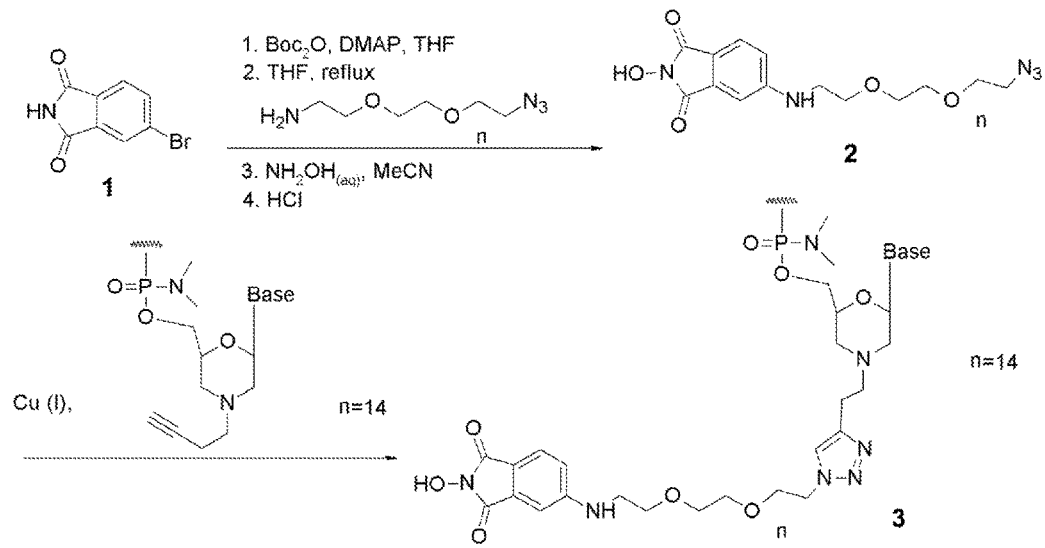
FIG. 3. (A) Synthesis of a modular miRNA regulator; (B) Exemplary light-cleavable linkers.
Figure 3B:
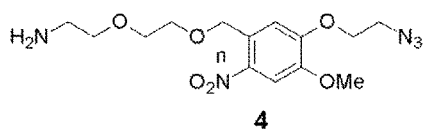
Figure 3B:
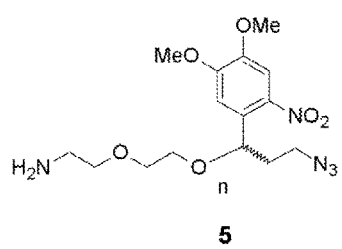

FIG. 3A shows one scheme for synthesizing a modular miRNA regulator molecule (Compound 3). A nuclease inhibitor (Compound 1) is linked to a sequence-specific 14-nucleotide morpholino through a flexible linker. After synthesis, one can verify the nuclease-inhibiting activity of the modular regulator compound using a reconstituted cell free system with nuclease proteins and radioactively labeled pre-miRNAs to examine pre-miRNA cleavage in the presence or absence of synthesized modular regulator compound.

The scheme shown in FIG. 3A illustrates synthesis of one embodiment of a modular regulator compound. The illustrated embodiment has a Dicer inhibition module that includes a low affinity (mM) RNase III inhibitor, N-hydroxyphthalimide. N-hydroxyphthalimide and similar compounds inhibit RNase III family enzymes by presenting three oxygen atoms at positions and distances that can coordinate and sequester the two divalent metal ions (e.g., $Mg^{2+}$ in Dicer) in the active site. Based on the Dicer-premiRNA crystal structure, the distance from the Dicer active site to the far end of the single strand hairpin loop is approximately 30 Å, which corresponds to the linker length of no more than n=5 in this exemplary design. Flexible hydrophilic ethylene glycol-type linkers of different lengths (n=1 to 6) can be synthesized and coupled to the Dicer inhibitor. An azido handle can be installed for the coupling to the pre-miRNA recognition module through click chemistry, which enables a clean and easy conjugation between an azido and an alkynyl molecule using a copper catalyst.

Again, although the preceding description is in the context of an embodiment in which the inhibition module includes the Dice inhibitor N-hydroxyphthalimide, other embodiments can include other nuclease inhibitors, other enzymes, or inhibitor moieties that inhibit other non-enzymatic RNA-protein interactions. In some of these embodiments, the alternative inhibitors may likewise be RNase III inhibitors and/or may disrupt two-metal-ion-catalyzed dsRNA cleavage. In other embodiments, however, the inhibition module can include any of the suitable inhibitor moieties described more generally above.

To target a particular pre-RNA, one can select a unique sequence containing a single-stranded exposed hairpin loop of the RNA. Exemplary sequences selected for targeting selected exemplary pre-miRNAs are shown in Table 1.

TABLE 1

| Target pre-miRNA | Recognition module sequence | SEQ ID NO |
|---|---|---|
| pre-miR-21 | guugaaucuc augg | 1 |
| pre-miR-155 | uuugccucca acug | 2 |
| pre-miR-15a | gauuuugaaa aggu | 3 |
| pre-miR-17 | ugauaugugc aucu | 4 |
| pre-miR-7a-1 | cacacccacc acug | 5 |
| pre-miR-208a | accugaugcu cacg | 6 |
| pre-miR-16-1 | aagauucuaa aauu | 7 |
| pre-miR-195 | agggaagcga gucu | 8 |
| pre-miR-92a-2 | guguucuaua uaaa | 9 |
| pre-miR-33a | uucgguggu accc | 10 |
| pre-miR-199b | aggacuccca aauu | 11 |
| pre-miR-126 | ugugacacuu caaa | 12 |
| pre-miR-221 | uguucguuag gcaa | 13 |
| pre-miR-107 | guggcaugga guuc | 14 |
| pre-miR-26a-1 | gugcaggucc caau | 15 |
| pre-miR-34a | gagcaauagu aagg | 16 |
| pre-miR-9-1 | ugguguggag ucuu | 17 |
| pre-miR-205 | cucauaccca acca | 18 |
| pre-miR-206 | uggauuacuu ugcu | 19 |
| pre-miR-200a | uuucccagcu ugac | 20 |

The selected recognition module sequence can be synthesized—as a morpholino, LNA (FIG. 4B), PNA, S-oligo, or other appropriate polynucleotide—with appropriate modifications (e.g., 3'-alkynyl-modification) for conjugating to the inhibition module or linker module of the modular regulator compound (see, e.g., FIG. 3A).

FIG. 4 illustrates some exemplary alternative embodiments. FIG. 4A illustrates alternative ribonuclease III inhibitors that may be used as the inhibition module. FIG. 4B illustrates the use of an LNA as the recognition module. FIG. 4C illustrates a strategy in which the inhibition module does not directly inhibit the nuclease. Instead, the inhibition module includes a ligand that binds to an endogenous protein in the cell. As illustrated in FIG. 4C, one exemplary ligand, SLF (Synthetic Ligand of FKBP, (1R)-1-(3-aminophenyl)-3-(3,4-dimethoxyphenyl)propyl ester-1-(3,3-dimethyl-1,2-dioxopentyl)-2S-piperidinecarboxylic acid, Cayman Chemical Co., Ann Arbor, Mich.), recruits and binds the exemplary endogenous protein FKBP12. The recruitment of FKBP12 to the nuclease/pre-miRNA interface sterically disrupts the macromolecular interactions necessary for the nuclease to process the pre-miRNA.

Figure 5:
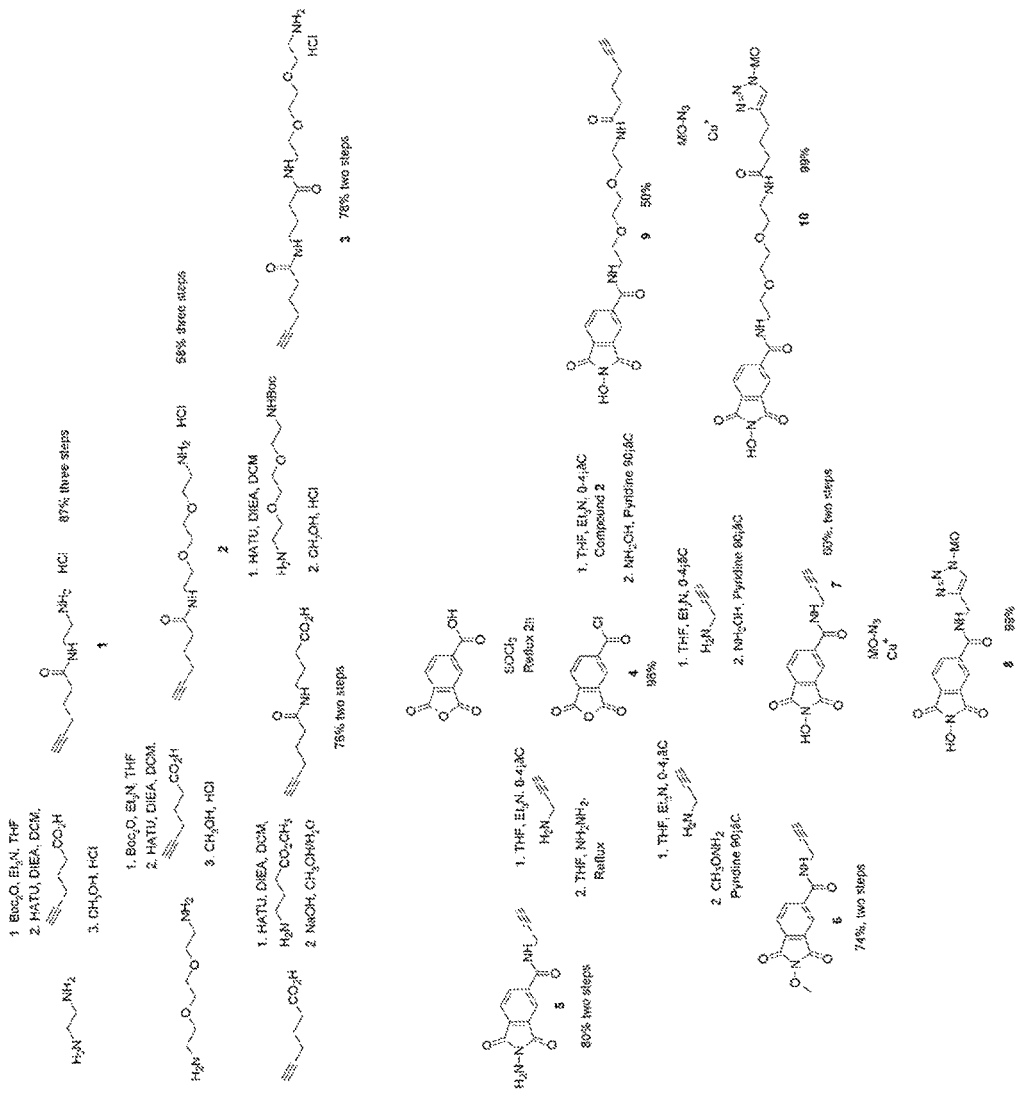
FIG. 5. Synthesis of designed bi-functional miRNA regulators.
Figure 6:
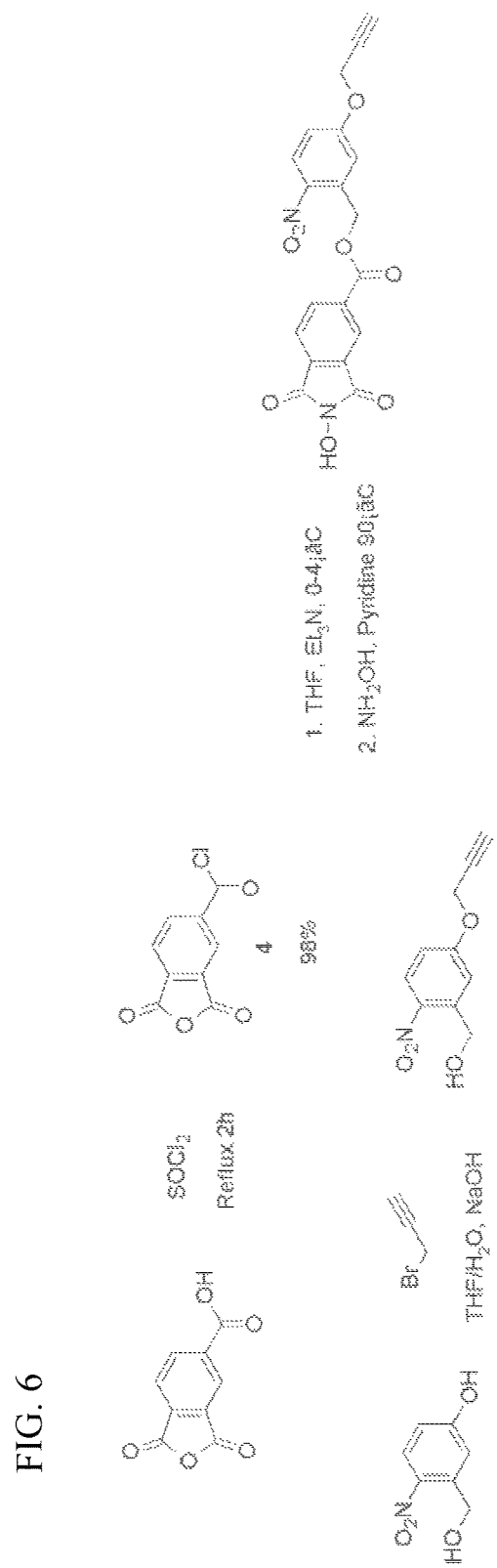
FIG. 6. Synthesis of Dicer inhibitor with a photocleavable linker, which can be conjugated to a morpholino through click chemistry.
Figure 7:
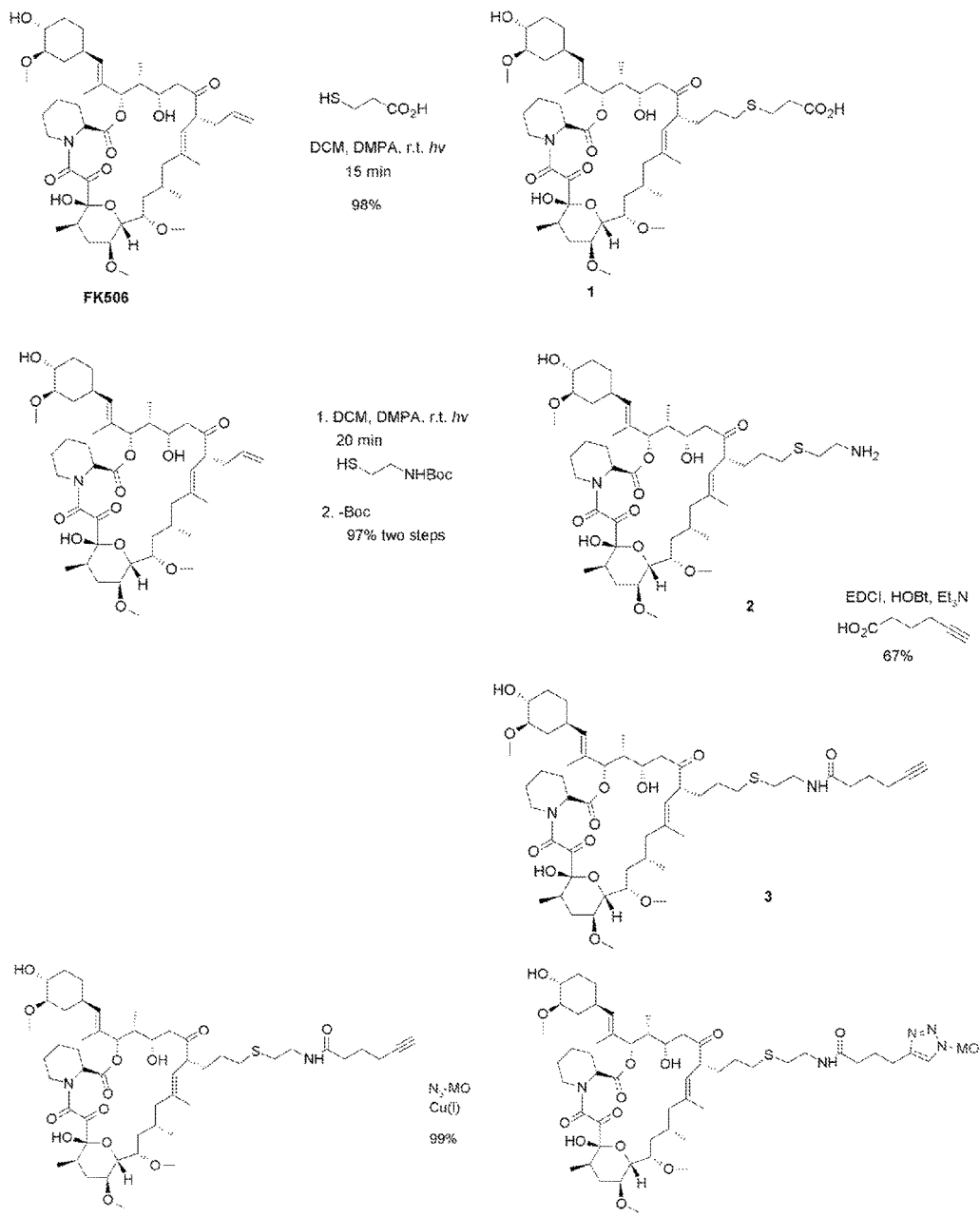
FIG. 7. Synthesis of alternative bi-functional miRNA regulator that inhibit miRNA maturation through steric blocking FIG. 8. Test the 14-nt morpholino miRNA recognition module in blocking miR-21 maturation. Ln1: pre-miR-21, Ln2: pre-miR-21+Dicer, Ln3: pre-miR-21+Dicer+14-nt morpholino 100 nM, Ln4: pre-miR-21+Dicer+25-nt morpholino 100 nM.

FIG. 5 illustrates synthetic methods of exemplary linkers of different lengths and their coupling to three different inhibitor units. FIG. 6 illustrates the synthetic methods of an exemplary photo-cleavable linker. FIG. 7 illustrates the synthetic methods of linking a linker to an exemplary FKBP12 recruiting ligand, tacrolimus.

After synthesis, one can test the nuclease inhibiting activity of the modular RNA regulator compounds in vitro using any conventional in vitro assay for detecting nuclease activity. For example, one can use purified or recombinant nuclease (e.g., Dicer) and appropriately labeled pre-miRNAs to investigate, for example, the inhibition efficacy and/or selectivity of the modular miRNA regulator molecules in vitro. One can evaluate the ability of the nuclease to process labeled pre-miRNAs into mature miRNAs by the nuclease in either the presence or absence of the modular miRNA regulator molecules. Typical pre-miRNAs are approximately 70 nucleotides in length, whereas processed mature miRNAs typically are approximately 22 nucleotides in length. The extent of processing can be evaluated using any suitable method for detecting differences in the lengths of polynucleotides such as, for example, denaturing polyacrylamide gel electrophoresis.

Figure 9:
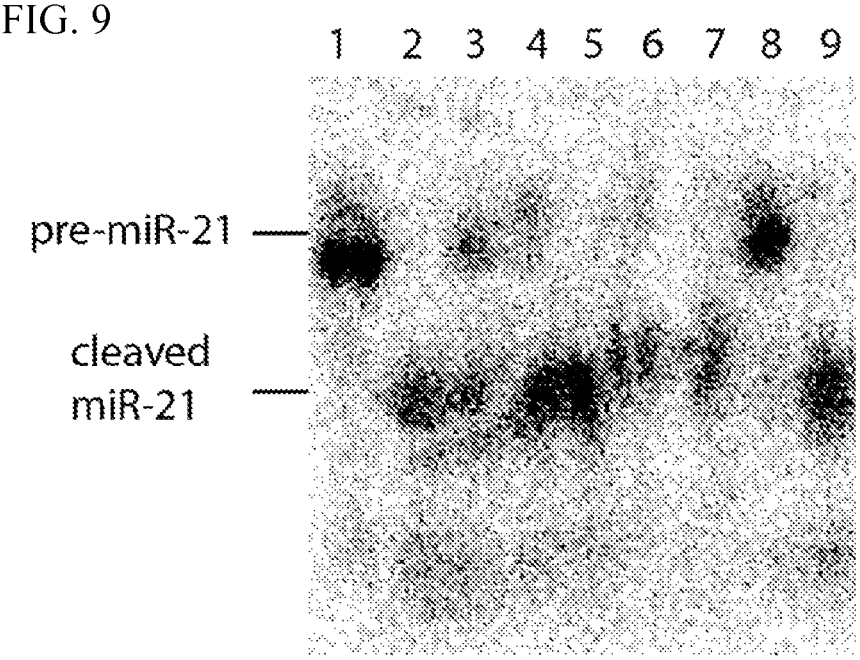
FIG. 9. Test the bi-functional miR-21 regulator in blocking miR-21 maturation. Ln1: pre-miR-21, Ln2: pre-miR-21+Dicer, Ln3: pre-miR-21+Dicer+25-nt morpholino 100 nM, Ln4: pre-miR-21+Dicer+14-nt morpholino 1 µM. Ln5: pre-miR-21+Dicer+14-nt morpholino 100 nM. Ln6: pre-miR-21+Dicer+Dicer inhibition module only 1 µM. Ln7: pre-miR-21+Dicer+Dicer inhibition module only 100 nM. Ln8: pre-miR-21+Dicer+bi-functional miR-21 regulator 1 µM. Ln9: pre-miR-21+Dicer+bi-functional miR-21 regulator 100 nM.

As a result of such in vitro analysis, one can determine the concentration of modular miRNA regulator molecule that can effectively inhibit the targeted nuclease while at the same time limiting pan-cellular nuclease inhibition. Thus, one can determine the concentration of modular miRNA regulator molecule that is effective to inhibit undesirable nuclease activity—e.g., nuclease activity associated with a disease condition—while limiting the extent to which desirable and necessary biological activity of the nuclease is disrupted. For example, FIG. 9 shows data demonstrating that a bi-functional miRNA regulator at a concentration of 1 μM (FIG. 9, lane 8) inhibits Dicer processing of pre-miR-21, whereas a comparable bi-functional miRNA regulator provided at a concentration of 100 nM failed to inhibit Dicer-mediated processing of the miRNA (FIG. 9, lane 9).

Figure 8:
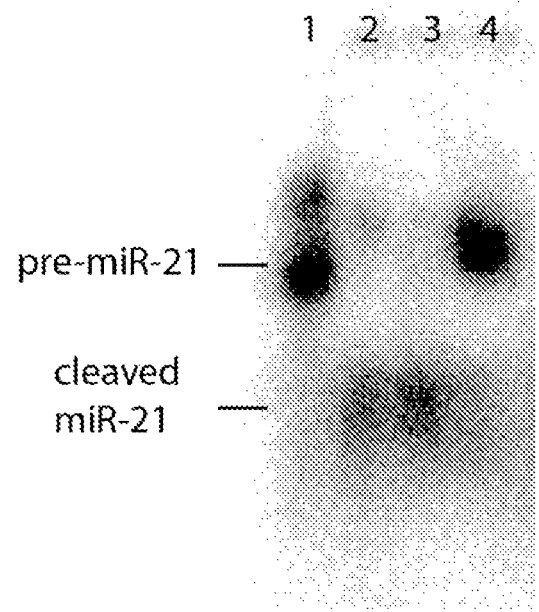

The in vitro analysis also can allow one to determine the optimal length of the recognition module polynucleotide so that the modular miRNA regulator molecule possesses sufficient selectivity for the target pre-miRNA while limiting any direct collateral biological effects of the recognition module polynucleotide. For example, FIG. 8 shows that a bi-functional miRNA regulator having a 14-nt morpholino as a recognition module fails to inhibit Dicer-dependent pre-miRNA processing (FIG. 8, lane 3). In contrast, a bi-functional miRNA regulator having a 25-nt morpholino as the recognition module effectively inhibits Dicer processing of the pre-miRNA.

For embodiments in which the RNA regulator molecule includes a linker module, the in vitro analysis also can allow one to determine the optimal linker length. It is possible that a linker of standard length may be suitable for many nuclease/pre-RNA combinations. A desired level of nuclease inhibition for some nuclease/pre-RNA combinations, however, may be more readily achieved using a linker that varies somewhat from any standard length.

The in vitro analysis also can allow one to verify the selectivity of the RNA regulator molecules. One can, for example, test the processing of multiple pre-RNAs by a nuclease in the presence of a modular RNA regulator molecule targeted to only one of the pre-RNAs. Sufficient selectivity is achieved when processing of only the targeted RNA is inhibited by the modular RNA regulator molecule.

One can also verify certain cellular characteristics of the modular RNA regulator molecules in cell-based in vitro assays. For example, one can verify the cell permeability and ability to reduce endogenous levels of the targeted miRNAs in an appropriate cell line. As one example, miR-195 and miR-208a are associated with cardiovascular conditions. miRNA regulator molecules that target miR-195 or miR-208a may be analyzed for their ability to enter cardiomyocytes (or another appropriate model cell type) and/or reduce endogenous levels of these mature miRNAs in cardiomyocytes (or other appropriate model cells). As another example, miR-21 and miR-155 are associated with certain cancers. miRNA regulator molecules that target miR-21 or miR-155 may be analyzed for their ability to enter cells from an established cancer cell line (or another appropriate model cell type) and/or reduce endogenous levels of these mature miRNAs in cardiomyocytes (or other appropriate model cells).

In another aspect, this disclosure describes an efficient one-step functionalization of tacrolimus by the thiol-ene click (TEC) reaction. This approach, which can enable rapid and quantitative generation of, for example, bioactive FK1012 and tacrolimus derivatives, can facilitate biomedical applications of tacrolimus-coupled molecules and expand the scope of TEC reaction in natural product semi-synthesis.

Tacrolimus (Compound 1 in FIG. 11) is a natural product that binds specifically to the abundant and ubiquitous mammalian protein, FK506-binding protein 12 (FKBP12). This unique recognition property has been advantageously used in various biomedical research applications. Tacrolimus is an FDA approved immunosuppressant agent that blocks the calcineurin phosphatase active site near the composite surface of the FK506/FKBP12 complex. In addition, various applications exploit the tacrolimus-mediated recruitment of FKBP 12. In one such application, coupling two tacrolimus molecules with a linker creates a homo-dimerizer, FK1012, which has been used in chemically induced proximity (CIP) technology to promote dimerization of FKBP12-tagged proteins and control a variety of downstream cellular processes. Another application involves linking tacrolimus or the synthetic ligand of FKBP (SLF) to other protein binding ligands to generate hetero-dimerizers that induce the association of FKBP12-fused proteins with other proteins. Conjugating FKBP12-binding ligands to other small molecules can lead to the formation of small molecule-FKBP 12 complexes in which the small molecule components gain modified properties. For example, formation of these complexes can add bulkiness to the small molecule that can sterically block protein-protein interaction, increase the recognition surface that alters binding affinity and selectivity, and/or modulate cellular context-dependent protein recognition. Generating a small molecule-FKBP 12 complex also can protect the small molecule from cytochrome p450-mediated metabolic clearance and, therefore, increase the half-life of the small molecule in vivo.

Although SLF has a 10-fold decreased affinity for FKBP12 when compared to that of tacrolimus, it is a commonly used FKBP12-recruiting ligand to link to other molecules. SLF may be readily subjected to chemical derivatization through its aniline and/or carboxylate group. However, SLF is extremely expensive and an 8-step to 12-step route is needed for its synthesis in only moderate yields. In contrast, tacrolimus is commercially available at a much lower cost and has a much higher FKBP12-binding affinity. Nevertheless, its structural complexity and the lack of easily modifiable chemical handles make tacrolimus derivatives less accessible.

Thus far, several methods have been reported to modify tacrolimus at the C39 position through chemical manipulation of the C21 allyl group. Modifications at this site, which is involved in calcineurin recognition, can destroy calcineurin binding without impacting the affinity for FKBP12. Some of the methods employed for tacrolimus modification require multi-step transformations, multiple protecting group manipulations, and proceed in low overall yields. Others, which employ Grubbs' type cross metathesis to convert the exocyclic alkene moiety of tacrolimus into other functional groups, take place in a single step with modest yields (34-49%). One recent approach using microwave-assisted cross metathesis generated tacrolimus derivatives in moderate to excellent yields (35 to over 95%) within minutes at high temperatures (approximately 150° C.). However, the requirement for special microwave instrumentation and the inconsistencies among different microwave apparatuses limit the general applicability of this method.

A thiol-ene click (TEC) reaction is a reaction that occurs between thiols and alkenes to produce anti-markovnikov thioethers through a photo-initiated, free-radical mechanistic pathway. TEC reactions are used in several applications in polymer synthesis and carbohydrate/protein modifications. TEC reactions tolerate various functional groups and proceeds rapidly under mild, aerobic conditions. Moreover, TEC reactions do not require expensive and/or potentially toxic metal catalysts or any special apparatus. The TEC reaction is considered to be photo-click chemistry because the reaction has the same robustness, selectivity, simplicity, and mildness as does click chemistry.

The TEC reaction can be used to modify tacrolimus through its unique exocyclic alkene group. Several common chemical groups used in deriving bioactive molecules, including, for example, an amine, a carboxylic acid, an alkyne, and/or an azide, can be easily and rapidly installed onto tacrolimus by using a TEC reaction. The processes are initiated by using a handheld UV lamp without the need of special photo-reactors and proceed smoothly in various organic solvents or with water as a co-solvent. Finally, a bioactive FK1012 can be synthesized in a single step in quantitative yield within minutes.

Figure 11:
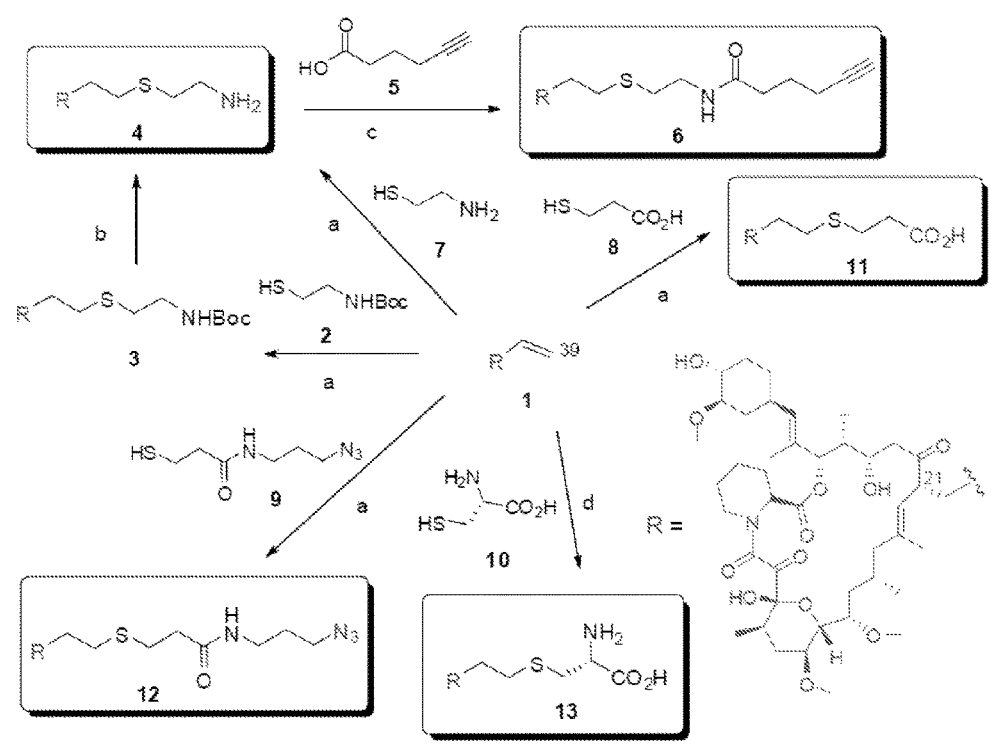
FIG. 11. Synthesis of tacrolimus derivatives.

To investigate the feasibility of using the TEC reaction to derivatize tacrolimus, we first examined the reaction of unprotected tacrolimus with the simple thiol, Boc-cysteamine (Compound 2, FIG. 11). For this purpose, the mixture of equal molar ratio of tacrolimus and Compound 2 (FIG. 11) along with a 0.05 equivalent (eq) of the photo initiator 2,2-dimethoxy-2-phenylacetophenone (DPAP) was dissolved in dicloromethane (DCM) and irradiated using a handheld UV lamp ($\lambda_{max}$ 365 nm). The reaction was carried out at room temperature under normal atmospheric condition without any special degassing or drying procedure. Notably, the reaction proceeded rapidly with the thin-layer chromatography (TLC) analysis showing that complete conversion occurred within 15 minutes. The product, Compound 3 (FIG. 11) was easily purified by flash chromatography in near quantitative yield. Analysis of the NMR and mass spectrometric data verified that Compound 3 (FIG. 11) was generated through the regioselective exocyclic alkene coupling.

Figure 14:
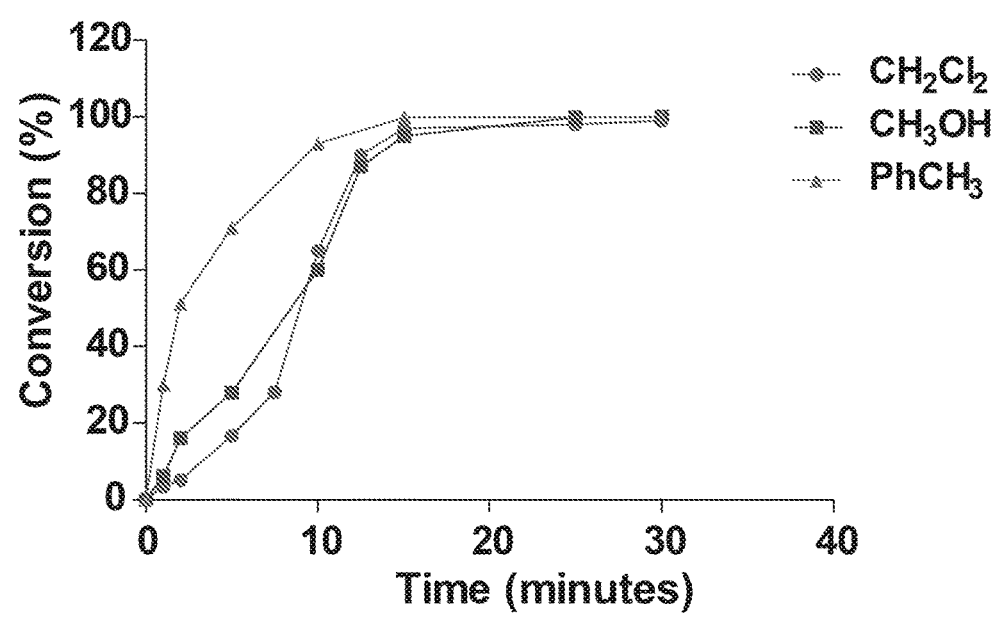
FIG. 14. TEC reaction time profile. The conversion was based on tacrolimus consumption followed under HPLC.

To test the potential of using TEC for coupling chemical moieties that may have varied solvent solubility, TEC reactions between tacrolimus and Compound 2 (FIG. 11) were carried out in DCM, toluene, or methanol for 15 minutes under the described conditions. All three reactions, taking place in solvents with very different polarities and protic natures, produced the coupling product, Compound 3 (FIG. 11) in near quantitative isolated yields (Table 2). To probe the rates, the above reactions were monitored using the high-performance liquid chromatography (HPLC). In all cases, significant conversions were observed within 10 minutes and the reactions were complete within 15-20 minutes (FIG. 14). The Boc-group of Compound 3 (FIG. 11) can be removed to give the corresponding amine, Compound 4 (FIG. 11), which can be readily converted into other desired functional groups. Employing this approach, we prepared the tacrolimus alkyne derivative, Compound 6 (FIG. 11) through amide coupling with the alkyne-containing acid, Compound 5 (FIG. 11). The alkyne group in Compound 6 (FIG. 11) can be used to introduce other fragments through the copper-catalyzed click chemistry.

TABLE 2

TEC between tacrolimus (Compound 1, FIG. 11) and Compounds 2 and 7-10 (FIG. 11)

| Compounds | Solvent | Conversion[a] | Yield (%)[b] |
|---|---|---|---|
| 3 | DCM | 100 | 98 |
| 3 | PhCH$_3$ | 100 | 95 |
| 3 | CH$_3$OH | 100 | 97 |
| 4 | CH$_3$OH | 100 | 97 |
| 11 | DCM | 100 | 98 |
| 12 | DCM | 100 | 95 |
| 13 | CH$_3$OH/H$_2$O (3:1) | 100 | 97 |

[a]Based on consumption of tacrolimus, monitored using HPLC;
[b]isolated yields of column chromatography-purified products.

To enable more efficient chemical derivatization of tacrolimus, we investigated the feasibility of directly coupling unprotected tacrolimus with thiols like cysteamine (Compound 7, FIG. 11), 3-thiopropanoic acid (Compound 8, FIG. 11), azido-thiol (Compound 9, FIG. 11) and cysteine (Compound 10, FIG. 11), which contain unprotected amine, carboxylic acid, azide, and amino acid moieties, respectively. These TEC reactions were performed in solvents in which the reactants have good solubility (FIG. 11). In the case of the reaction with cysteine, water was added as co-solvent to obtain the desired solubility and to evaluate the effectiveness of TEC reactions in environmental friendly and biologically compatible conditions. In all cases, the reactions proceeded efficiently to give the desired adducts, Compound 4, Compound 11, Compound 12, and Compound 13 (FIG. 11) in near quantitative yield within minutes (Table 2). These examples illustrate the generality of TEC reactions in modifying tacrolimus and potentially other complex natural products containing terminal alkene groups.

To demonstrate the usefulness of TEC reactions for tacrolimus modification, a new FK1012 was synthesized. Previously, syntheses of FK1012 variants either involve multi-step transformations with 18% overall yields, or a single-step cross metathesis with 50% yield with a 22-hour reaction time. The FK1012 dimers generated in these ways contained different linkers to bridge two tacrolimus molecules and had comparable biological activities. Using dithiothreitol (DTT) as the linker, two equivalents of tacrolimus and one equivalent of DTT were coupled under the TEC reaction condition to produce FK1012-DT (Compound 15, FIG. 12) in one step within 15 minutes in quantitative yield (FIG. 12, Scheme (a)). The reported FK1012-EZ (Compound 16, FIG. 12; Diver et al. 1997. J. Am. Chem. Soc. 119:5106-5109), a FK1012 possessing an alkene linker, was also prepared (FIG. 12, Scheme (b)) in order to compare the activities of FK1012 with the two different linkers, Compound 15 (FIG. 12) and Compound 16 (FIG. 12), to induce protein dimerization in an inducible luciferase transcription assay (FIG. 13A). For the assay, two DNA constructs were prepared, each one encoding an FKBP12-fusion protein. One construct expresses the yeast GAL4 DNA binding domain (GAL4DBD) fused to three copies of FKBP12 and the other expresses the herpes simplex virus VP16 transactivation domain (VPAD) linked to two copies of FKBP12 (FIG. 13A). A reporter construct containing five copies of the upstream activation sequence at the promoter region for the luciferase gene was also used.

Once these DNA plasmids are introduced into cells, the expressed GAL4DBD-FKBP fusion protein is targeted to the upstream activation sequence but cannot activate luciferase expression unless FK1012 is present to recruit the expressed VPAD-FKBP protein to the luciferase gene. To test the activity of Compound 15 (FIG. 12) and Compound 16 (FIG. 12), the above plasmids were co-transfected into CHO cells 24 hours before adding 200 nM tacrolimus (Compound 1, FIG. 11), 100 nM Compound 15 (FIG. 12), 100 nM Compound 16 (FIG. 12), or no drug. The cells were incubated for 10 hours before being harvested and subjected to the luciferase assay. A six-fold to ten-fold induction of luciferase (compared to the no drug control) occurred only when 15 (FIG. 12) or 16 (FIG. 12) was added (FIG. 13B). Induction was not observed when the monomer tacrolimus (Compound 1) was added. These results clearly demonstrate that Compound 15 (FIG. 12), the much more efficiently synthesized FK1012-DT, is biologically active at a level comparable or better than those of previously reported analogs.

Figure 28:
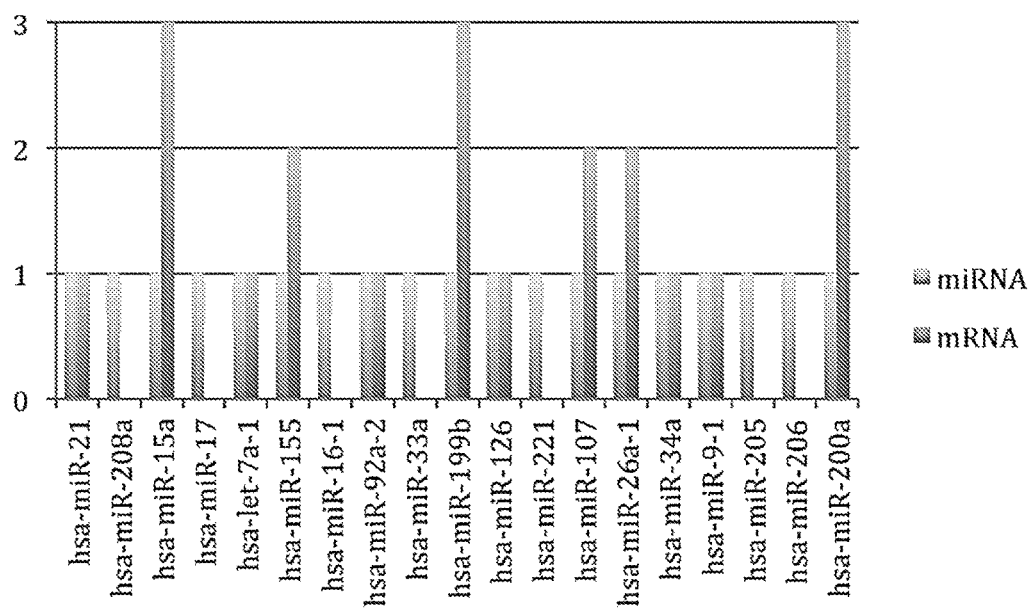
FIG. 28. BLAST analysis of 14-mer pre-miRNA targeting sequences. Sequences were obtained from the miRBase and shosen from the loop region of each pre-miRNA. The BLAST was done from the NCBI website.

Turning now to FIGS. 28-39, in which synthetic schemes and compounds are remnumbered, FIG. 28 shows that a 14-mer RNA recognition sequence is sufficient for targeting a unique pre-miRNA. To evaluate whether the 14-mer pre-miRNA recognition module is sufficient to recognize a chosen pre-miRNA, we performed a BLAST analysis using 14-mer pre-miRNA hairpin-loop sequences chosen from several reported miRNAs associated with human diseases. (Ardekani et al., Avicenna J. Med. Biotech. 2:161-179 (2010); van Rooji et al., Circ. Res. 110:495-507 (2012)) Among all of the tested pre-miRNA sequences, only the intended pre-miRNA and none of the other pre-miRNAs contains each corresponding input sequence (FIG. 28). Although many of these sequences also exist in mRNAs, the unique bi-modular design, which exerts inhibitory effects through Dicer enzymatic inactivation instead of steric interference, decreases off-site targeting and limits off-site biological effects.

Only the bi-modular regulator, but neither "Dicer inhibition module" nor "pre-miRNA recognition module" alone, inhibits Dicer-mediated miRNA maturation. We synthesized three Dicer inhibition modules (FIG. 29(A), Compounds 1-3), each of which is a reported RNase III inhibitor with IC$_{50}$>500 µM) (Parkers et al., J. Med. Chem. 46:1153-1164 (2003)) that were subsequently linked to azido-MOs with sequences complementary to the loop of human pre-miR-21 (14-mer, 15-mer, and 16-mer, custom synthesized by Gene- Tools, Philomath, Oreg.) through copper-catalyzed click chemistry (Kolb et al., *Angew. Chem.* 40:2004-2021 (2004)) to give bi-modular regulators (FIG. 29(A), Compounds 4-6). Using the click chemistry in the synthesis allows different pre-miRNA recognition modules designed for other miR-NAs to be easily linked to the optimized Dicer inhibition modules to generate new regulators. To optimize the distance between the Dicer inhibition module and the pre-miRNA recognition module, we synthesized three additional linkers (FIG. 29(B), Compounds 7-9), ranging from 10 to 21 atoms) to connect the two functional modules as shown for synthesizing the bi-modular Compound 10 (FIG. 29(B)). All synthesized molecules were purified by HPLC or silica gel chromatography and fully characterized before biological assays. These synthetic routes enable one to generate new bi-modular regulators for other miRNAs.

Figure 29A:
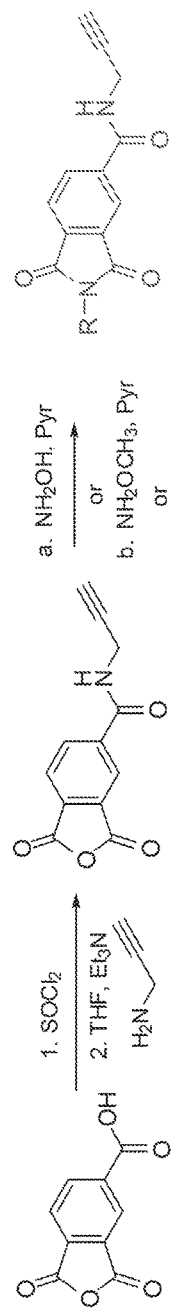
FIG. 29. (A) Synthetic scheme of Dicer inhibition modules and bi-modular regulators. (B) Synthesis of bi-modular regulators with other likers. (C) Chemical stability analysis of the bi-modular regulator.
Figure 29B:
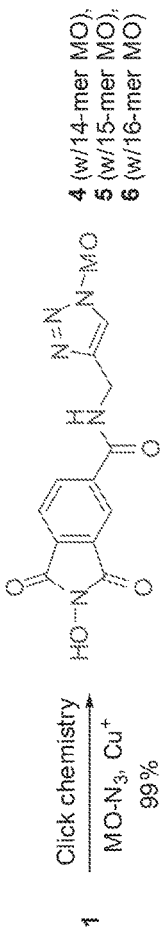
Figure 29B:
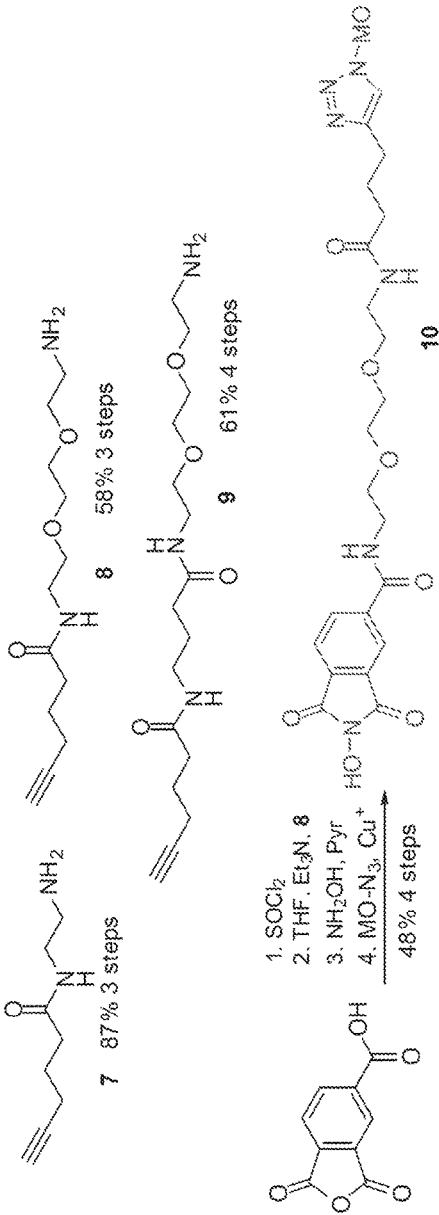
Figure 29C:
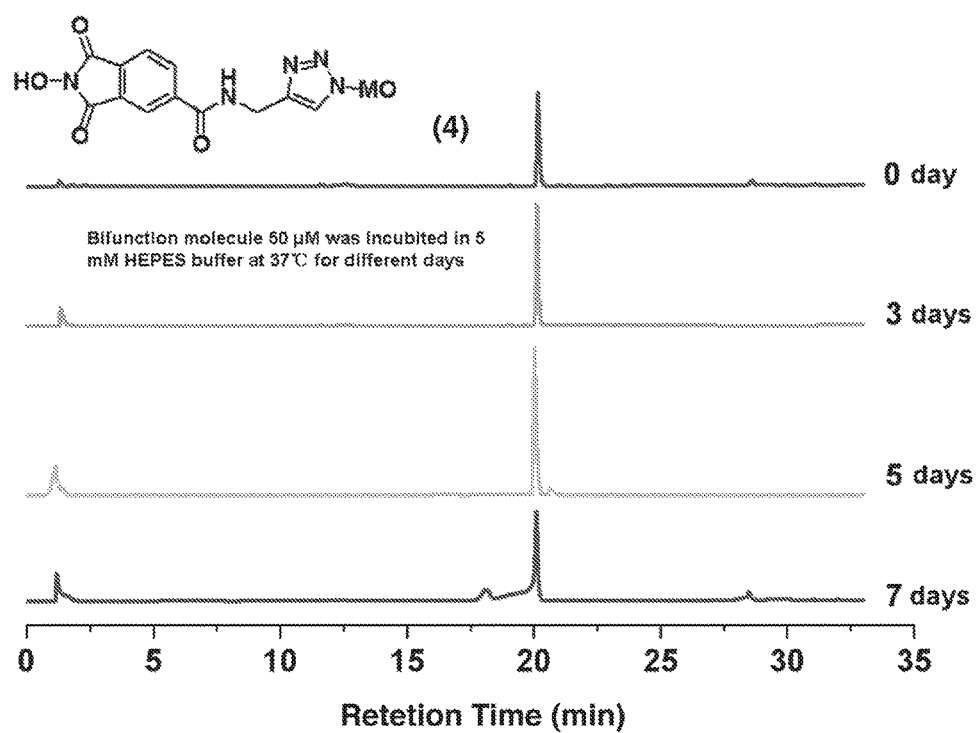
Figure 31:
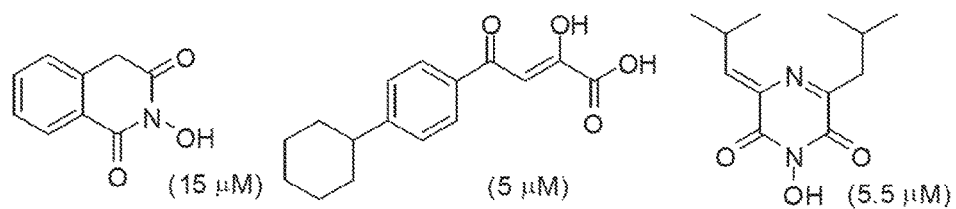
FIG. 31. Alternative Dicer inhibition modules and their reported $IC_{50}$.

For the preliminary study of the stability of the bi-modular molecule, Compound 4 (FIG. 29(A)) was incubated in HEPES buffer at 37° C. for up to seven days and then analyzed by HPLC. The synthesized bi-modular regulator is chemically stable over the tested period since the peak corresponding to Compound 4 in HPLC chromatogram did not change after the incubation (FIG. 29(C)).

To monitor the Dicer-mediated miRNA maturation process, we established a cell-free system that includes the recombinant human Dicer proteins (Genlantis, San Diego, Calif.) and $^{32}$P-labeled pre-miRNA produced by in vitro transcription using T7 RNA polymerase. The processing of pre-miRNAs (~70 nts) into short mature miRNA (~22 bps) by Dicer was examined using 16% denaturing polyacrylamide gel electrophoresis as described in MacRae et al., *Science* 311:195-198 (2006) (FIG. 30). None of the synthesized Dicer inhibition module compounds (FIG. 29 Compounds 1 to 3, up to 1 mM) can inhibit the cleavage, except FIG. 29 Compound 3 showed very minor inhibition at 1 mM (FIGS. 30(A) and (B)). 14-mer MO alone did not block cleavage at all while each of the 15-mer and 16-mer MO, alone, showed some small degree of inhibition (FIG. 30(A)). In contrast, the bi-modular regulator with the 14-mer MO (FIG. 29, Compound 4) was able to completely block the process at 10 µM and above (FIG. 30(B)), which indicated that the bi-modular design improved the potency of the Dicer inhibition module at least 100-fold. Unexpectedly, Compound 10 (FIG. 29(B)), the bi-modular regulator with longer flexible linker, showed greater inhibition than the inhibition module alone (FIG. 29, Compound 1), although it exhibited less inhibition than Compound 4 (FIG. 29). Moreover, the bi-modular regulator (Compound 4, FIG. 29) showed comparable activity compared to the 25-mer MO at the same concentration.

Figure 40:
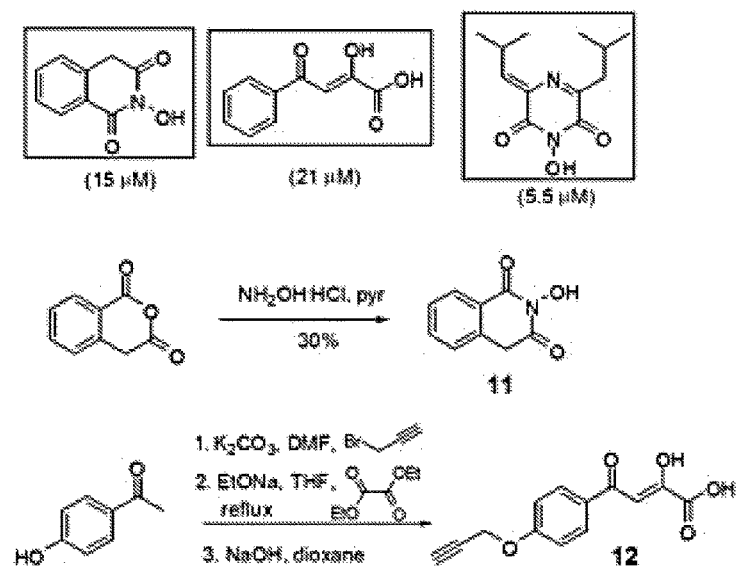
FIG. 40. Synthesis of alternative Dicer inhibition modules.
Figure 41:
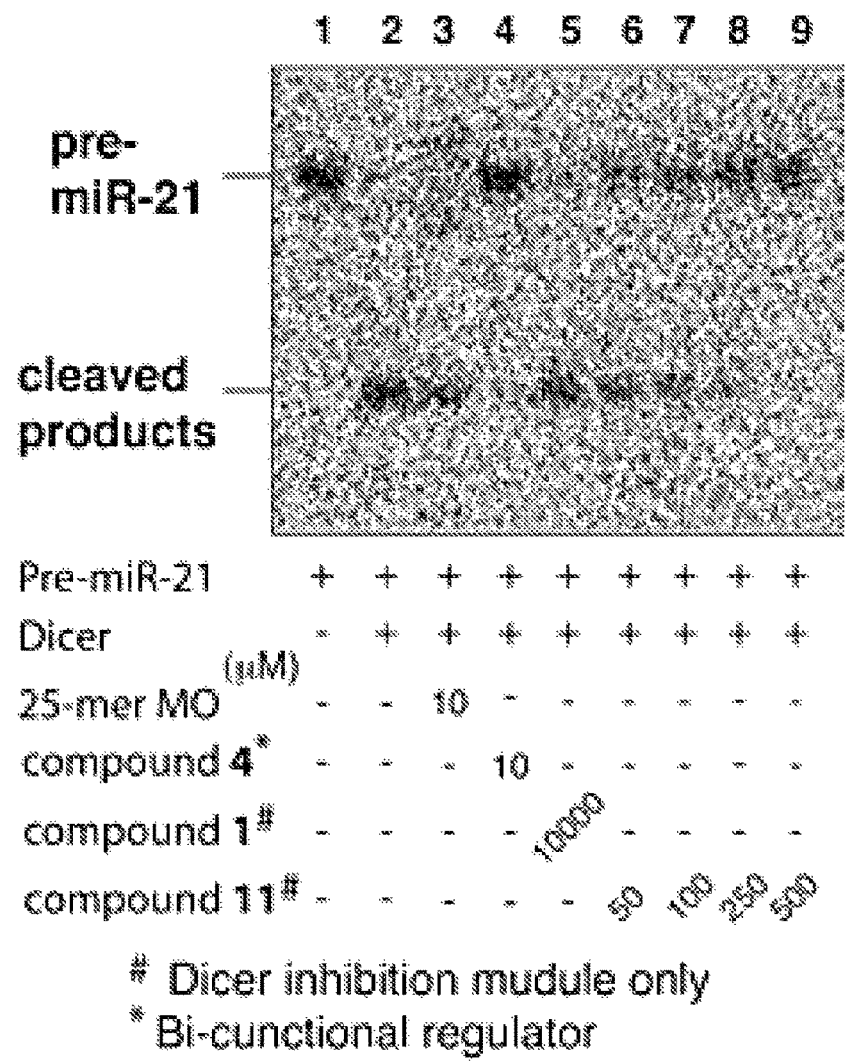
FIG. 41. Dicer-mediated pre-miRNA cleavage assay. Compound 1 and Compound 11: Dicer inhibition module only. Compound 4: Bi-modular regulator.

In some embodiments, an N-substituted phthalimide (e.g., —OH, —OMe, —NH2) can be used as a Dicer inhibition module. As noted above, N-substituted phthalimides inhibit RNase III family enzymes by presenting three oxygen/nitrogen atoms at positions and distances that can coordinate and/or sequester the two divalent metal ions ($Mg^{2+}$ in Dicer) in the active site, although rather poorly ($IC_{50}$>500 µM). From the data shown in FIG. 30B, the bi-modular molecules (Compound 4, FIG. 29) has significantly improved inhibitory activity compared to N-hydroxyphthalimide alone (Compound 1, FIG. 29). One can, however, choose a more potent inhibition module to incorporate into the bi-modular regulator and produce a more potent regulator, which can possess more inhibitory activity than current antisense molecules. For example, using more potent RNase III inhibitors (e.g., N-hydroxyimides, diketobutanoates, or flutimides, FIG. 31) may give more potent (low nM) bi-modular regulators. These alternative inhibition modules may be synthesized following reported procedures (see, e.g., Parkers et al., *J. Med. Chem.* 46:1153-1164 (2003)), and then coupled to the linkers and 14-mer MO. For example, Compound 11 (FIG. 40), at 50 µM showed better inhibition in miR-21 processing than Compound 1 (FIG. 29) at 10 mM, which suggests that Compound 11 (FIG. 40) is at least 200-fold more potent (FIG. 41). Moreover, the bi-modular regulator Compound 4 (FIG. 29) exhibited complete inhibition at 10 µM, reflecting an increase in the activity of a weak inhibition module of over 1,000-fold.

Figure 32:
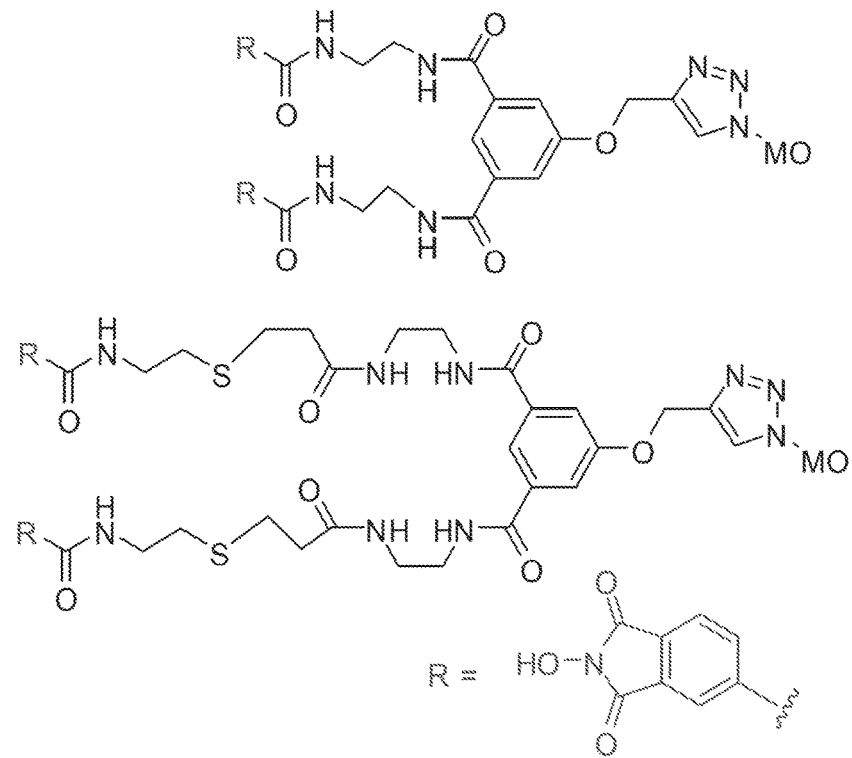
FIG. 32. Additional alternative Dicer inhibition modules with linkers of varying lengths.
Figure 33:
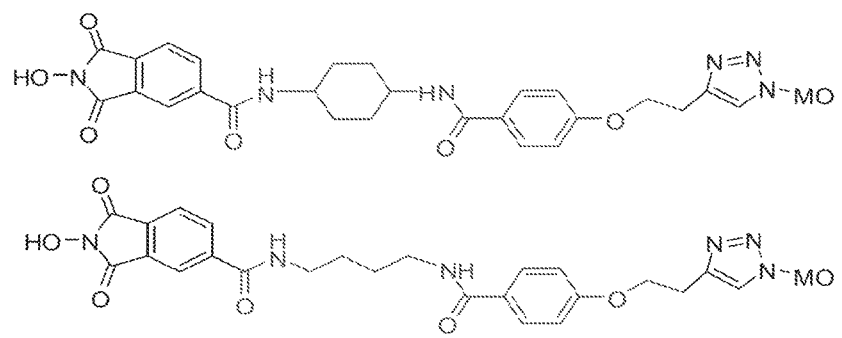
FIG. 33. Exemplary bi-modular regulators with exemplary rigid linkers.
Figure 34:
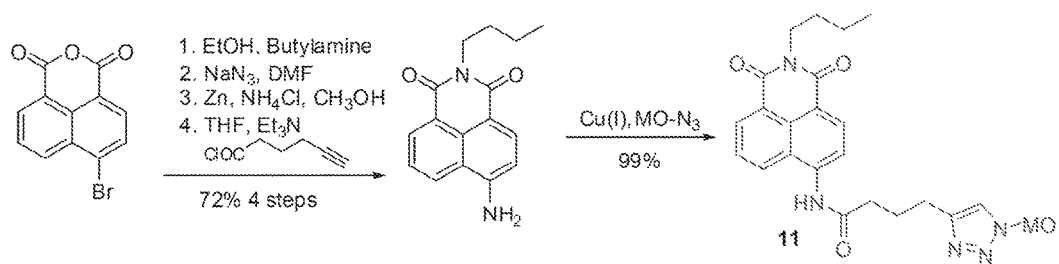
FIG. 34. Synthesis of a model bi-modular fluorescent probe.
Figure 35:
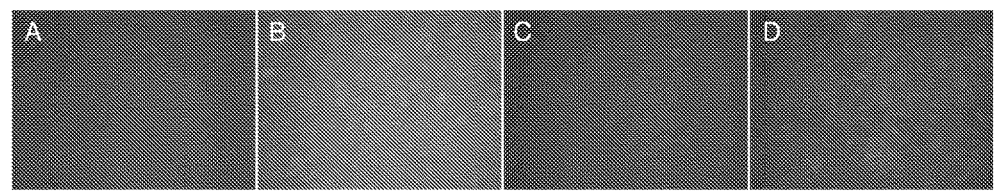
FIG. 35. Cell uptake of the model fluorescent bi-modualr molecule. HeLa cells were incubated 72 hours with (A) none, (B) fluorophore only without MO, (C) bi-modular compound 11 from FIG. 34, or (D) bi-modular compound 11 from FIG. 34 with the Endo-Porter.

Also, as noted above, there are two active sites on Dicer, each of which can cleave one strand of the pre-miRNA hairpin duplex. (MacRae et al., *Science* 311:195-198 (2006)). A Dicer inhibition module with two inhibitors can inhibit these two active sites simultaneously and may give a higher inhibition activity. We have designed bi-modular regulators with the described enhanced inhibition module containing two units of Compound 1 (FIG. 29) with different linker lengths (FIG. 32). The inhibitory activity of these new molecules can be greater than the inhibitory activity of either compound 4 (FIG. 29) alone (which contains only one inhibitor) or 25-mer MO. Also as noted above, the distance from the Dicer active site to the far end of the single strand hairpin loop is approximately 30 Å, which is covered by the lengths of linkers reflected in FIGS. 29(A) and (B). The shortest linker is long enough to give an active bi-modular miR-21 regulator (Compound 4, FIG. 29) and the length of linkers can affect the inhibitory activity of a bi-modular regulator (FIG. 30(B)). FIG. 33 illustrates bi-modular regulators with containing N-hydroxyphthalimide and the 14-mer MO with four different linkers (including compound 4, FIG. 29, and compound 10, FIG. 29). The length and/or structure of the linker can affect activity of the bi-modular compound. For example, a very flexible linker may exhibit entropic penalty after binding, as indicated by the reduced activity of Compound 10 (FIG. 29) when compared to Compound 4 (FIG. 29) in the data presented in FIG. 30(B).

We also synthesized a fluorescent MO probe to study cell uptake. The 25-mer MO cannot pass through a cell membrane and requires special reagent for intracellular delivery. A model fluorescent bi-modular molecule (compound 11, FIG. 34) that includes a 14-mer MO did not pass through the cell membrane, as observed under microscope after wash by incubating it (10 µM) with HeLa cells (FIG. 35(C)). However, with the help of an MO delivery agent, Endo-Porter (GeneTools, LLC, Philomath, Oreg.), the fluorescent MO molecule, incubated with HeLa or CHO cells at 10 µM) can be delivered into cells up to a level that is observable under microscope (FIG. 35(D)).

To enable more efficient intracellular delivery, one can use the nanoporous particle-supported lipid bilayer method. This reported method combines the advantages of liposomes and nanoparticles for intracellular delivery and has been shown to successfully deliver cargo molecules such as, for example, small molecules, siRNAs, proteins, and quantum dots into cells within a few hours and release the cargo molecules from endosomes. (Ashley et al., *Nat. Mater.* 10:389-397 (2011)). Moreover, cell-specific targeting can be achieved through the modification of the lipid bilayer surface.

Figure 36:
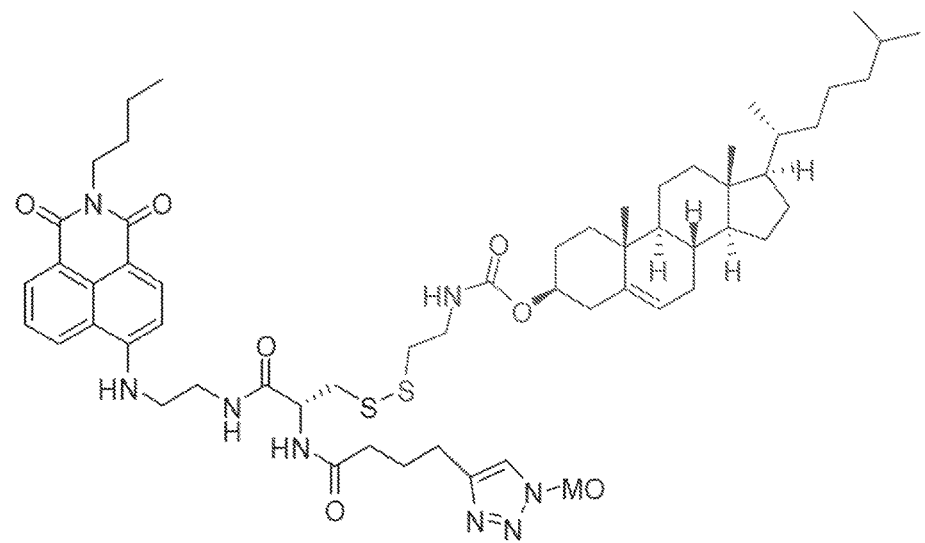
FIG. 36. Model fluorescent bi-modular probe with an exemplary cell delivery module.

Attaching a cholesterol molecule to an otherwise non-cell permeable antisense molecule can improve its uptake by cells. (He et al. *Nat. Rev. Gen.* 5:522-531 (2004)) A similar strategy can be applied to the bi-modular regulators described herein. FIG. 36 shows a chemically-modified fluorescent model bi-modular molecule (Compound 11, FIG. 34) that has been modified by attaching a cholesterol moiety as the cell delivery module. To prevent the added cholesterol moiety from interfering with the Dicer inhibition in bi-modular regulators, a cleavable disulfide linker can be used between the bi-modular molecule and the cholesterol moiety, which can be cleaved in the reducing intracellular environment.

Light-activatable and inactivatable bi-modular regulators can be synthesized by introducing a light sensitive cage group in the Dicer inhibition module and the linker. To study the effectiveness of using light to control the activity of the regulators, we first synthesized a photo-inactivatable version of Compound 4 (FIG. 29) without 14-mer MO by incorporating a light cleavable group, the 4,5-Dimethoxy-2-nitrobenzyl (DMNB) group (Callaway et al., *Proc. Natl. Acad. Sci. U.S.A.* 90:7661-7665 (1993)), into the inker (Compound 12, FIG. 37(A)). Because neither the individual Dicer inhibition module nor the pre-miRNA recognition module can, alone, block the maturation of miRNAs (FIG. 30), the cleavage of the linker connecting these two modules can inactivate the bi-modular regulators. The DMNB-containing linker can be cleaved by the 365 nm photo-irradiation starting within one minute and cleavage was near complete in 10 minutes (FIGS. 38(A) and (B)).

Figure 37A:
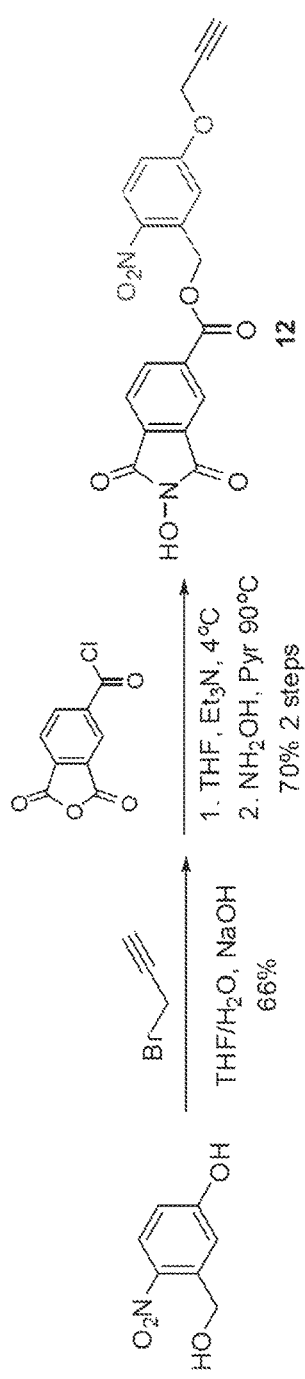
FIG. 37. Synthesis of light-controllable bi-modular miRNA regulators.
Figure 37B:
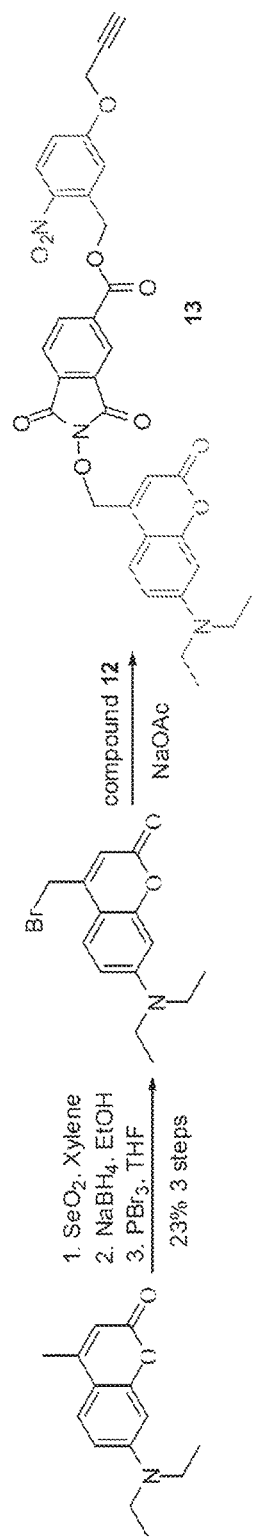
Figure 38A:
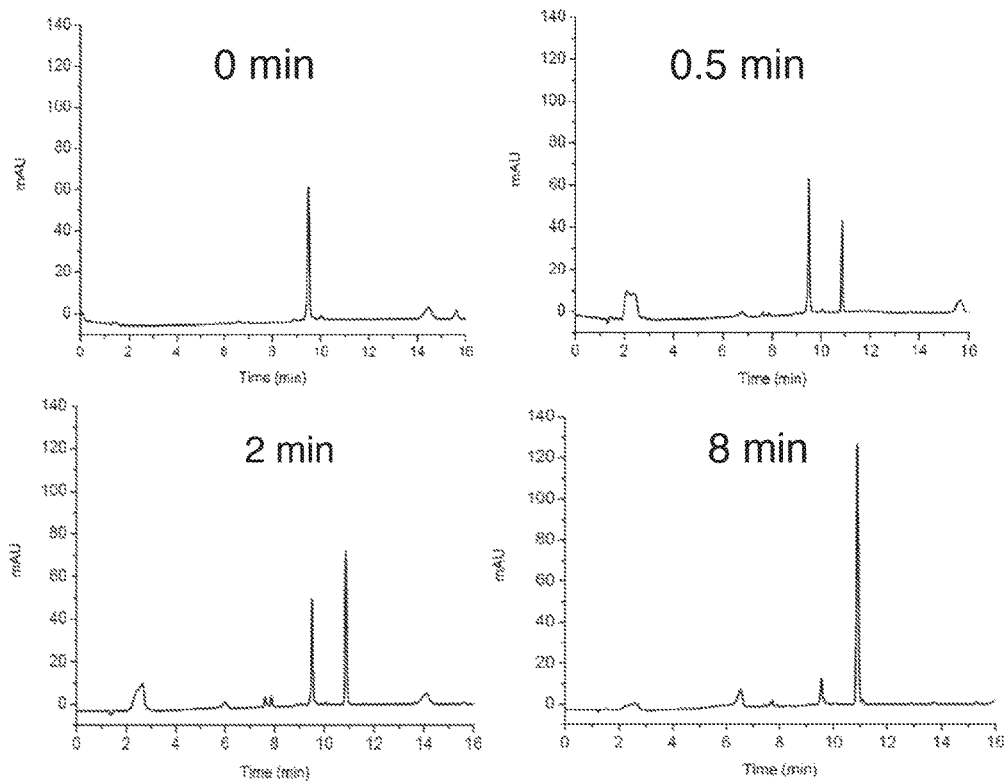
FIG. 38. Photo-cleavage of DMNB and DEACM groups. (A) Representative HPLC chromatograms of compound 12 of FIG. 37 photo-cleavage time course. (B) Ratio of uncleaved compound 12.
Figure 38B:
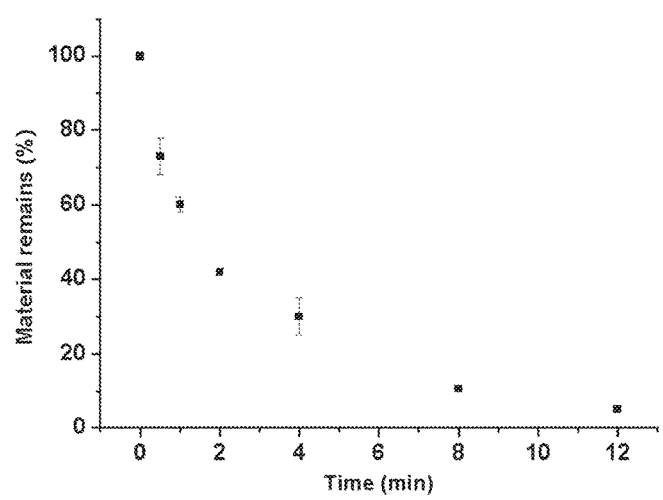
Figure 39:
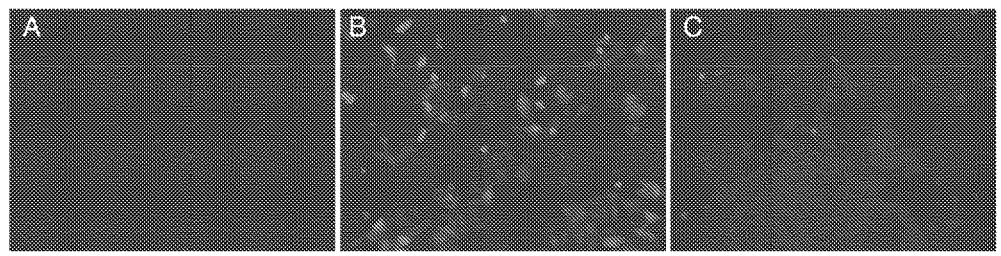
FIG. 39. EGFP reporter for miRNA-21. HeLa cells were transfected with either (a) none, (B) control EGFP, or (C) EGFP-α21 construct for 24 hours.

We also synthesized another photo-controllable version of Compound 4 (FIG. 29) that can be activated by 405 nm photo-irradiation and subsequently be inactivated by 365 nm irradiation (Compound 13, FIG. 37(B)). In addition to the DMNB group in the linker, another light sensitive caging group, the (7-diethylaminocoumarin-4-yl)methyl (DEACM) group (Shembekar et al. *Biochemistry* 44:7107-7114 (2005)), which responds to 405 nm light, was used to cage the Dicer inhibition module at its N-hydroxy group. The DMNB group is known to respond poorly to 405 nm irradiation. Therefore, DEACM and DMNB in Compound 13 (FIG. 37(B)) can be uncaged independently by 405 nm and 365 nm in sequence.

We further developed an EGFP reporter construct that reflects the endogenous miR-21 level. We made a mammalian expression construct (EGFP-α21) of a CMV-actin promoter-driven EGFP where at the 3'-UTR, a completely complementary binding sequence of miR-21 was inserted into a NotI site. With the presence of miR-21, EGFP expression is inhibited. A reduction of cellular miR-21 level increases EGFP expression. A control EGFP plasmid without this miR-21 recognition site also was made, which does not respond to the level of miR-21. We have tested both constructs in HeLa cells, which is known to express miR-21. We found that EGFP was expressed at high level when the control EGFP construct was transfected (FIG. 39(B)), but the expression was significantly reduced when the EGFP-α21 construct was transfected (FIG. 39(C)).

This reporter system may be used in light-controlled miR-21 studies and also for cellular stability test of the bi-modular regulators. This reporter system also can be transfected into any mammalian cells to establish cell lines for reporting endogenous miR-21 level changes. This may be useful in order to, for example, screen for potential inhibitors and/or to perform quick preliminary experiments before more detailed analysis with other methods. This reporter system also may be adapted for studying other miRNAs by simply substituting an appropriate binding sequence for any miRNA of interest for the miR-21 recognition sequence in the model construct that we report here. The substitution of a binding sequence can be made easily via the NotI site.

In conclusion, we have developed a new, efficient thiol-ene click protocol for the facile functionalization of tacrolimus. Under mild reaction conditions, commonly used chemical handles can be conveniently installed on tacrolimus without impacting FKBP12 binding and enable the production of complex bioactive molecules (e.g. FK1012). This method provides an attractive alternative to existing approaches for the derivatization of tacrolimus. We envision that tacrolimus has the potential of serving as a general and useful installation for various biologically active small molecules or macromolecules that recruit endogenous FKBP12 to modulate the activity, binding selectivity or stability of conjugated molecules. This new and efficient tacrolimus modification method should significantly facilitate these applications. To our knowledge, this study is the first to apply the TEC reaction to natural product semi-synthesis. We expect that the scope of TEC reactions will expand beyond current applications to the semi-synthesis of structurally complex natural products.

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

In vitro Transcription.

DNA templates for the pre-miR21 were amplified using PCR, with 5' primers containing the T7 promoter sequence. The $^{32}$P-labeled pre-miR21 were produced by in vitro transcription mixing 2 µl 10× transcription reaction buffer (NEB), 2 µl 100 mM DTT, 0.5 µl RNasin™ (Promega Corp., Madison, Wis.), 4 µl of mixture of ATP, GTP and CTP (2.5 mM each), 2.4 µl 100 µM UTP, 0.2-1.0 µg template, α-$^{32}$PUTP(10 mCi/ml) and 1 µl T7-RNA polymerase. The final 20 µl reaction was incubated at 37° C. for one hour, then treated with DNase to eliminate the template. Spin columns (Ambion, Life Technologies Corp., Grand Island, N.Y.) were used to remove unincorporated free nucleotides.
Morpholino Recognition Assay 1 µM 25-nucleotide morpholino aqueous solution or a 14-nucleotide morpholino aqueous solution was prepared as 10× stock solution. 5.5 µl of the in vivo-transcribed pre-miR21 were incubated in 1.5 µl 10 mM ATP, 0.75 µl 50 mM MgCl$_2$, and 6 µl Dicer reaction buffer, either with/without the 25-nucleotide morpholino or the 14-nucleotide morpholino under 25° C. for one hour. One unit of recombinant human Dicer (Genlantis, Inc., San Diego, Calif.) was added subsequently and the samples were incubated under 37° C. for six hours. The reactions were stopped by adding 2 µl of Dicer stop solution.

The pre-miR2l and its product miR-21 were checked by using 15% TBE-Urea polyacrylamide gel. The signals were obtained by exposing in KODAK Storage Phosphor Screen and visualized by BIO-RAD Molecular Imager.

Results are shown in FIG. 8.
miR-21 Maturation Assay

The samples (Table 3) were incubated at room temperature for one hour without addition of Dicer (Genlantis, Inc., San Diego, Calif.). Then the reaction mixtures were incubated at 37° C. for three hours. The samples were checked with 15% TBE-Urea polyacrylamide gel and were visualized on a phosphor imager (Bio-Rad Laboratories, Inc., Hercules, Calif.).

TABLE 3

| Lane # | pre-miR-21* | Dicer‡ (units) | Regulator |
|---|---|---|---|
| 1 | 5.5 μl | 0 | none |
| 2 | 5.5 μl | 1 | none |
| 3 | 5.5 μl | 1 | 100 nM 25-nucleotide morpholino |
| 4 | 5.5 μl | 1 | 1 μM 14-nucleotide morpholino |
| 5 | 5.5 μl | 1 | 100 nM 14-nucleotide morpholino |
| 6 | 5.5 μl | 1 | 1 μM Dicer inhibitor |
| 7 | 5.5 μl | 1 | 100 nM Dicer inhibitor |
| 8 | 5.5 μl | 1 | 1 μM bi-functional miR-21 regulator |
| 9 | 5.5 μl | 1 | 100 nM bi-functional miR-21 regulator |

*transcribed in vitro as described above
Results are shown in FIG. 9.

Example 2

Photocleaving Assay

Figure 10A:
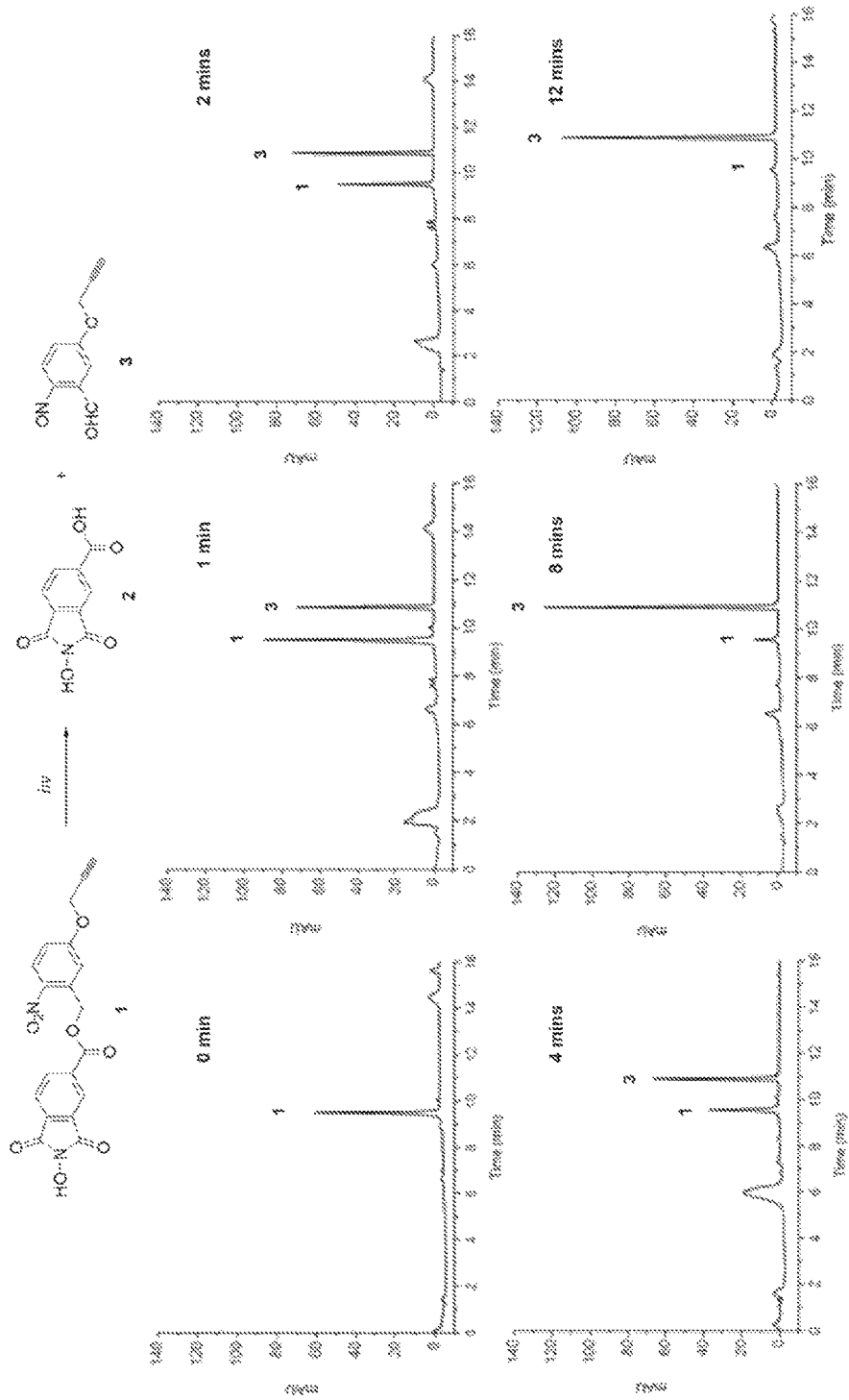
FIG. 10. Test the photocleavage efficiency of synthesized photo-responsive inhibitor-linker moiety. The reducing of the starting compound and the increasing of the cleavage product was followed by HPLC.
Figure 10B:
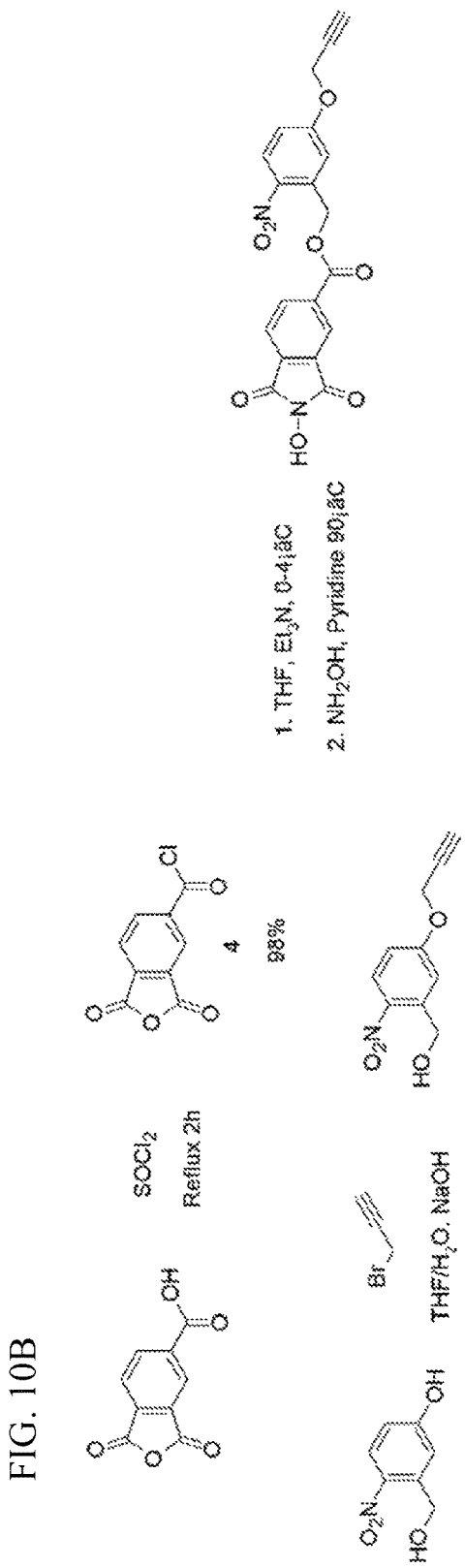

A 10 μM solution of Compound 1 with 95% ethanol was prepared as shown in FIG. 10B. 30 μL aliquots of the Compound 1 solution was placed in well of a 96-well plate, followed by irradiation for 0 minutes, one minute, two minutes, four minutes, eight minutes, or 12 minutes with an Axio Observer D1 microscope on blue channel full power (Carl Zeiss Microscopy, Jena, Germany). The irradiated samples were subjected to HPLC using a Dionex Ultimate 3000 (Thermo Fisher Scientific, Inc., Sunnyvale, Calif.).

Results are shown in FIG. 10.

Example 3

Chemicals and Instruments:

Bulk solvents were obtained from EMD Millipore (Merck KGaA, Darmstadt, Germany). Cysteamine, 3-thiopropanoic acid, Cysteine, Dithiothreitol, 5-hexynoic acid, N-Ethyl-N'-(3-dimethylaminopropyl)carbodiimide hydrochloride (EDCI), Et$_3$N, 1-Hydroxybenzotriazole hydrate (HOBt), 3-Aminopropanol, di-tert-butyl dicarbonate (Boc$_2$O), 4-(Dimethylamino)pyridine (DMAP), p-Toluenesulfonyl chloride (TsCl), triethylsilane, NaN$_3$ and 2,2-Dimethoxy-2-phenylacetophenone (DPAP) were obtained from Sigma-Aldrich (St. Louis, Mo.) and Alfa-Aesar (Ward Hill, Mass.) and were used directly without further purification. Other chemicals are commercially available. Boc-cysteamine was synthesized from Cysteamine following the general procedure. 3-(tritylthio)propinoic acid was synthesized following the reported literature (Sharma et al. 2008. *Langmuir*, 2008, 24:13581-13590). NMR spectra were recorded on a Bruker instrument (300 MHz). Mass and NMR spectra for new compounds were recorded at the Mass Spectrometry and NMR Facilities, Department of Chemistry and Chemical Biology, University of New Mexico.

Synthesis of Compounds:

Synthesis of Compound 17

3-Aminopropanol (7.0 g, 92 mmol) dissolved in methanol (100 mL) was successively treated with di-tert-butyl dicarbonate (22.0 g, 101.2 mmol) and di-iso-propylethylamine (32 mL, 184 mmol) stir overnight at room temperature. After removal of the solvent under reduced pressure, the product was dissolved in DCM (100 mL). The organic layer was washed with 10% citric acid (X2). The aqueous layers were extracted with DCM. The combined organic layers were dried over sodium sulfate. Removal of the solvent under vacuum gave Compound 17 as colorless viscous oil (17.5 g, yield: 99%). $^1$H NMR (CDCl$_3$, 300 MHz): 4.78 (bs, 1H), 3.67-3.63 (t, J=11.4 Hz, 2H), 3.29-3.25 (t, J=12.3 Hz, 2H), 1.69-1.63 (m, 2H), 1.44 (s, 9H). $^{13}$C NMR (CDCl$_3$, 300 MHz): 157.50, 79.64, 59.26, 36.97, 32.89, 28.36.

Figure 15A:
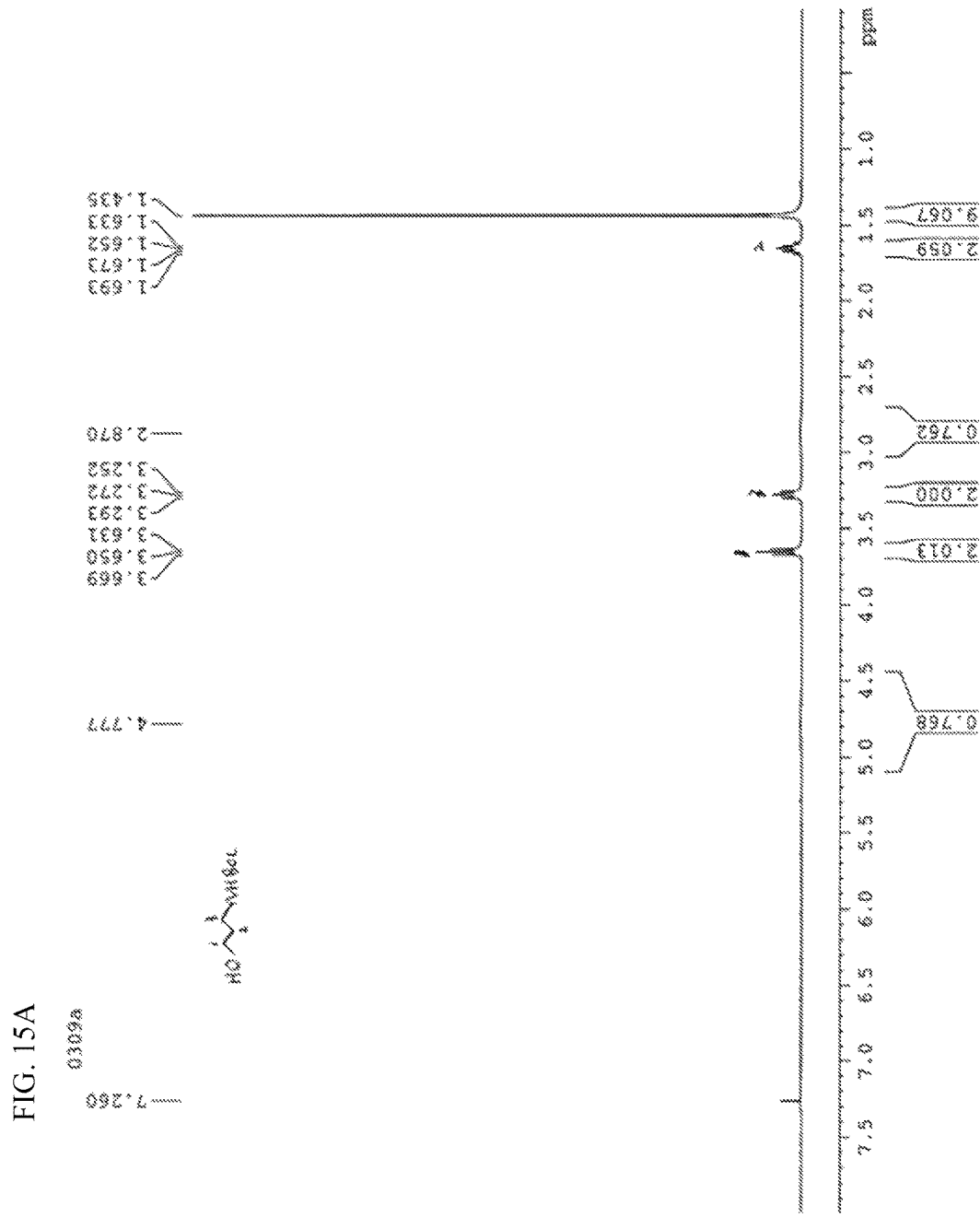
FIG. 15. (A) $^1$H NMR of compound 17; (B) $^{13}$C NMR of compound 17.
Figure 15B:
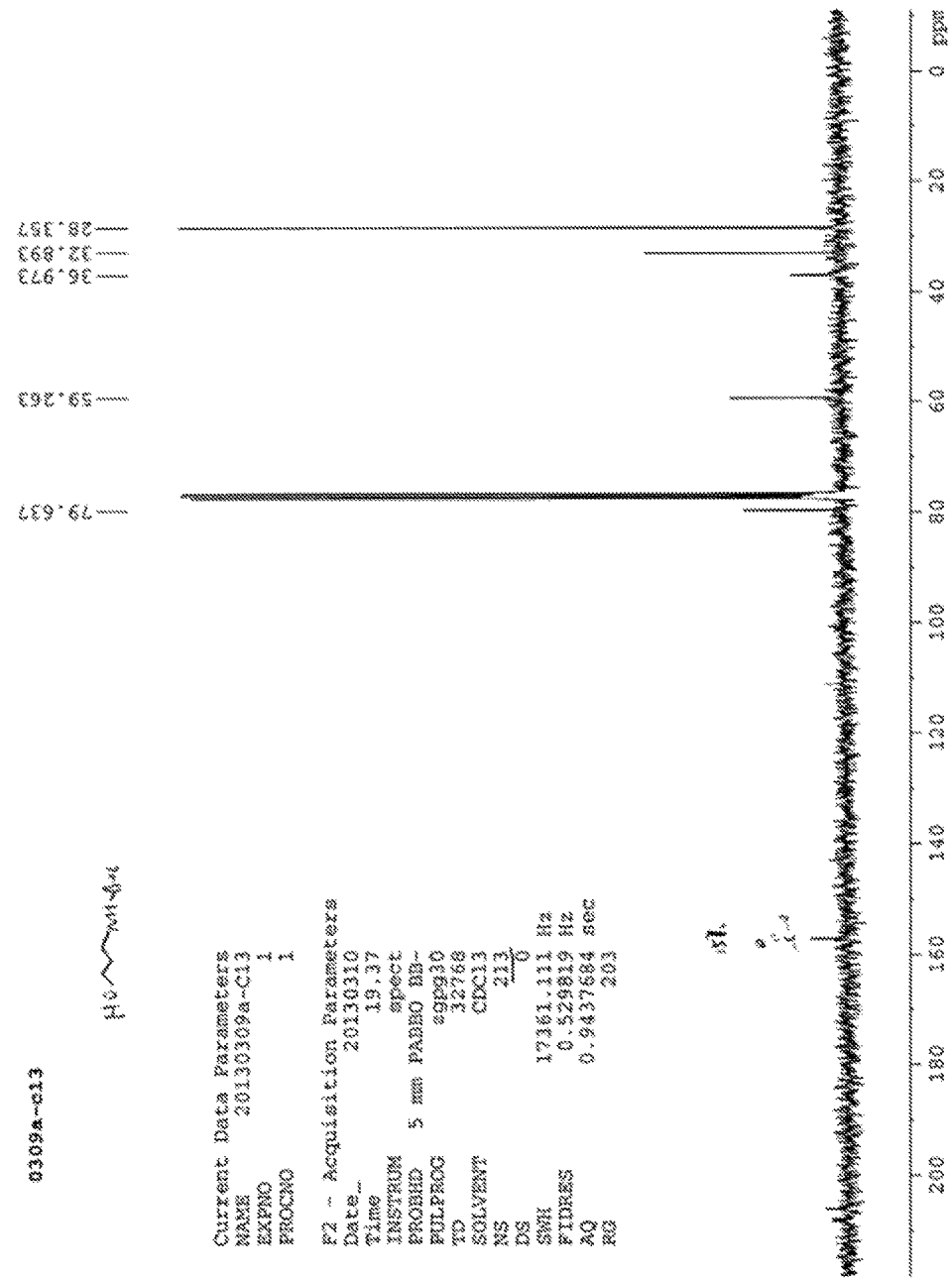

$^1$H NMR and $^{13}$C NMR are shown in FIG. 15.

Synthesis of Compound 18

Compound 17 (3.50 g, 20 mmol), Et$_3$N (2.02 g, 20 mmol) and DMAP (0.244 g, 2 mmol) were stirred in DCM about five minutes. TsCl (4.00 g, 21 mmol) was added and stirred further two hours at room temperature. Colorless viscous solid was obtained after purification by silica gel column chromatography using hexane/ethyl acetate (v/v=2:1) as an eluting solvent (R$_f$=0.72). Yield: 96%. $^1$H NMR (CDCl$_3$, 300 MHz): 7.79-7.77 (d, J=8.4 Hz, 2H), 7.36-7.33 (d, J=8.1 Hz, 2H), 4.61 (bs, 1H), 4.09-4.05 (t, J=12.0 Hz, 2H), 3.15 (s, 2H), 2.44 (s, 3H), 1.87-1.79 (m, 2H), 1.41 (s, 9H). $^{13}$C NMR (CDCl$_3$, 300 MHz): 155.87, 144.91, 129.92, 127.88, 79.36, 68.00, 36.82, 29.26, 28.35, 21.64.

Figure 16A:
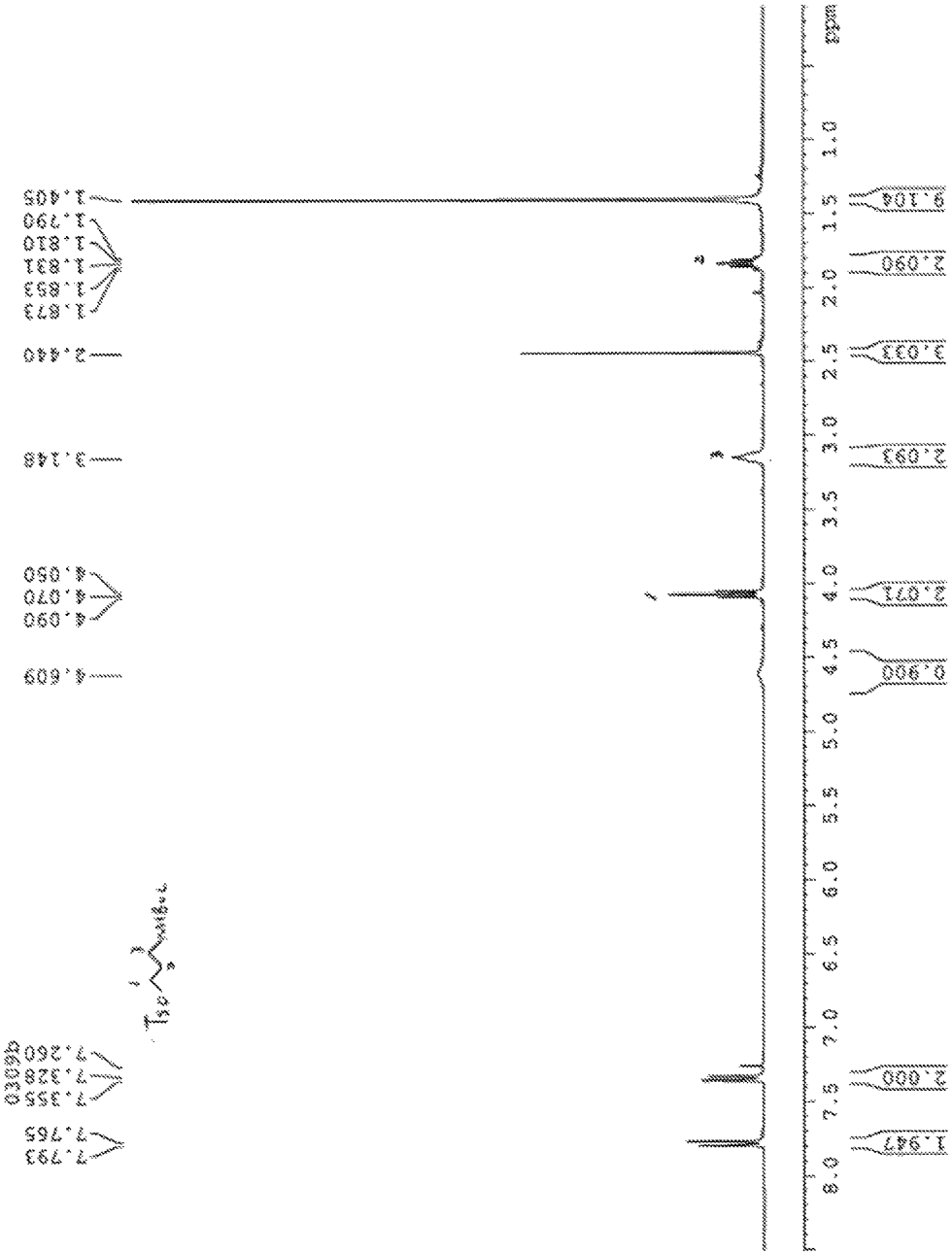
FIG. 16. (A) $^1$H NMR of compound 18; (B) $^{13}$C NMR of compound 18.
Figure 16B:
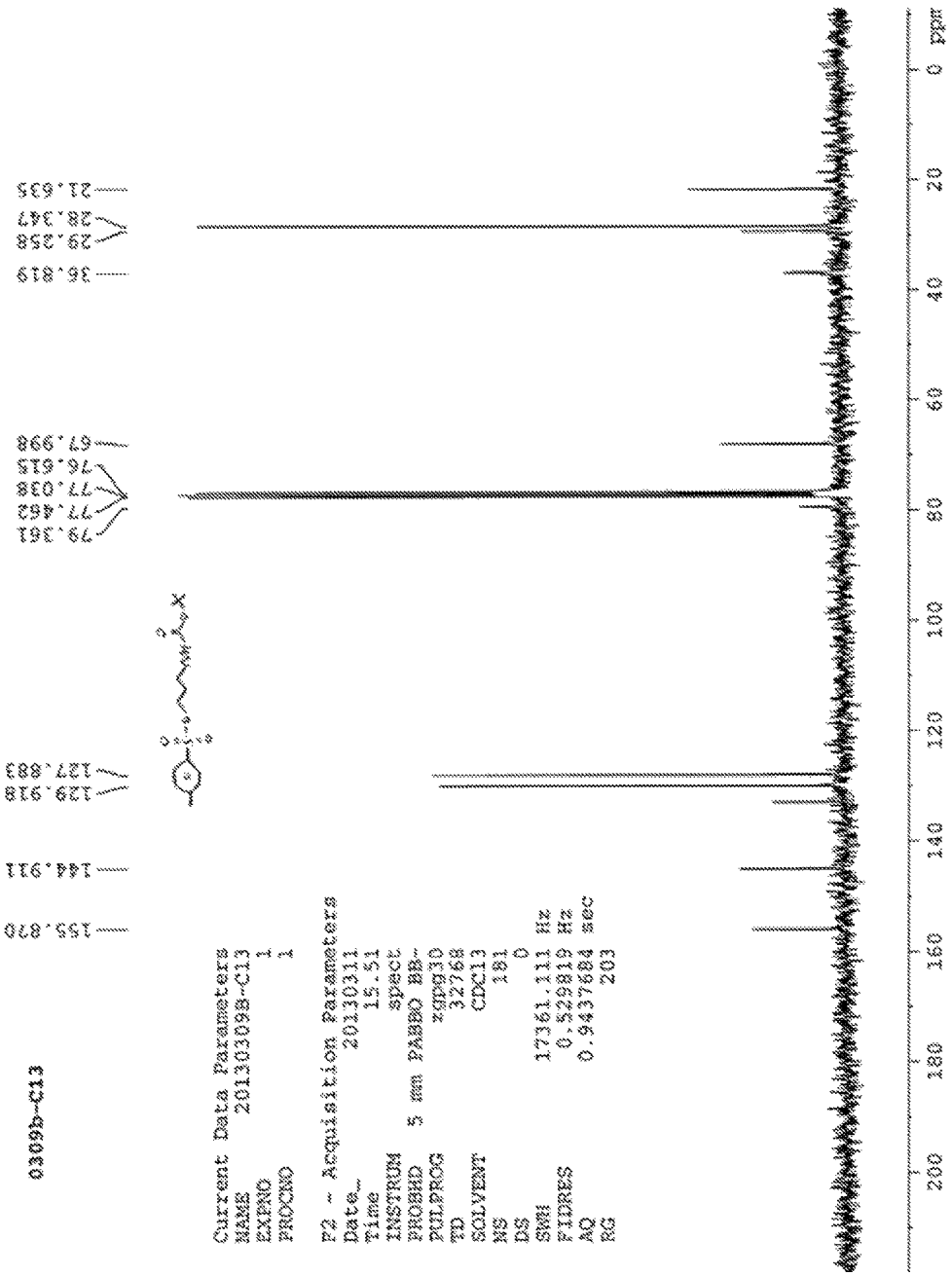

$^1$H NMR and $^{13}$C NMR are shown in FIG. 16.

Synthesis of Compound 19

Compound 18 (3.29 g, 10 mmol) and NaN$_3$ (3.30 g, 30 mmol) were stirred in THF/H$_2$O (v/v=5:1) for two hours. The mixture was extracted with ethyl acetate. The organic layers were combined, washed three times with NaHCO$_3$ and brine, and subsequently dried with anhydrous Na$_2$SO$_4$.

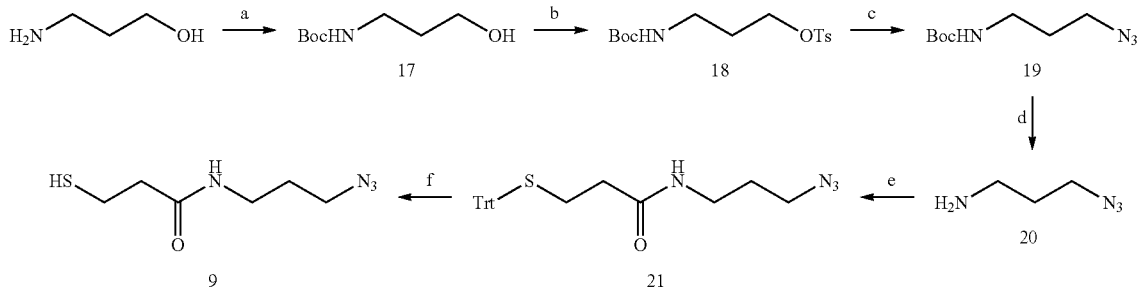

Synthetic scheme: a) (Boc)$_2$O, DIPEA, MeOH (99%); b) TsCl, DMAP, Et$_3$N, DCM (96%); c) NaN$_3$, DMF, rt, 13 h (89%); d) TFA/DCM, rt, 1 h (99%); e) HATU, DIPEA, DCM, rt overnight (92%); f) TFA/DCM(v/v = 2:8), Et$_3$SiH, rt, 1 h (94%).

Colorless viscous solid was obtained after the solvent was removed under reduced pressure. Yield: 89%. $^1$H NMR (CDCl$_3$, 300 MHz): 4.66 (bs, 1H), 3.37-3.33 (t, J=13.2 Hz, 2H), 3.22-3.18 (t, J=12.9 Hz, 2H), 1.80-1.71 (m, 2H), 1.43 (s, 9H). $^{13}$C NMR (CDCl$_3$, 300 MHz): 155.94, 79.42, 49.11, 38.10, 29.29, 28.37. TOF-HRMS (m/z) found (calcd.) for C$_8$H$_{16}$N$_4$OS (M): [M+Na]$^+$, 223.1171 (223.1171).

Figure 17A:
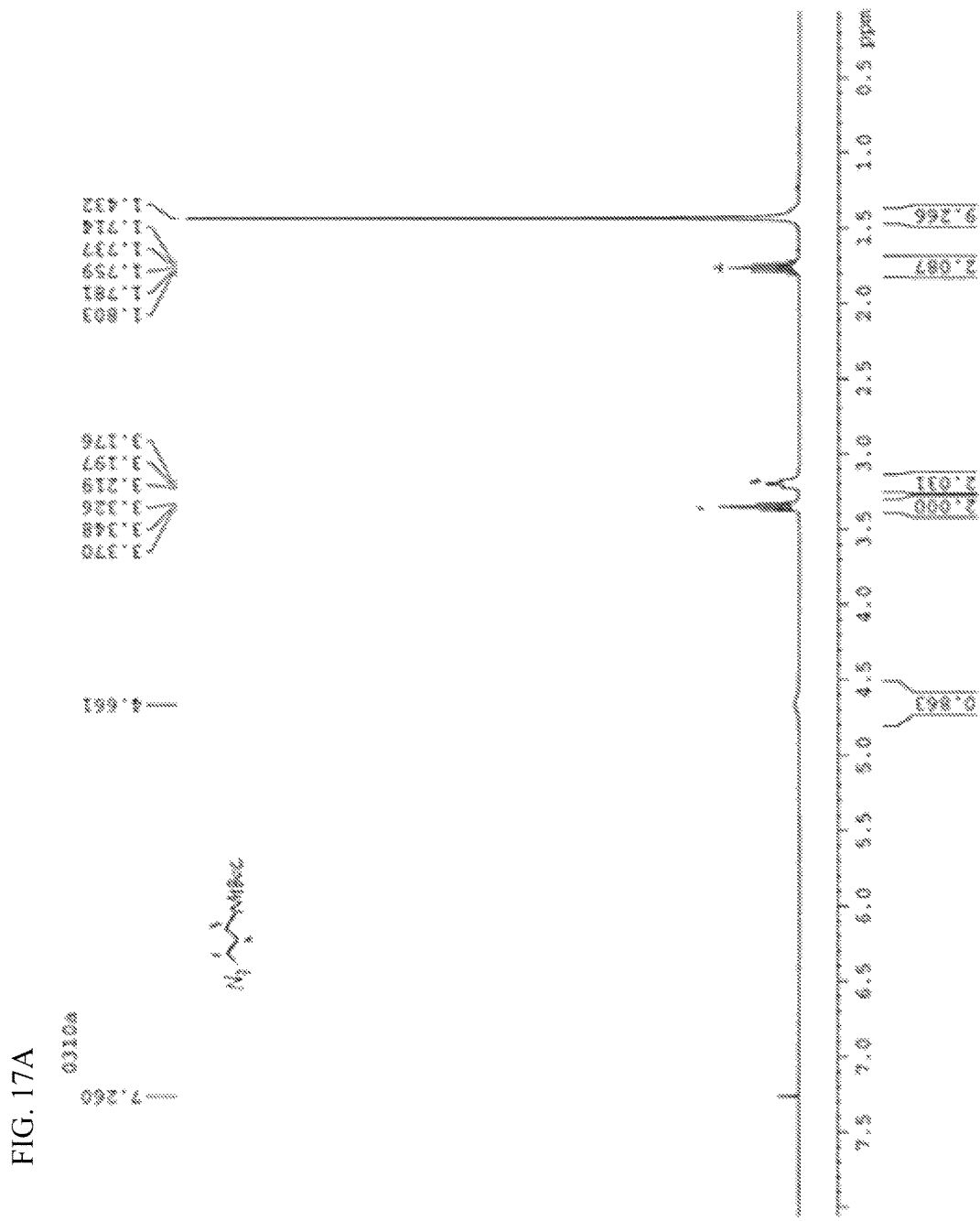
FIG. 17. (A) $^1$H NMR of compound 19; (B) $^{13}$C NMR of compound 19; (C) HRMS of compound 19.
Figure 17B:
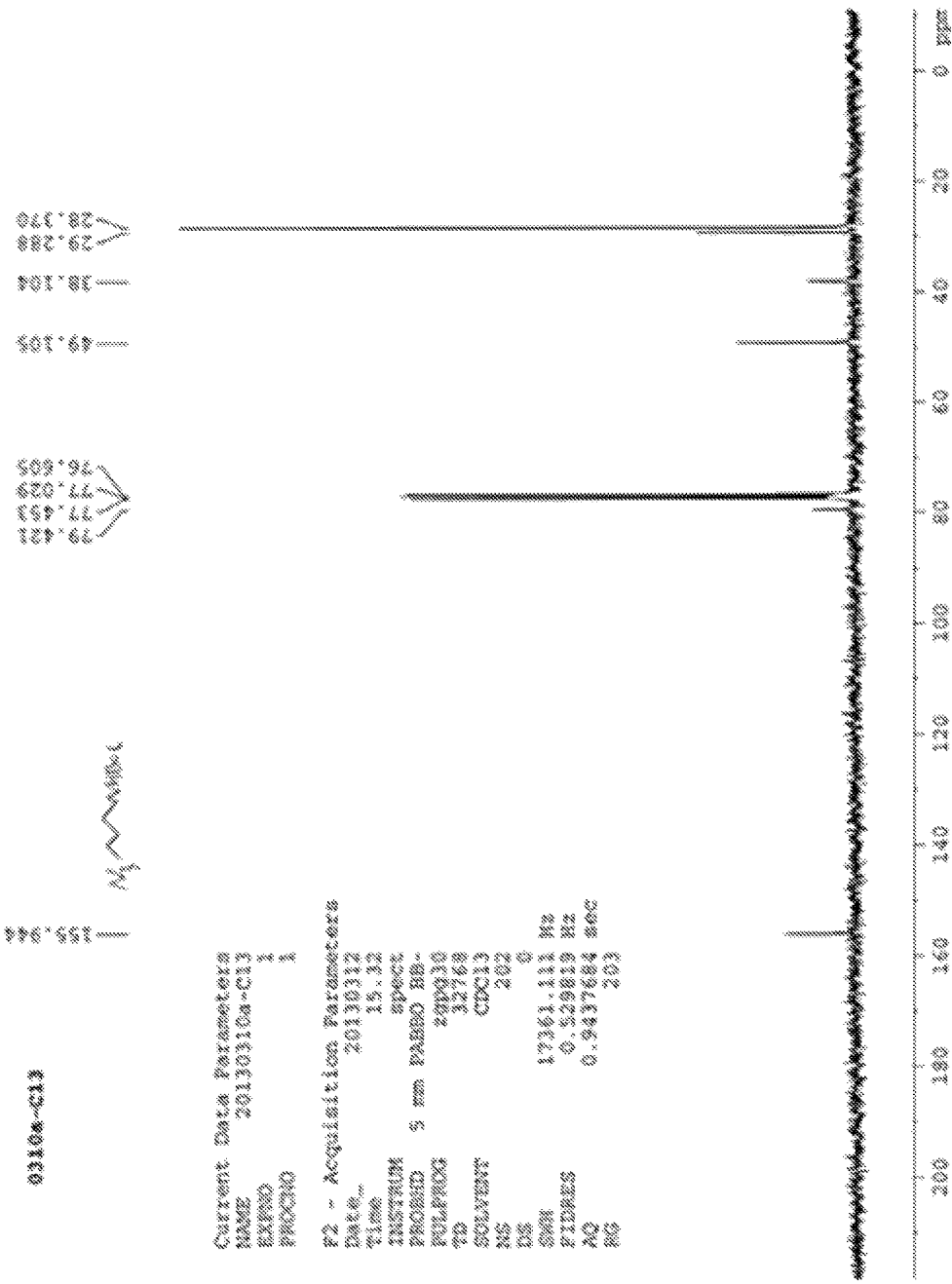
Figure 17C:
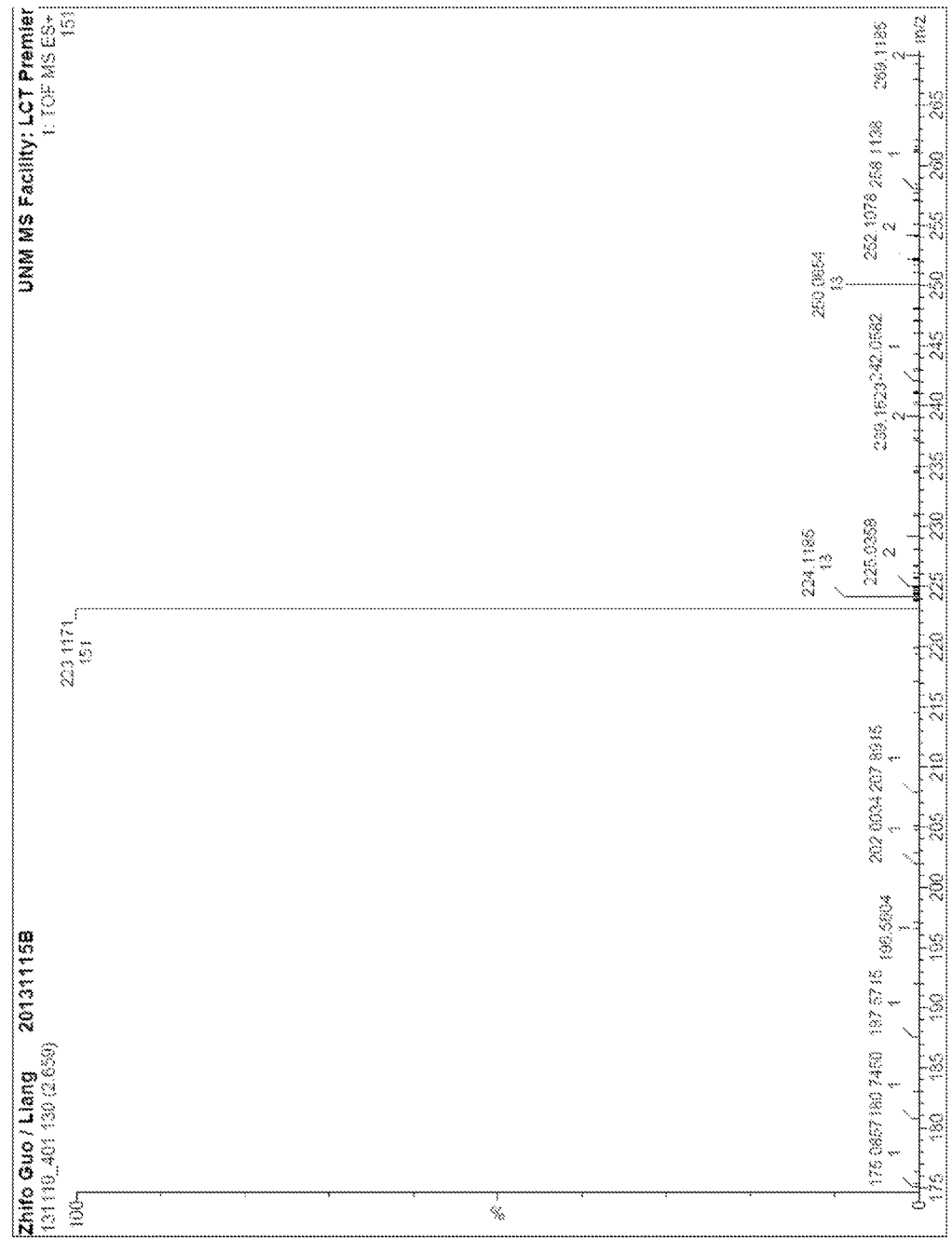

$^1$H NMR, $^{13}$C NMR, and HRMS are shown in FIG. 17.

Synthesis of Compound 20

Compound 19 (1g, 5 mmol) was stirred in DCM/TFA (v/v=5:1) for one hour, white solid was obtained after the solvent was removed under reduced pressure. Yield: 99%. $^1$H NMR (CDCl$_3$, 300 MHz): 8.30 (bs, 2H), 3.57 (s, 2H), 3.18 (s, 2H), 2.09 (s, 2H). $^{13}$C NMR (CDCl$_3$, 300 MHz): 48.51, 37.81, 26.80. TOF-HRMS (m/z) found (calcd.) for C$_3$H$_8$N$_4$ (M): [M+H]$^+$, 101.0814 (101.0827).

Figure 18A:
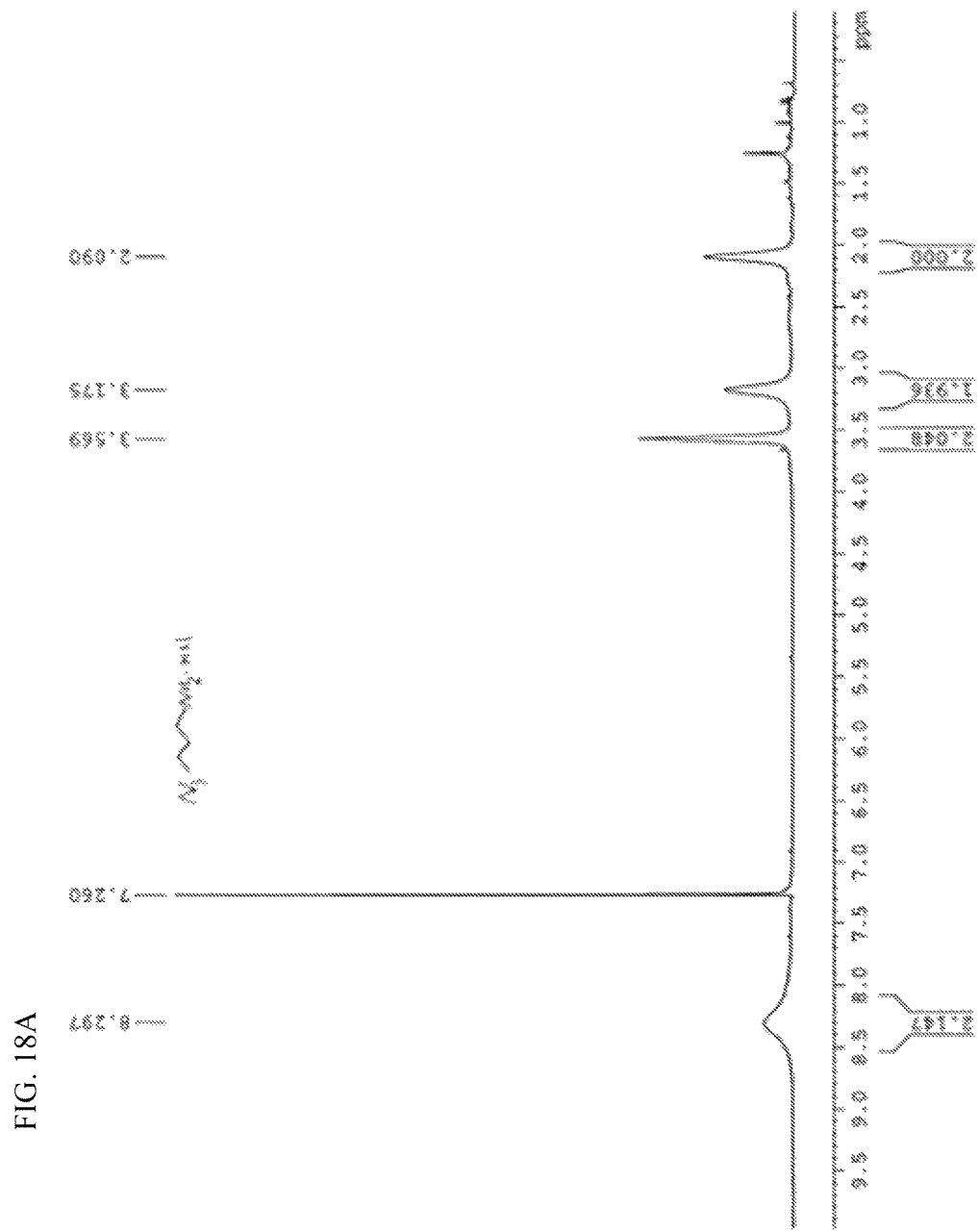
FIG. 18. (A) $^1$H NMR of compound 20; (B) $^{13}$C NMR of compound 20; (C) HRMS of compound 20.
Figure 18B:
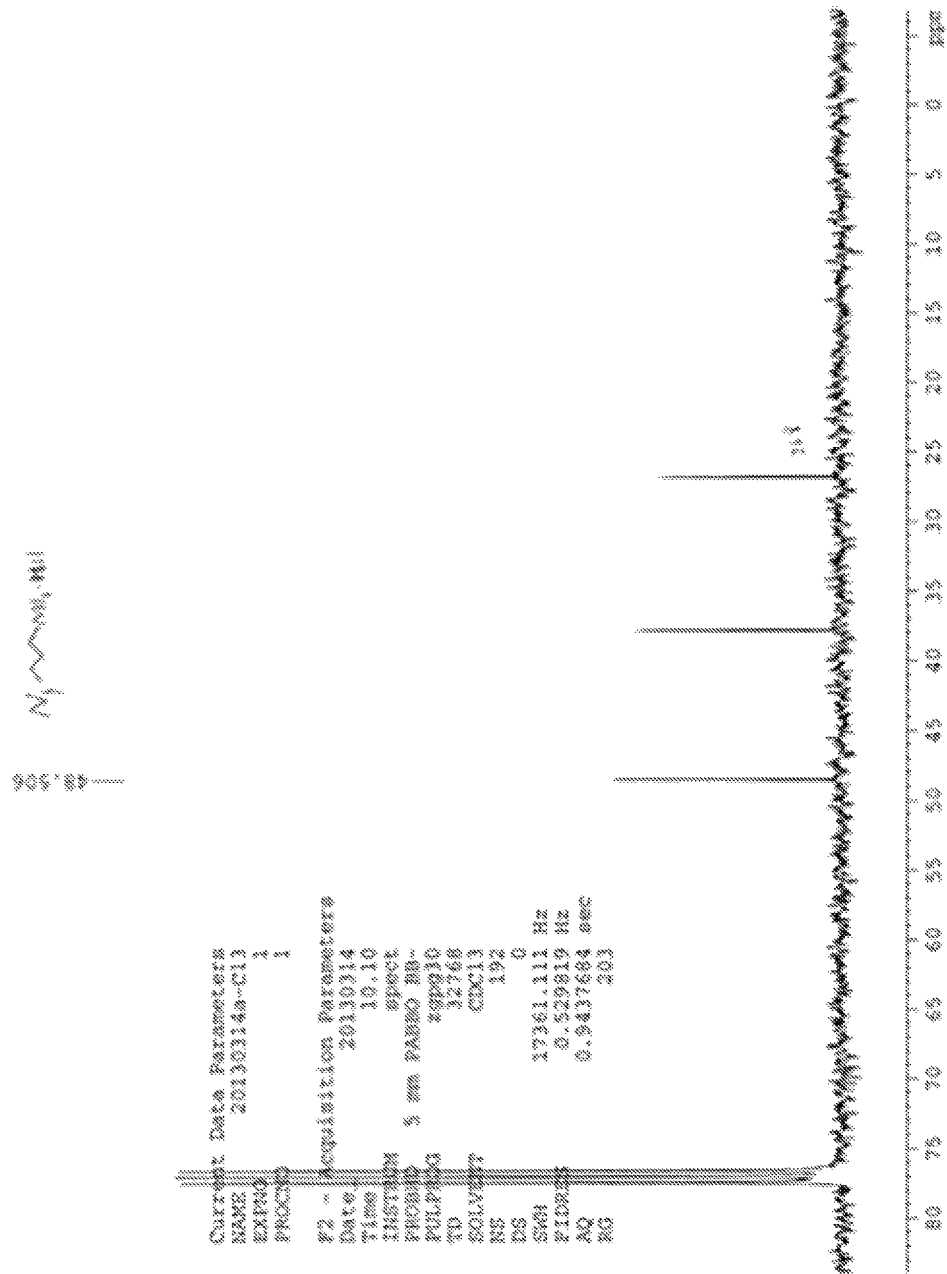
Figure 18C:
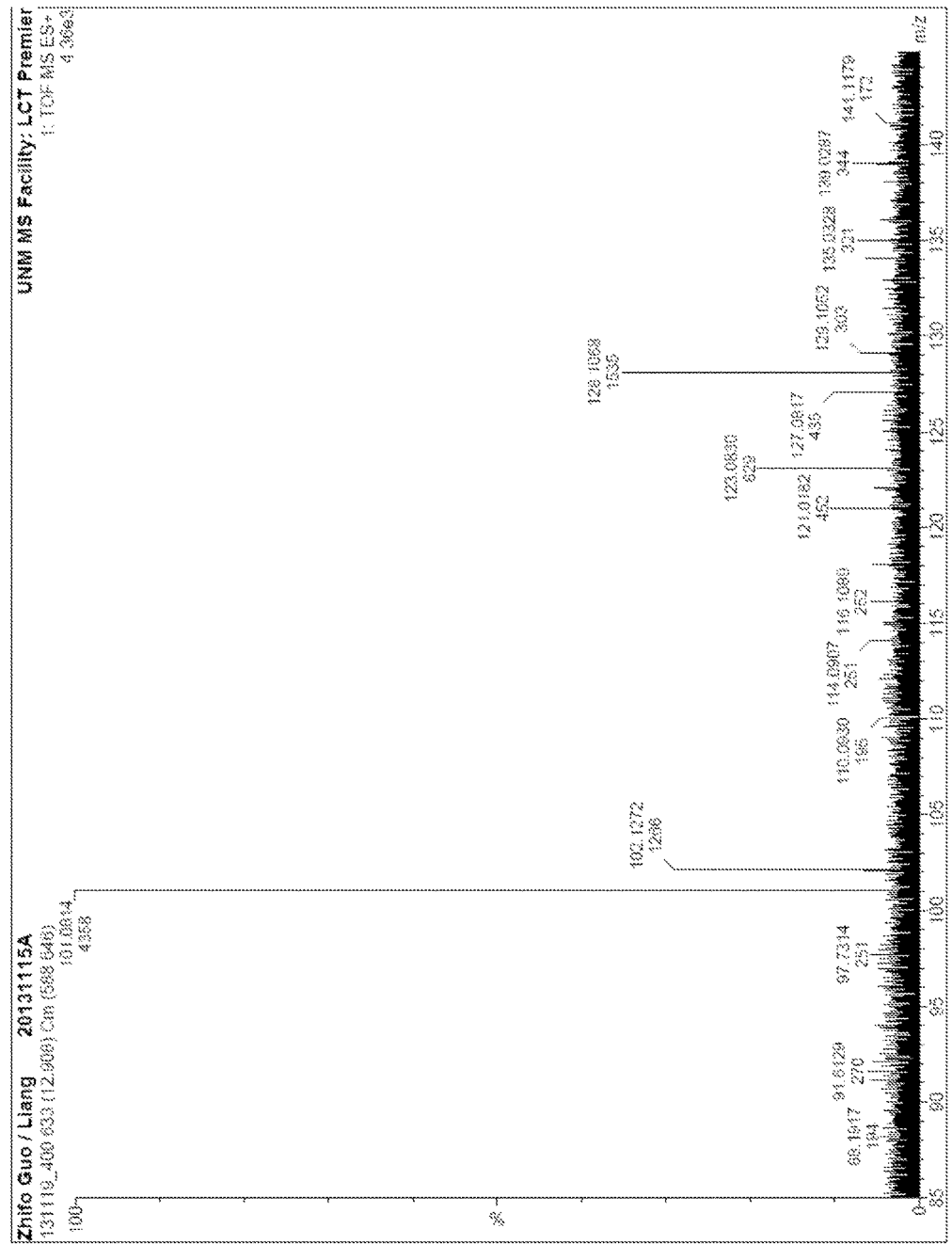

$^1$H NMR, $^{13}$C NMR, and HRMS are shown in FIG. 18.

Synthesis of Compound 21

3-(tritylthio)propanoic acid (697 mg, 2.0 mmol), HATU (836 mg, 2.2 mmol), DIPEA (516 mg, 4.0 mmol), and Compound 20 (220 mg, 2.2 mmol) were stirred at room temperature overnight in DCM. White solid was obtained after purification by silica gel column chromatography using hexane/ethyl acetate (v/v=1:1) as an eluting solvent (R$_f$=0.65). Yield: 96%. $^1$H NMR (Acetone-d$_6$, 300 MHz): 7.41-7.39 (m, 6H), 7.34-7.28 (m, 6H), 7.26-7.20 (m, 3H), 7.14 (bs, 1H), 3.39-3.35 (t, J=13.5 Hz, 2H), 3.27-3.20 (q, J=19.2 Hz, 2H), 2.44-2.39 (t, J=14.7 Hz, 2H), 2.22-2.17 (t, J=14.7 Hz, 2H), 1.77-1.68 (m, 2H). $^{13}$C NMR (Acetone-d$_6$, 300 MHz): 171.11, 145.83, 130.34, 128.70, 127.47, 67.17, 49.66, 37.10, 35.40, 28.53. TOF-HRMS (m/z) found (calcd.) for C$_{25}$H$_{26}$N$_4$OS (M): [M+Na]$^+$, 453.1717 (453.1725), [2M+Na]$^+$, 883.3400 (883.3552).

Figure 19A:
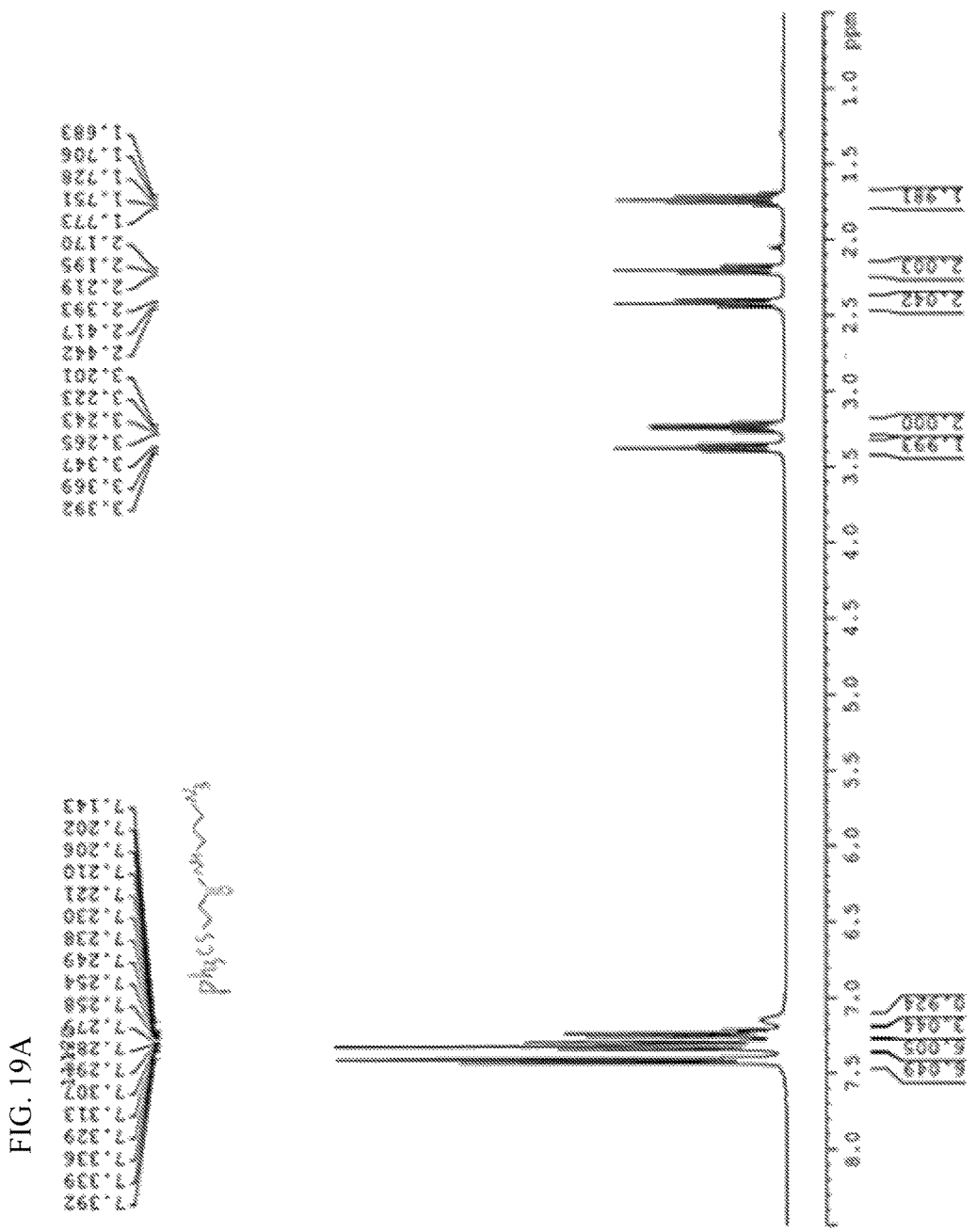
FIG. 19. (A) $^1$H NMR of compound 21; (B) $^{13}$C NMR of compound 21; (C) HRMS of compound 21.
Figure 19B:
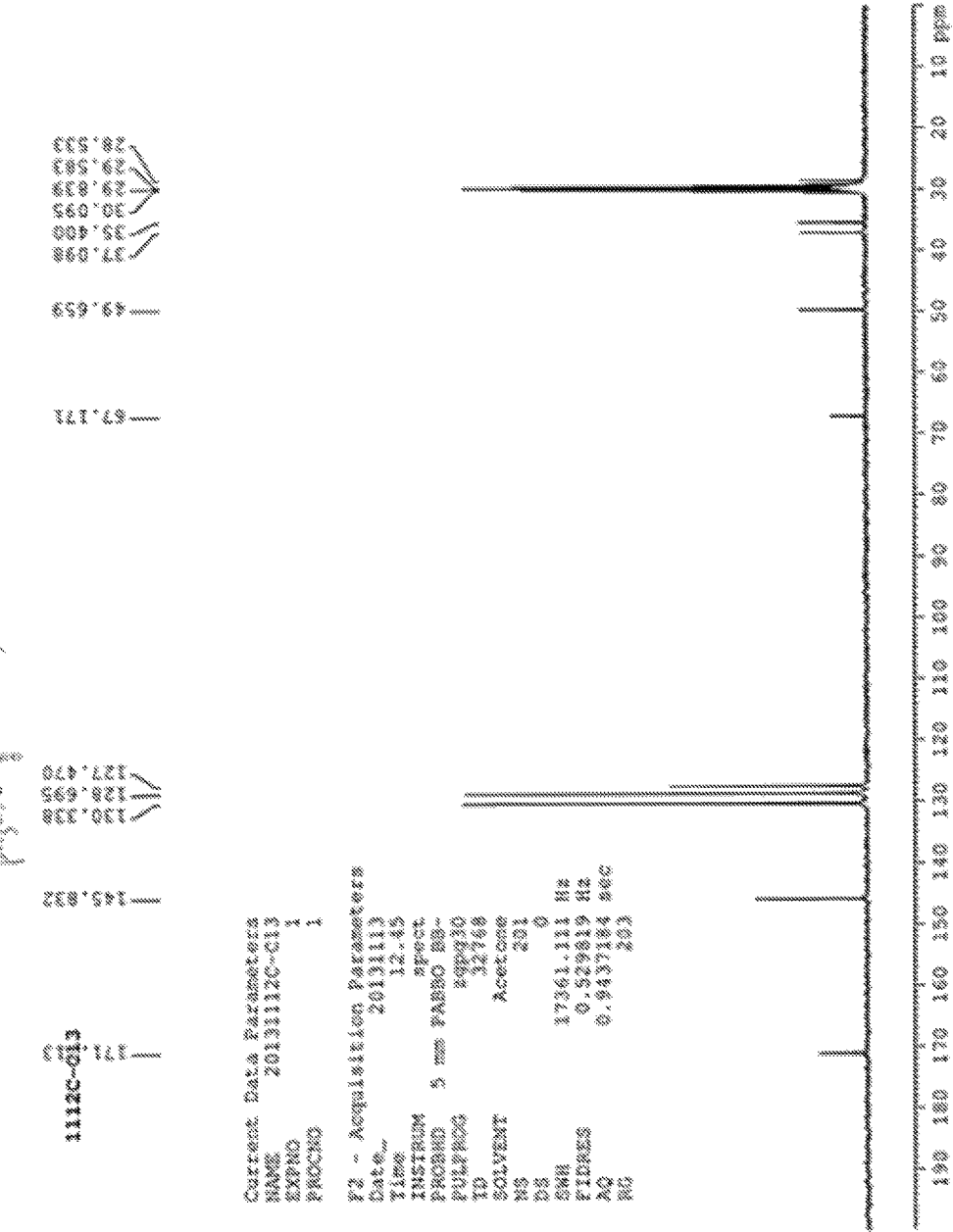
Figure 19C:
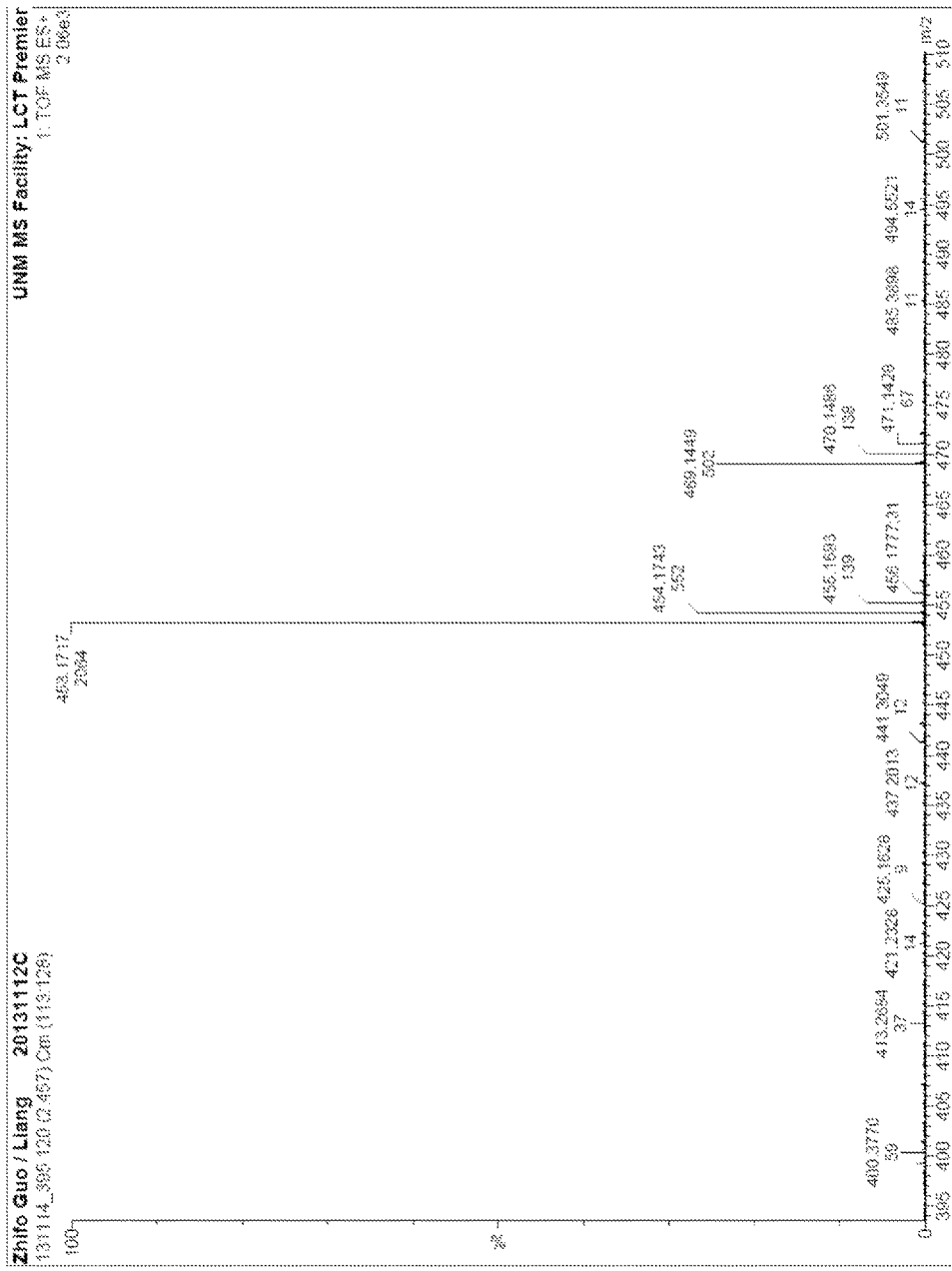

$^1$H NMR, $^{13}$C NMR, and HRMS are shown in FIG. 19.

Synthesis of Compound 9 (FIG. 11)

To a solution of Compound 21 (215 mg, 0.5 mmol) in trifluoroacetic acid (TFA, 1 mL) and CH$_2$Cl$_2$ (2 mL) was added triethylsilane (174 mg, 1.5 mmol). The resulting mixture was stirred for a half hour at room temperature. After evaporating the reaction solvent, CH$_2$Cl$_2$ (20 mL) was added to the resulting residues. The organic layer was extracted with H$_2$O (10 mL). The aqueous layer was then evaporated to give the transparent oil product. Yield: 94%. $^1$H NMR (CDCl$_3$, 300 MHz): 5.93 (s, 1H), 3.41-3.36 (m, 4H), 2.84-2.80 (q, J=12.9 Hz, 2H), 2.52-2.49 (t, J=7.8 Hz, 2H), 1.84-1.79 (m, 2H), 1.62-1.59 (t, J=9.9 Hz, 1H). $^{13}$C NMR (CDCl$_3$, 300 MHz): 171.58, 49.45, 40.46, 37.48, 28.79, 20.54. TOF-HRMS (m/z) found (calcd.) for C$_6$H$_{12}$N$_4$OS (M): [M+Na]$^+$, 211.0628 (211.0630), [2M+Na–2H]$^+$, 397.1207 (397.1207).

Figure 20A:
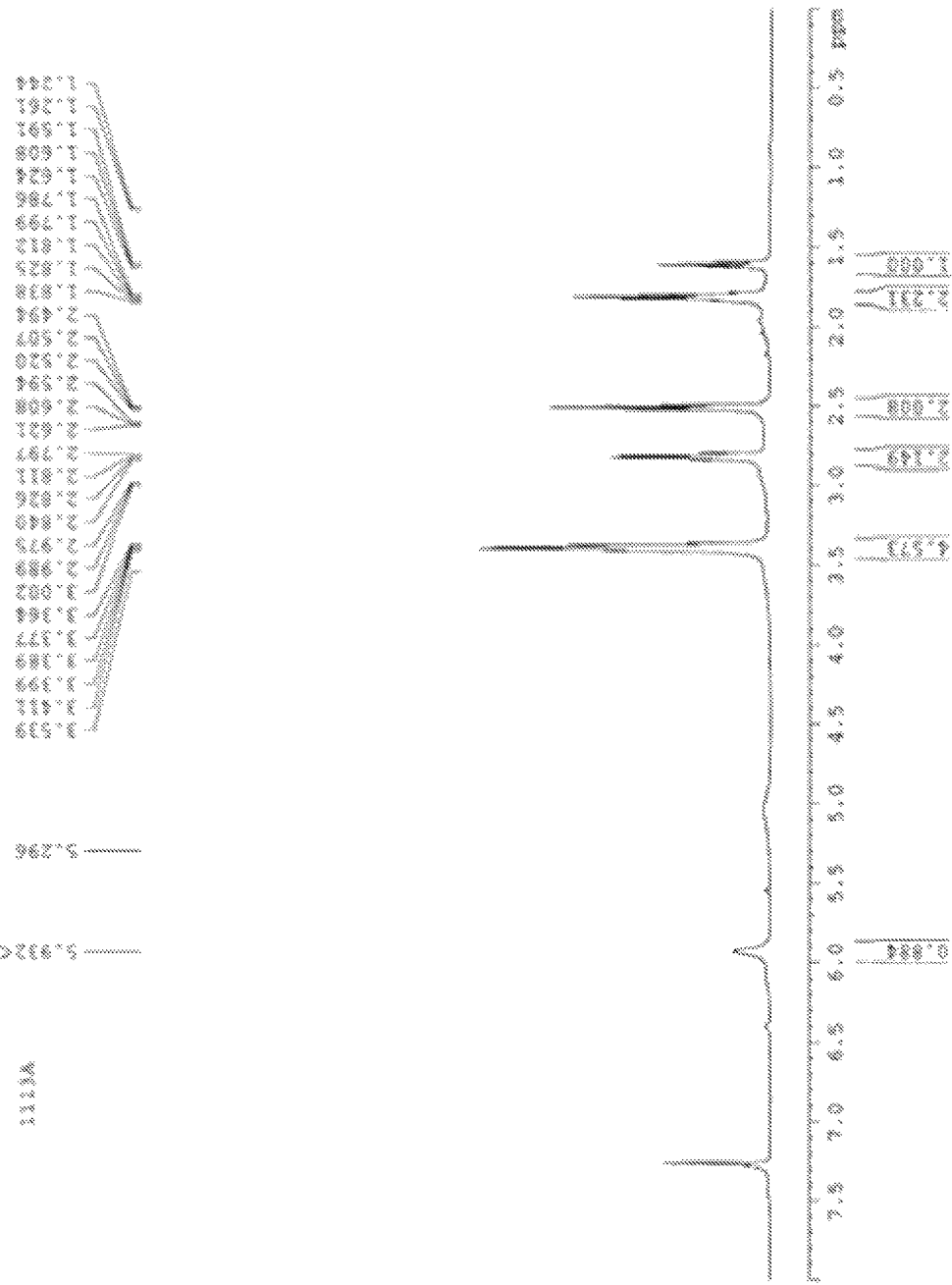
FIG. 20. (A) $^1$H NMR of compound 9; (B) $^{13}$C NMR of compound 9; (C) HRMS of compound 9.
Figure 20B:
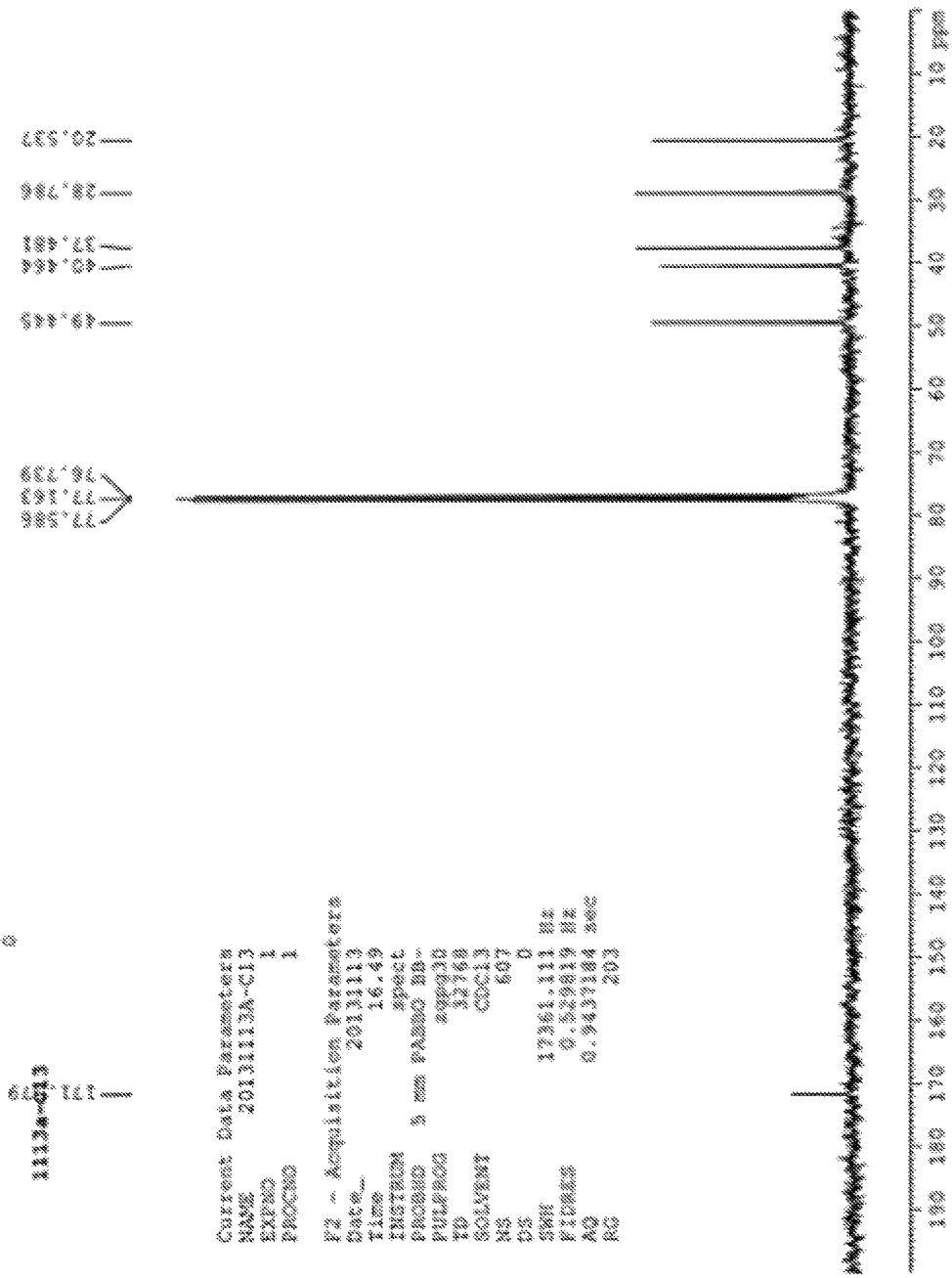
Figure 20C:
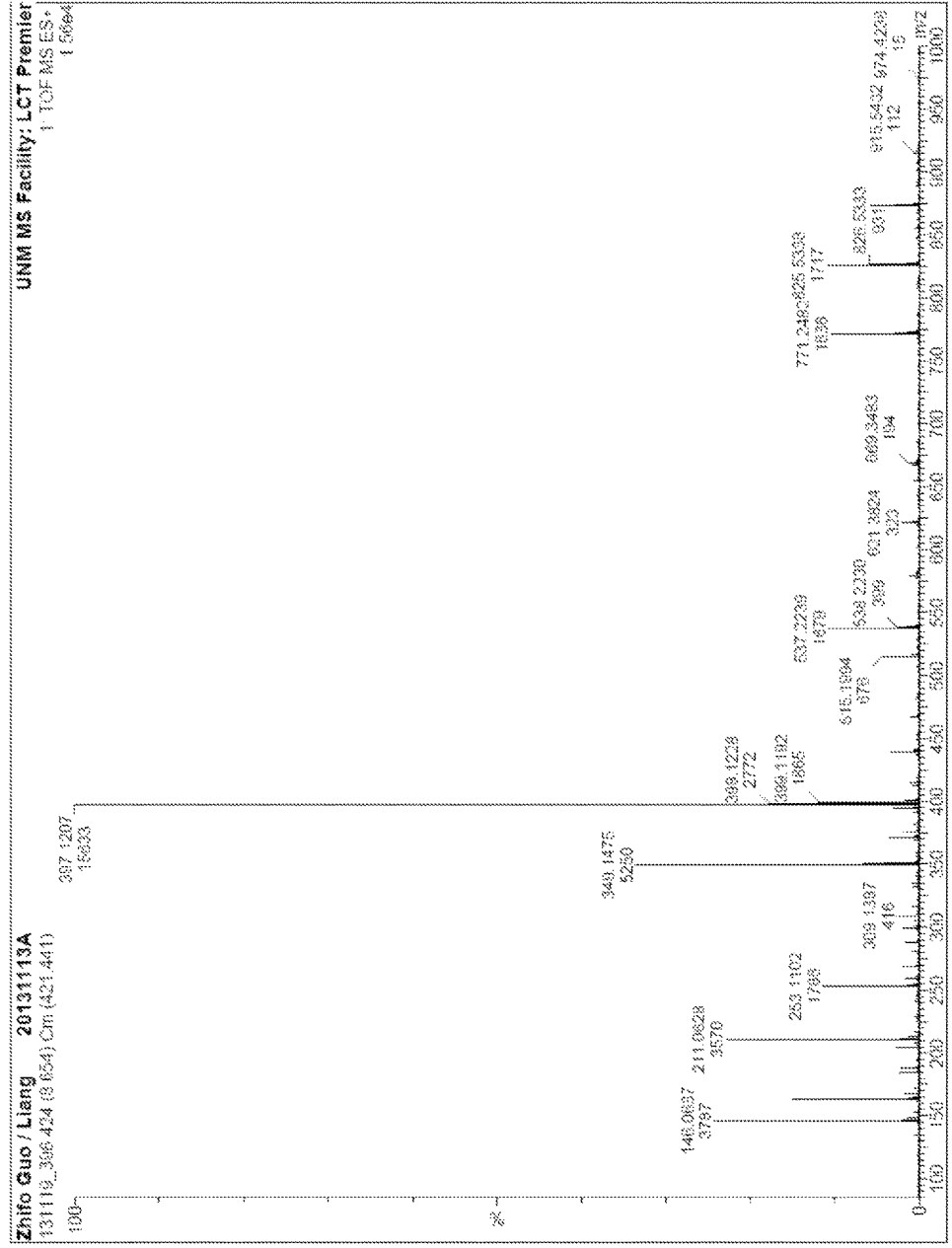

$^1$H NMR, $^{13}$C NMR, and HRMS are shown in FIG. 20.

Synthesis of Compound 3 (FIG. 11)

Tacrolimus (201.0 mg, 0.25 mmol), Boc-cysteamine (46.0 mg, 0.26 mmol), DPAP (3.2 mg, 12.5 nmol) and 0.4 mL dichloromethane were put in a vials, and stirred 15 minutes under UV light. White solid (246 mg, 98% yield) was obtained after purification by silica gel column chromatography using ethyl acetate as an eluting solvent (R$_f$=0.5). $^1$H NMR (300 MHz, CDCl$_3$): 5.33-5.21(d, J=36.8 Hz, 1H), 5.12-5.08 (m, 2H), 4.88-4.40 (m, 1H), 3.94-3.57 (m, 3H), 3.41-3.29 (m, 9H), 3.05-2.95 (m, 2H), 2.78-2.50 (m, 6H), 2.38-1.26 (m, 45H), 1.07-0.82(m, 13H). TOF-HRMS (m/z) found (calcd.) for C$_{51}$H$_{84}$N$_2$O$_{14}$S (M): [M+Na]$^+$, 1003.5583 (1003.5541).

Figure 21A:
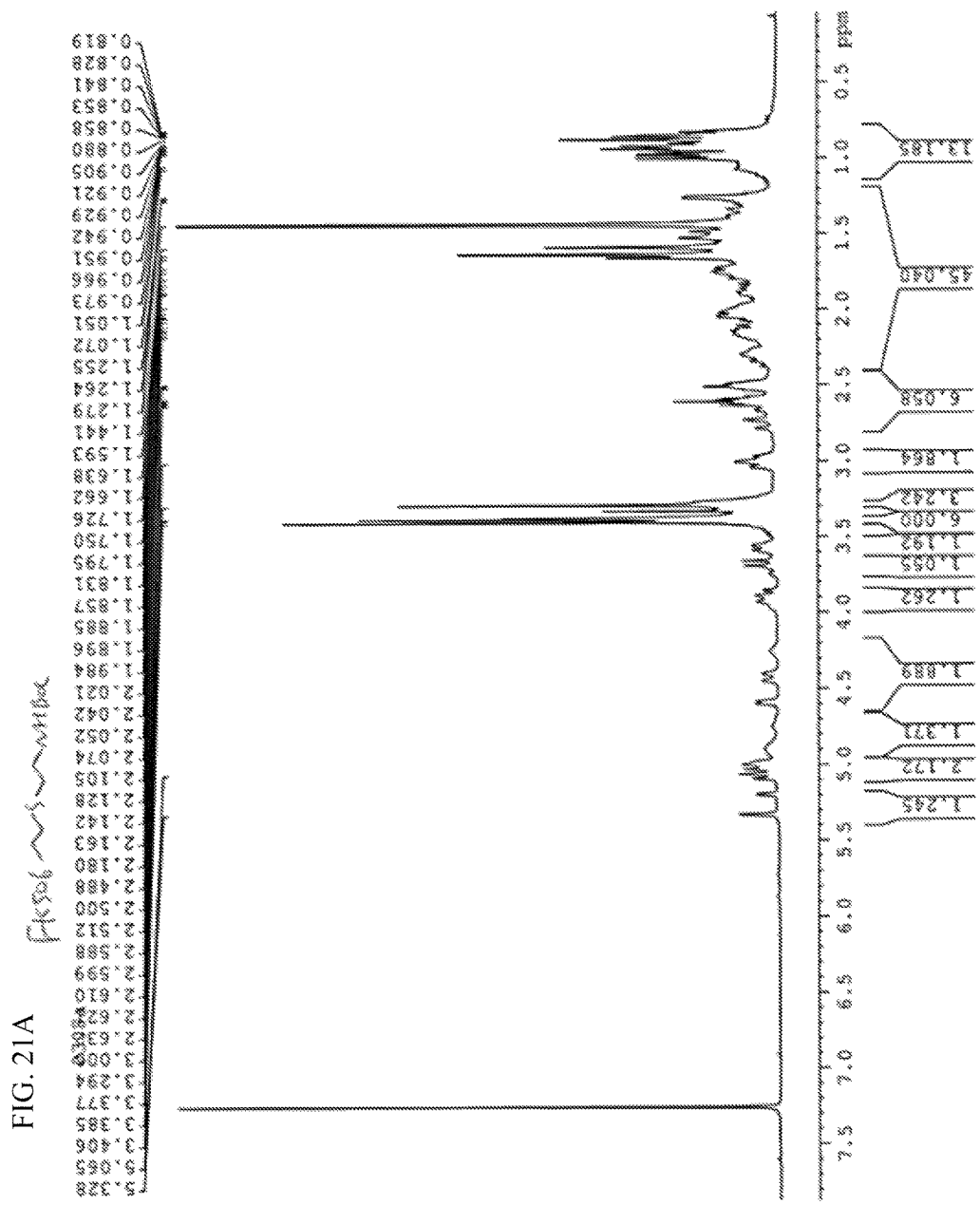
FIG. 21. (A) $^1$H NMR of compound 3; (B) HRMS of compound 3.
Figure 21B:
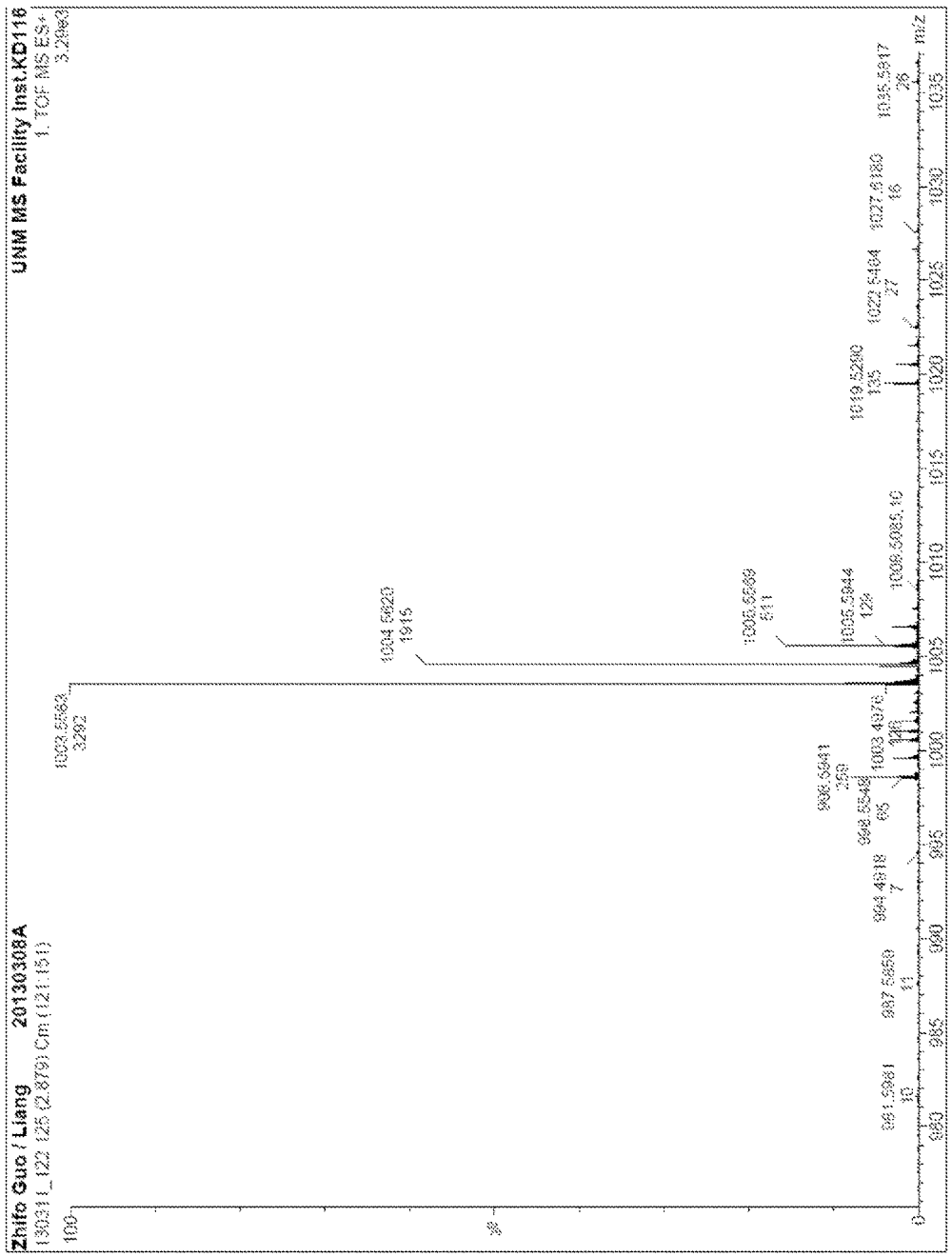

$^1$H NMR and HRMS are shown in FIG. 21.

Synthesis of Compound 4 (FIG. 11)

Method A: Compound 3 (FIG. 11) was dissolved in DCM/TFA and stirred for one hour at room temprature. Method B: Tacrolimus (201.0 mg, 0.25 mmol), cysteamine (19.3 mg, 0.26 mmol), DPAP (3.2 mg, 12.5 nmol) and 0.4 mL methanol were put in a vials, and stirred 15 minutes under UV light. White solid (211 mg, 96% yield) was obtained after purification by silica gel column chromatography using ethyl DCM/methanol (v/v=5:1) as an eluting solvent (R$_f$=0.56). $^1$H NMR (300 MHz, Acetone-d$_6$): 6.93-6.80 (m, 1H), 6.45-6.29 (m, 1H), 5.30-4.98 (m, 3H), 4.66-4.34 (m, 1 H), 4.13-4.02 (m, 2H), 3.80-3.32 (m, 11H), 3.02-3.00 (m, 2H), 2.68-2.50 (m, 4H), 2.49-1.58 (m, 36H), 1.21-0.88 (m, 13H). TOF-HRMS (m/z) found (calcd.) for C$_{46}$H$_{76}$N$_2$O$_{12}$S (M): [M+H]$^+$, 881.5215 (881.5197).

Figure 22A:
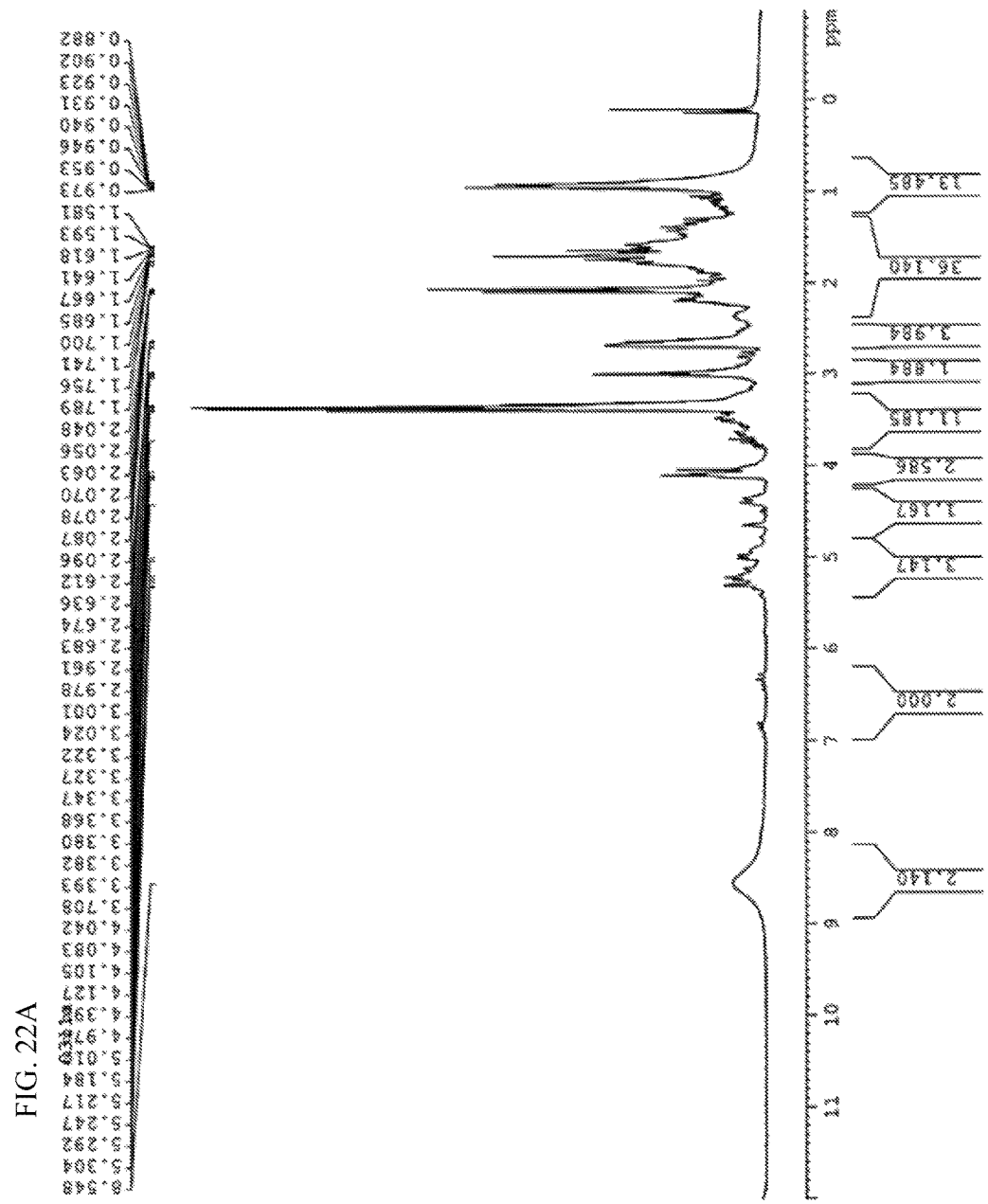
FIG. 22. (A) $^1$H NMR of compound 4; (B) HRMS of compound 4.
Figure 22B:
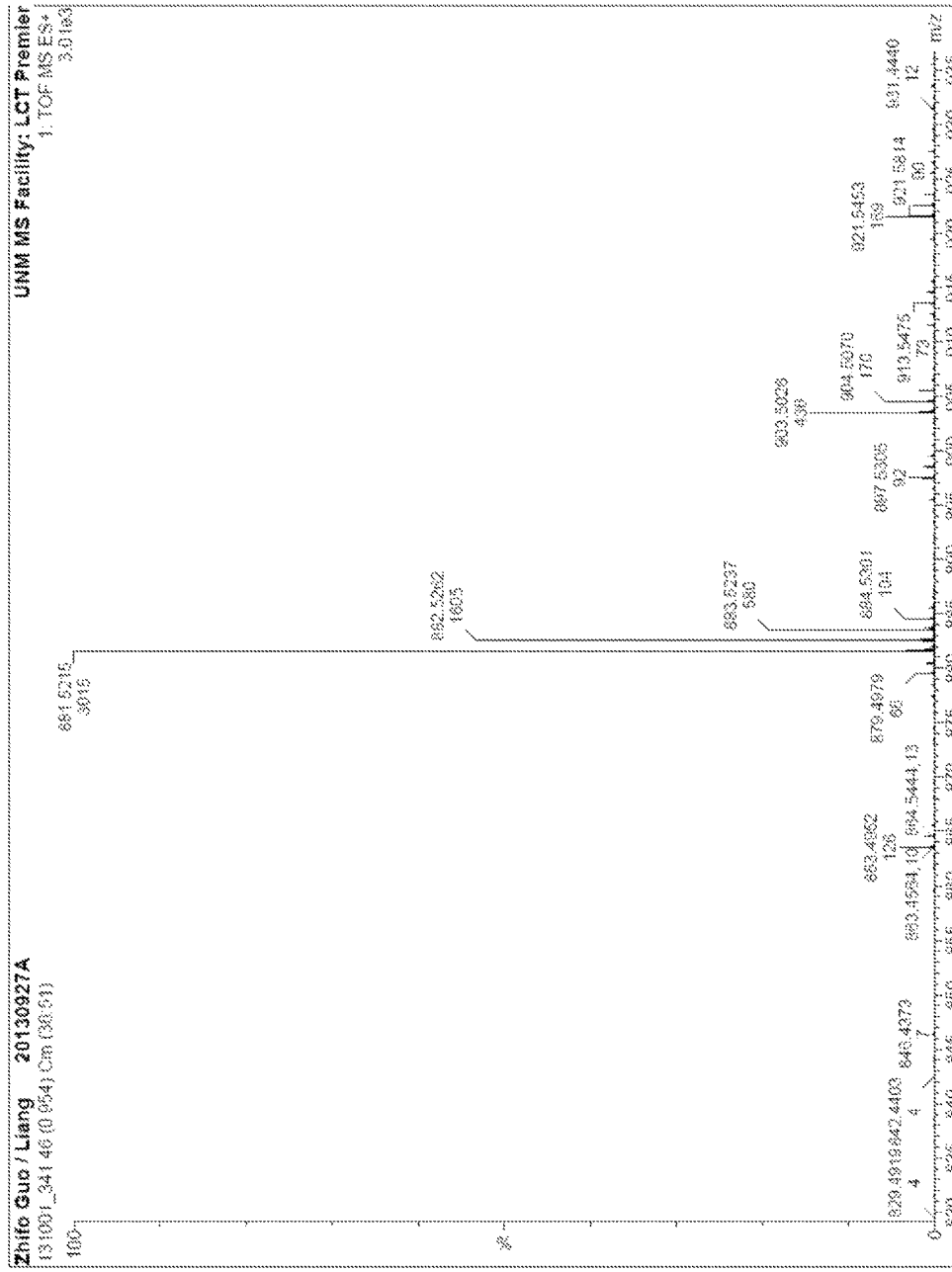

$^1$H NMR and HRMS are shown in FIG. 22.

Synthesis of Compound 6 (FIG. 11)

5-hexynoic acid (28.0 mg, 0.25 mmol), EDCI (52.7 mg, 0.275 mmol), HOBt (37.1 mg, 0.275 mmol), and Et$_3$N (50.5 mg, 0.5 mmol) were stirred for about one hour in DCM, then Compound 4 (242 mg, 0.275 mmol) was added and stirred overnight. White solid (190 mg, 78% yield) was obtained after purification by silica gel column chromatography using ethyl acetate as an eluting solvent (R$_f$=0.42). $^1$H NMR (300 MHz, CDCl$_3$): 6.80-6.69 (m, 1H), 6.34-6.10 (m, 1H), 5.97 (s, 1H), 5.26-4.85 (m, 2H), 4.75-4.72 (m, 1H), 4.49-4.16 (m, 1H), 3.92-3.72 (m, 1H), 3.59-3.26 (m, 11H), 3.06-2.92 (m, 2H), 2.63-2.61 (m, 2H), 2.49-2.23 (m, 6H), 2.12-1.23 (m, 39H), 1.80-0.83 (m, 13H). TOF-HRMS (m/z) found (calcd.) for C$_{52}$H$_{82}$N$_2$O$_{13}$S (M): [M+H]$^+$, 979.5360 (976.2860).

Figure 23A:
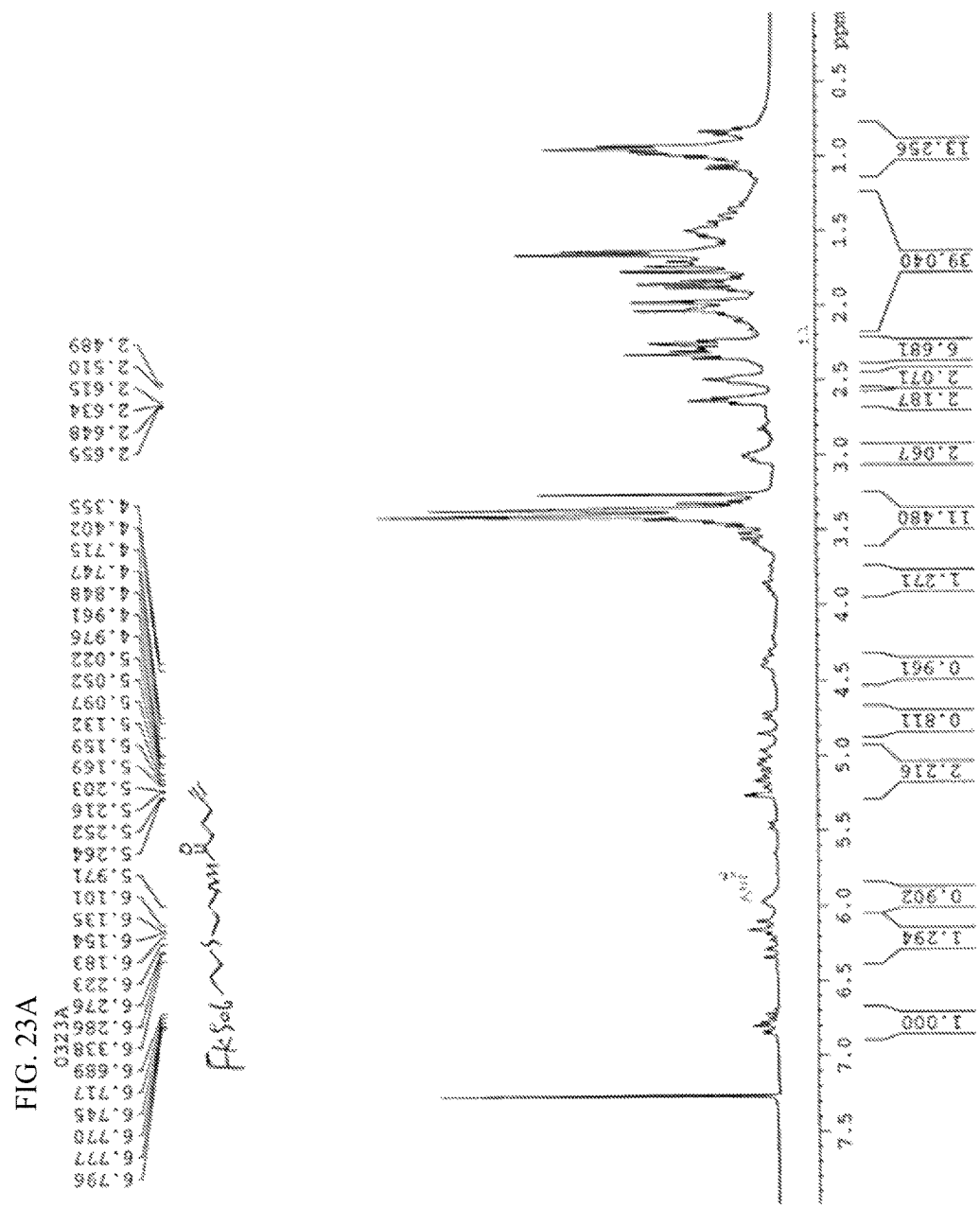
FIG. 23. (A) $^1$H NMR of compound 6; (B) HRMS of compound 6.
Figure 23B:
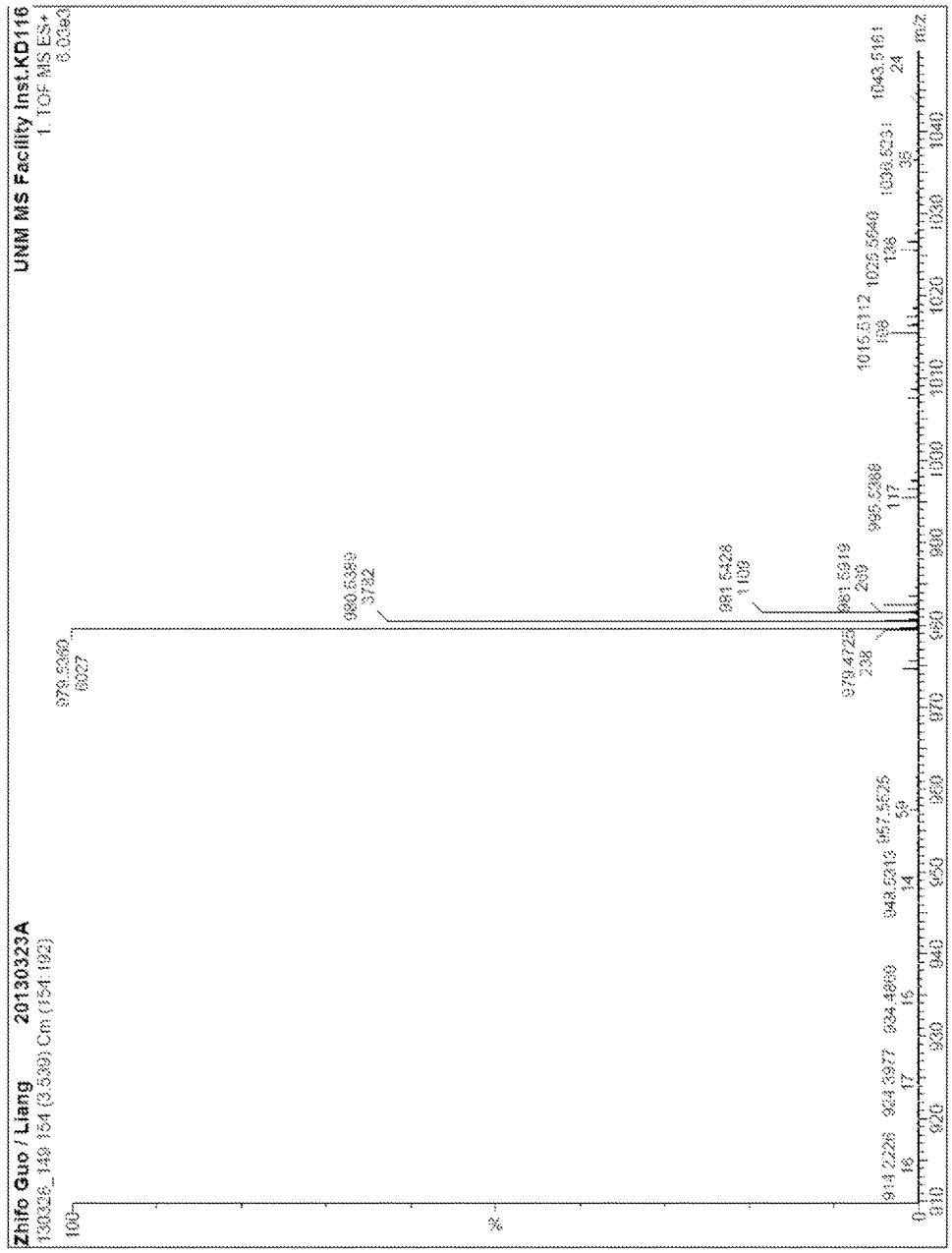

$^1$H NMR and HRMS are shown in FIG. 23.

Synthesis of Compound 11 (FIG. 11)

Tacrolimus (201.0 mg, 0.25 mmol), 3-thiopropanoic acid (28.0 mg, 0.26 mmol), DPAP (3.2 mg, 12.5 nmol), and 0.4 mL dichloromethane were put in a vial and stirred 15 minutes under UV light. White solid (222 mg, 98% yield) was obtained after purification by silica gel column chromatography using ethyl acetate/acetone (v/v=1:1) as an eluting solvent (R$_f$=0.51). $^1$H NMR (300 MHz, CDCl$_3$): 5.32-5.20(d, J=36.4 Hz, 1H), 5.10-5.00 (m, 2H), 4.75-4.30 (m, 1H), 3.94-3.54 (m, 3H), 3.40-3.29 (m, 11H), 3.05-2.95 (m, 2H), 2.75-2.51 (m, 6H), 2.38-1.25 (m, 36H), 1.06-0.82(m, 13H). TOF-HRMS (m/z) found (calcd.) for C$_{47}$H$_{75}$NO$_{14}$S (M): [M–H]$^+$, 908.4821 (908.4830).

Figure 24A:
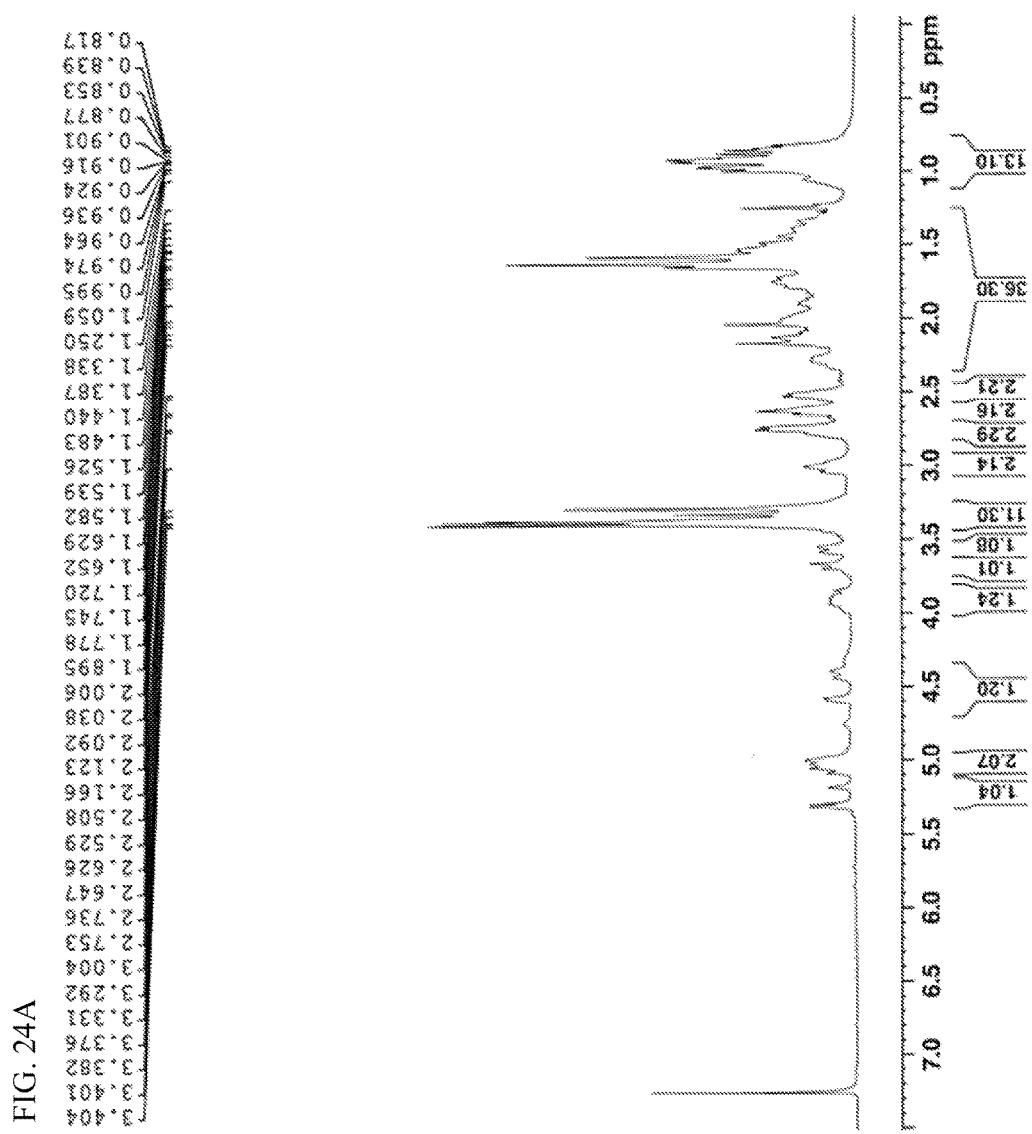
FIG. 24. (A) $^1$H NMR of compound 11; (B) HRMS of compound 11.
Figure 24B:
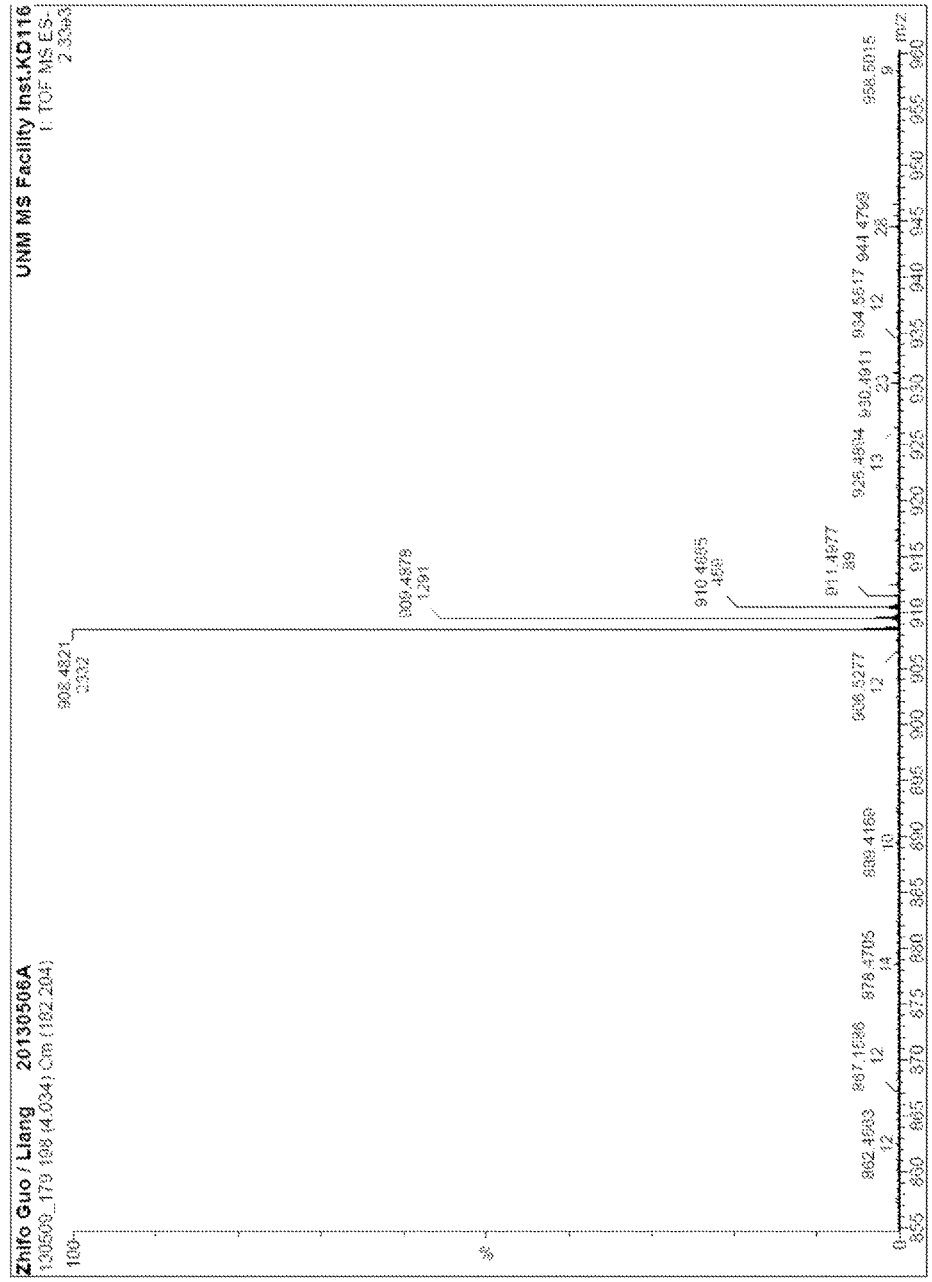

$^1$H NMR and HRMS are shown in FIG. 24.

Synthesis of Compound 12 (FIG. 11)

Tacrolimus (201.0 mg, 0.25 mmol), Compound 9 (48.9 mg, 0.26 mmol), DPAP (3.2 mg, 12.5 nmol), and 0.4 mL DCM were put in a vial and stirred 15 minutes under UV light. Pale yellow solid (235 mg, 95% yield) was obtained after purification by silica gel column chromatography using ethyl acetate/acetone (v/v=4:1) as an eluting solvent (R$_f$=0.56). $^1$H NMR (300 MHz, CDCl$_3$): 6.50 (s, 1H), 5.32-4.95 (m, 3H), 4.74-4.22 (m, 2H), 3.91-3.53 (m, 2H), 3.38-3.27 (m, 17H), 2.98-2.95 (m, 4H), 2.80-2.64 (m, 4H), 2.58-2.39 (m, 4H), 2.15-1.34 (m, 34H), 0.98-0.80 (m, 13H). TOF-HRMS (m/z) found (calcd.) for C$_{50}$H$_{81}$N$_5$O$_{13}$S (M): [M+Na]$^+$, 1014.5485 (1014.5449).

Figure 25A:
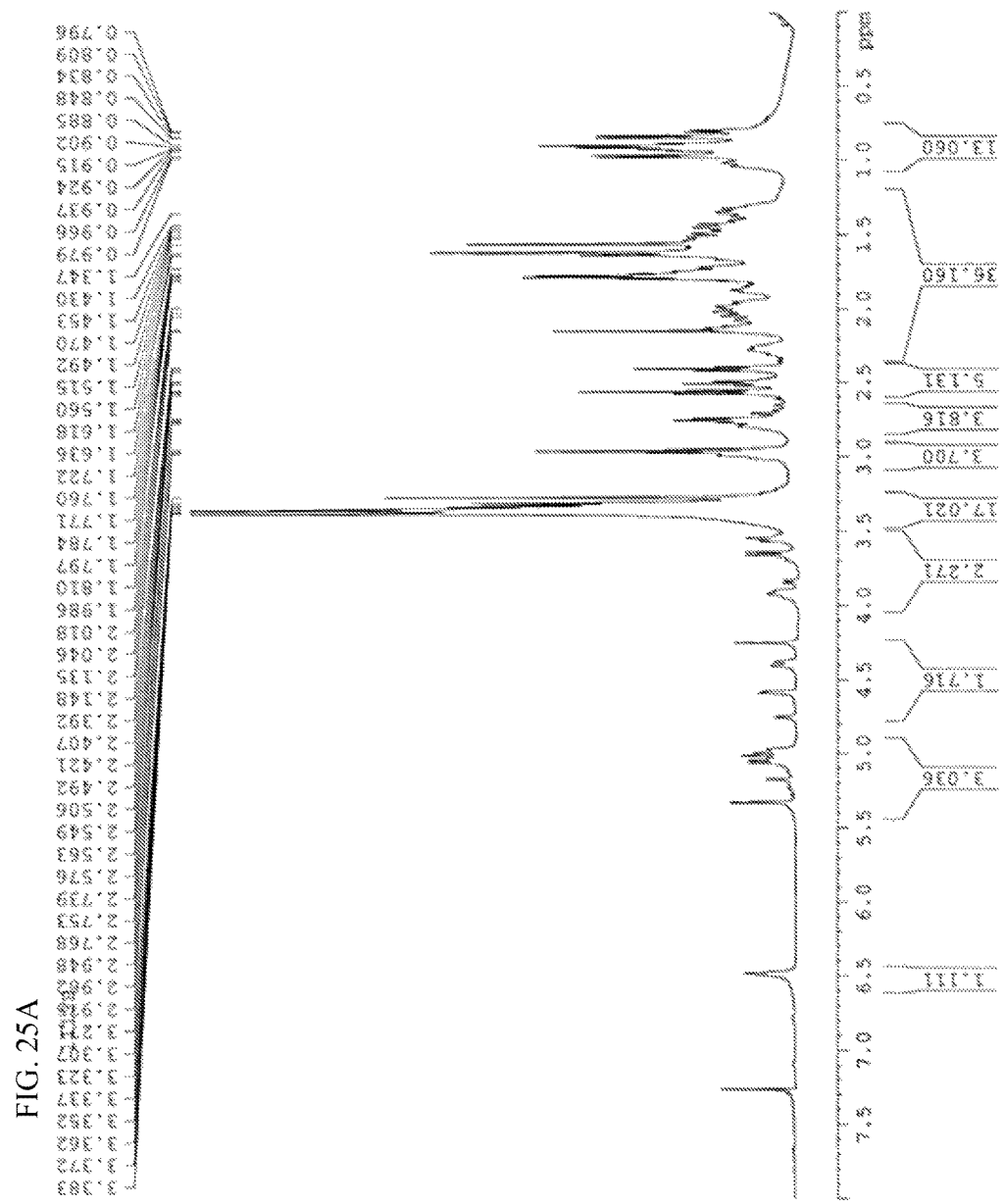
FIG. 25. (A) $^1$H NMR of compound 12; (B) HRMS of compound 12.
Figure 25B:
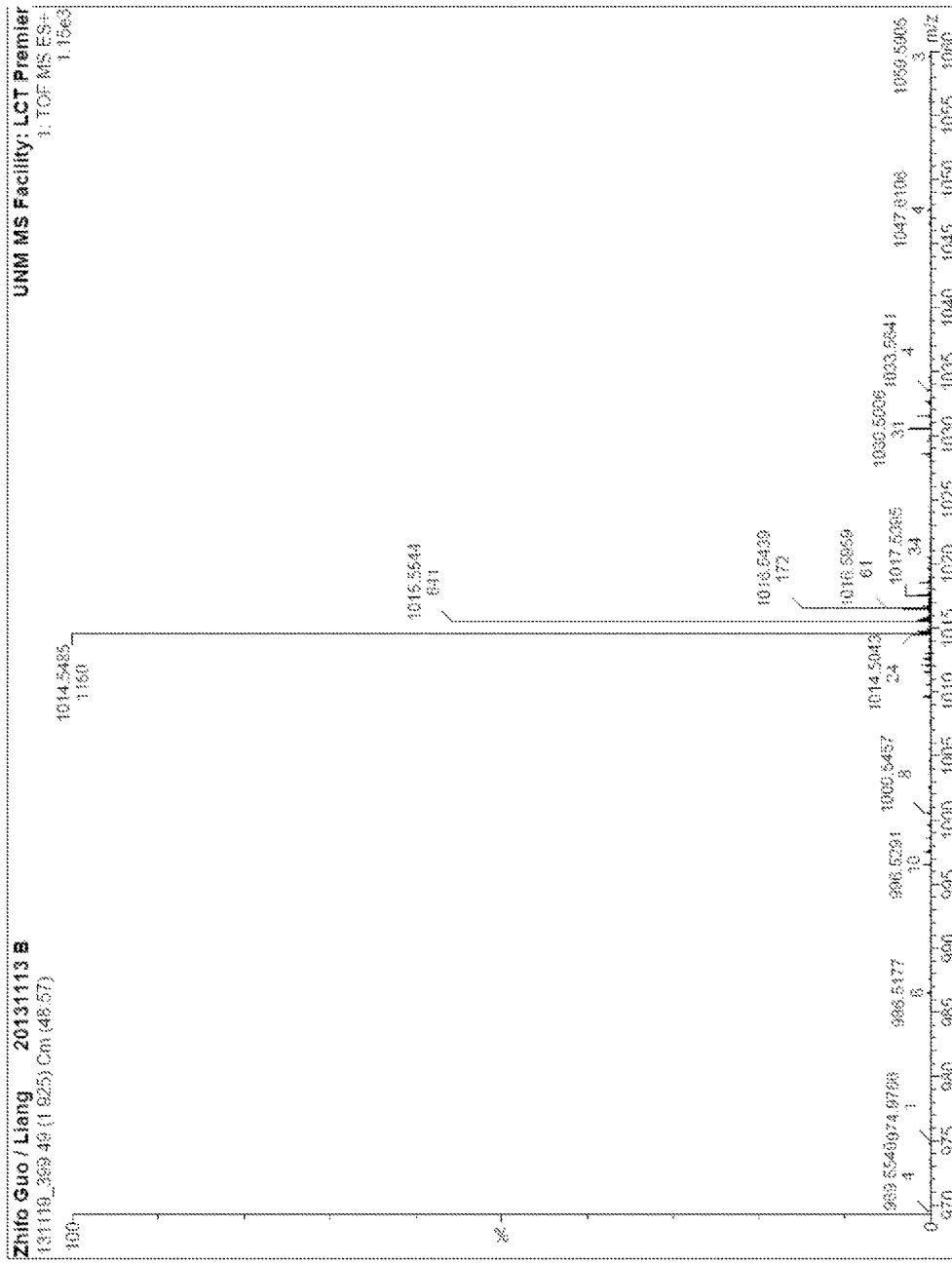

$^1$H NMR and HRMS are shown in FIG. 25.

Synthesis of Compound 13 (FIG. 11)

Tacrolimus (201.0 mg, 0.25 mmol), cysteine (31.5 mg, 0.26 mmol), DPAP (3.2 mg, 12.5 nmol), and 0.5 mL methanol/water (1:1) were put in a vial and stirred 15 minutes under UV light. White solid (220 mg, 95% yield) was obtained after purification by silica gel column chromatography using acetone/methanol (v/v=1:1) as an eluting solvent (R$_f$=0.46). $^1$H NMR (300 MHz, CDCl$_3$): 5.27-4.95

(m, 3H), 4.63-4.33 (m, 1H), 4.08-3.97 (m, 2H), 3.70-3.41 (m, 3H), 3.38-2.75 (m, 13H), 2.09-1.20 (m, 34H), 0.96-0.71 (m, 13H). TOF-HRMS (m/z) found (calcd.) for $C_{47}H_{76}N_2O_{14}S$ (M): [M+H]$^+$, 925.5076 (925.5096).

Figure 26A:
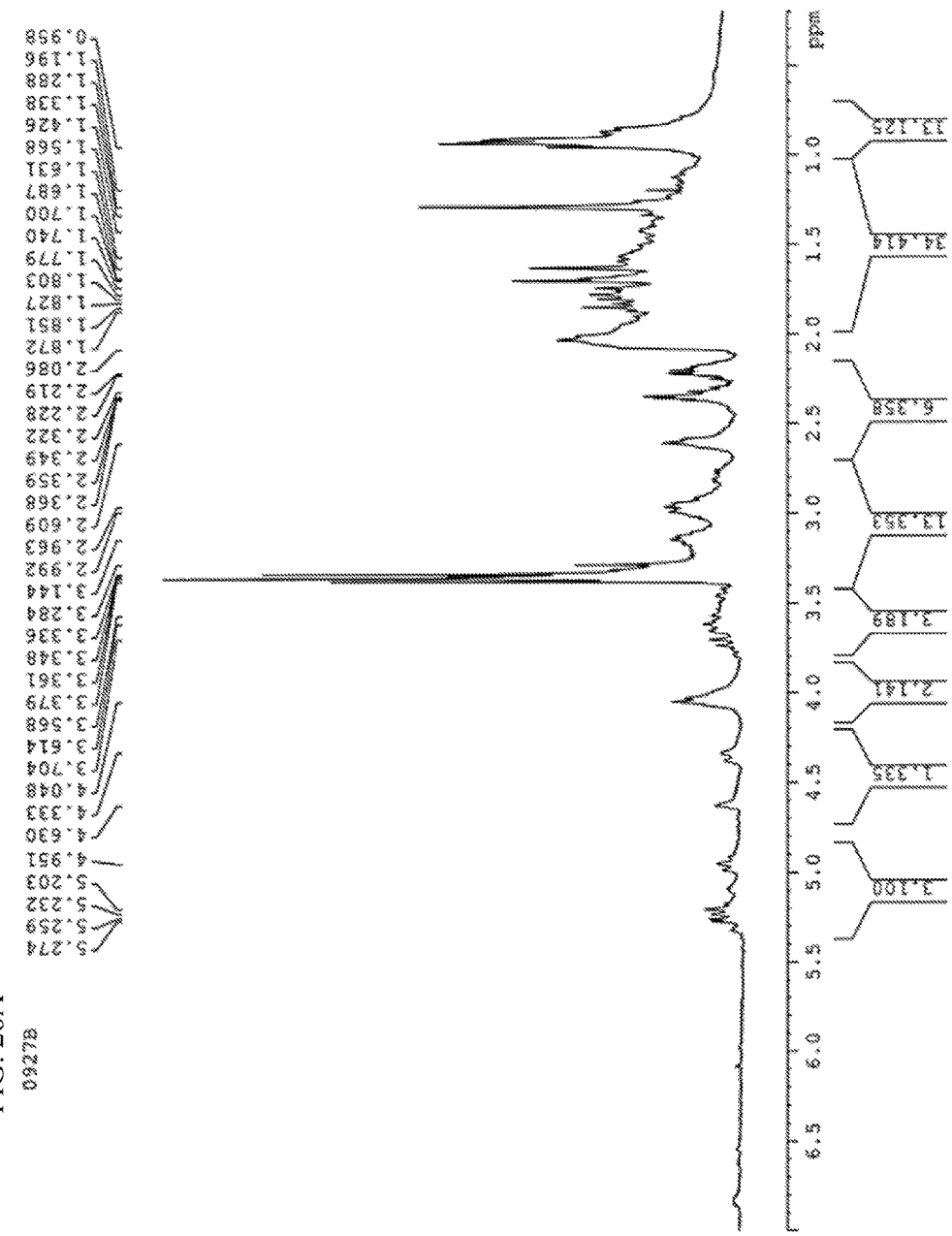
FIG. 26. (A) $^1$H NMR of compound 13; (B) HRMS of compound 13.
Figure 26B:
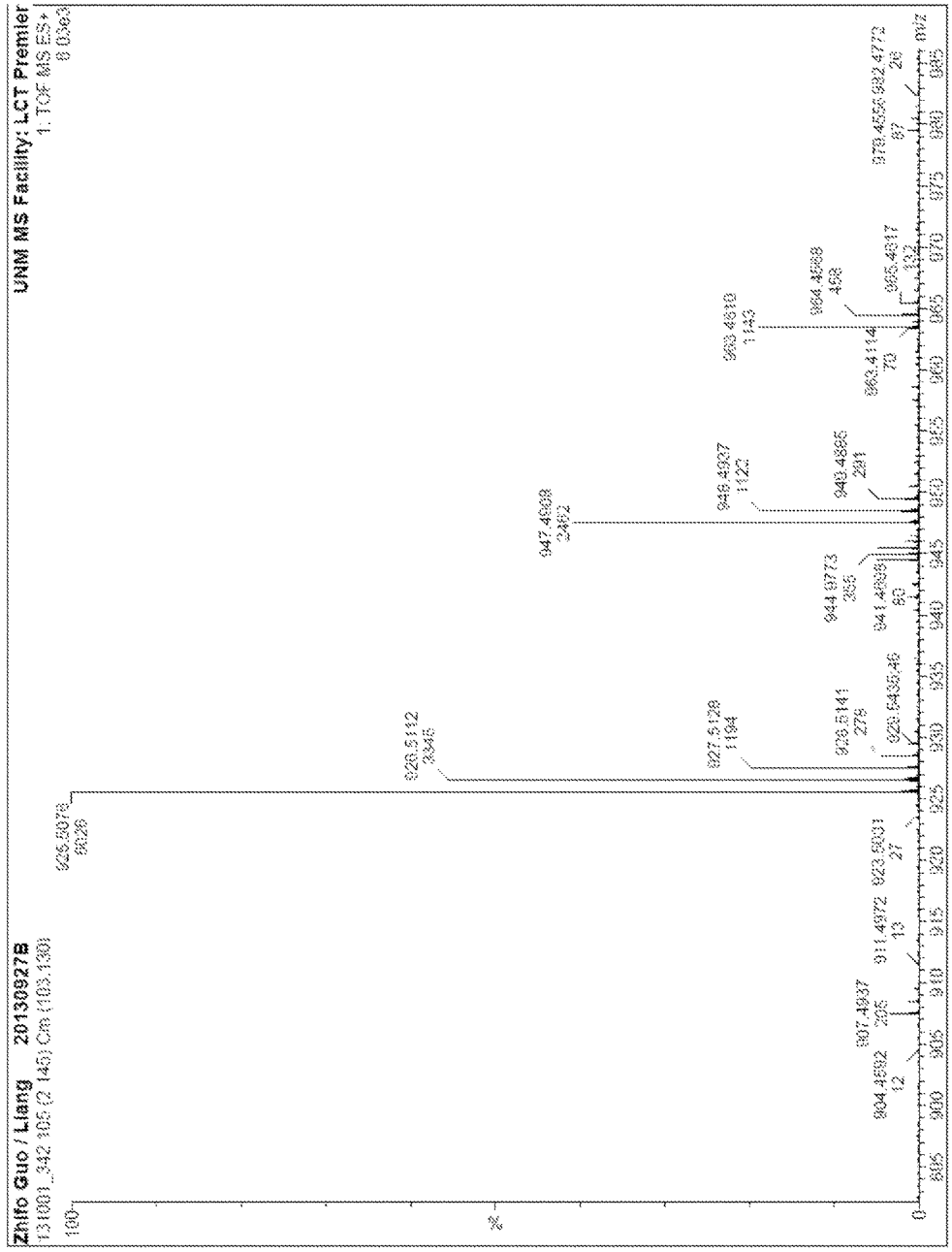

$^1$H NMR and HRMS are shown in FIG. 26.

Figure 12:
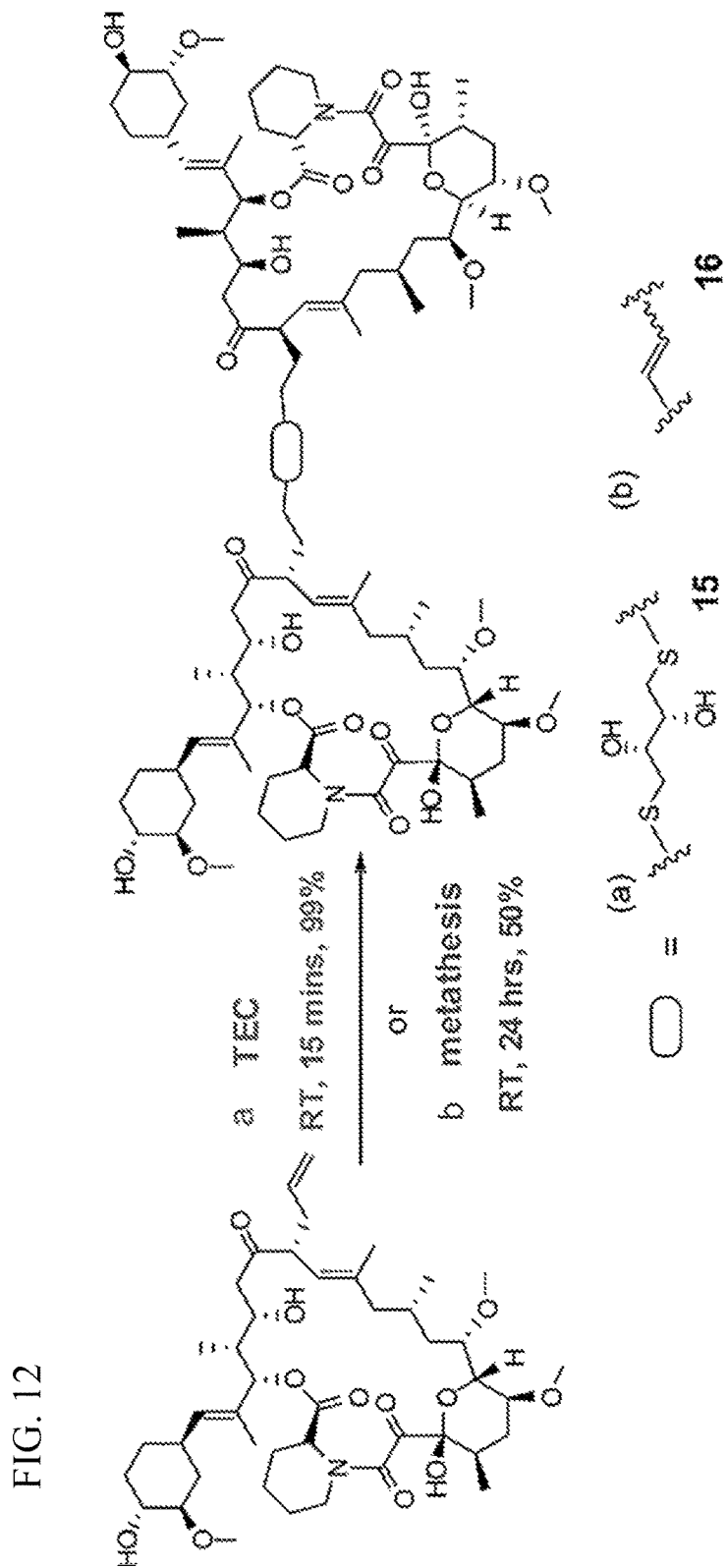
FIG. 12. Synthesis of FK1012s.
Figure 13A:
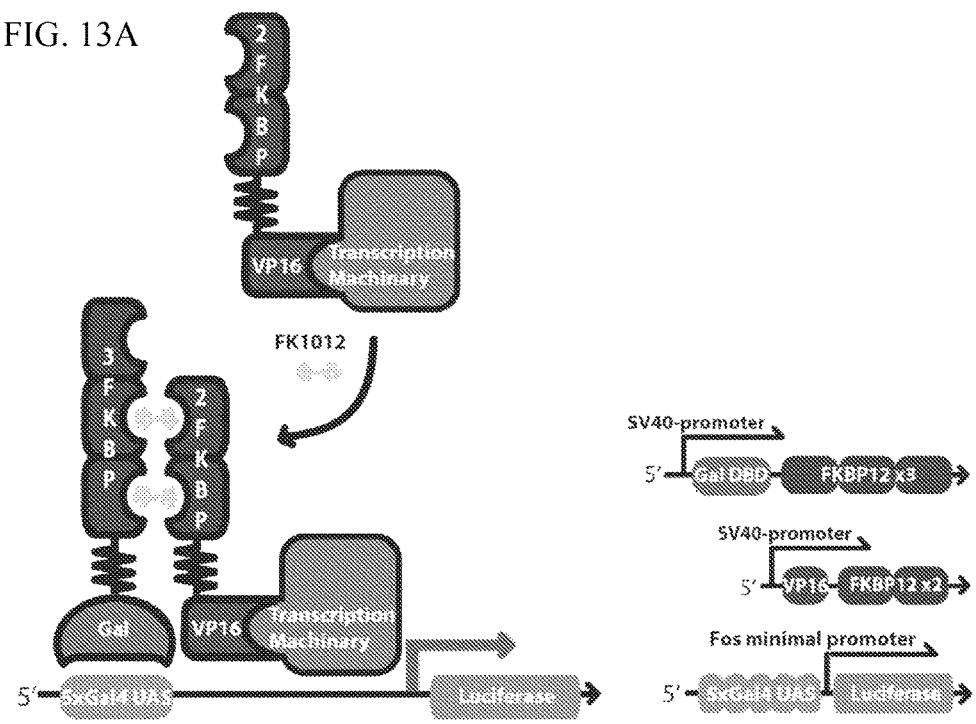
FIG. 13. (A) FK1012-induced luciferase expression and DNA constructs for the assays; (B) Induction fold change of luciferase. Results were generated from three experiments.
Figure 13B:
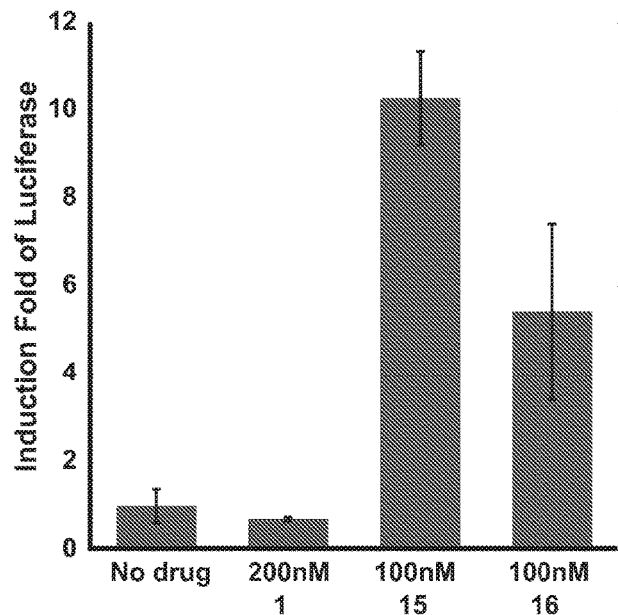

Synthesis of Compound 15 (FIG. 12)

Tacrolimus (201.0 mg, 0.25 mmol), dithiothreitol (20.2 mg, 0.13 mmol), DPAP (3.2 mg, 12.5 nmol), and 0.4 mL dichloromethane were put in a vial and stirred 15 minutes under UV light. White solid (220 mg, 99% yield) was obtained after purification by silica gel column chromatography using ethyl acetate/acetone (v/v=1:1) as an eluting solvent ($R_f$=0.56). $^1$H NMR (300 MHz, CDCl$_3$): 5.33-5.20 (d, J=36.5 Hz, 2H), 5.10-5.06 (m, 4H), 4.74-4.28 (m, 4H), 3.92-3.57 (m, 8H), 3.41-3.30 (m, 22H), 3.06-2.97 (m, 4H), 2.74-2.54 (m, 14H), 2.30-1.25 (m, 64H), 1.08-0.83 (m, 26H). TOF-HRMS (m/z) found (calcd.) for $C_{92}H_{148}N_2O_{26}S_2$ (M): [M+Na]$^+$, 1783.9602 (1783.9659).

Figure 27A:
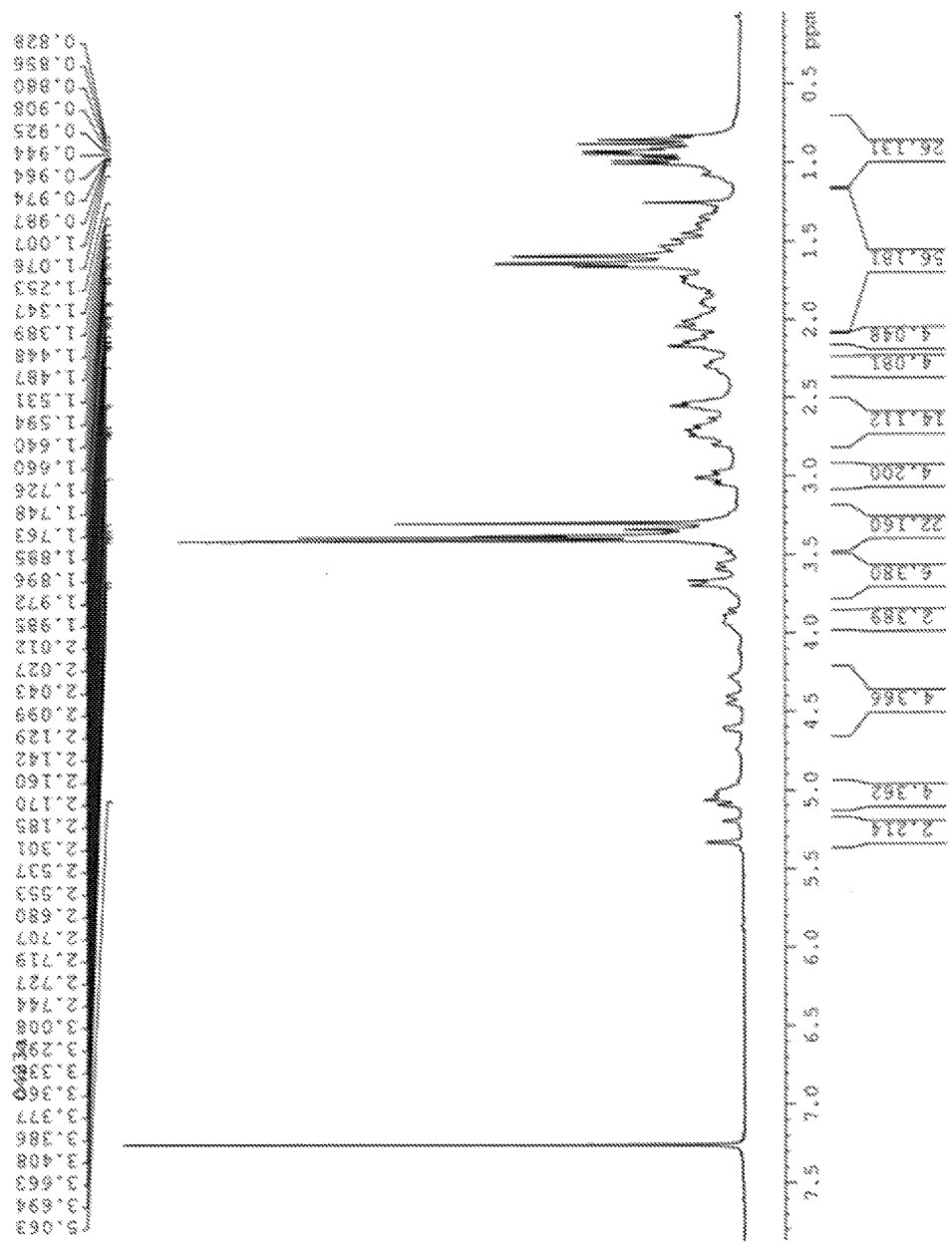
FIG. 27. (A) $^1$H NMR of compound 15; (B) HRMS of compound 15.
Figure 27B:
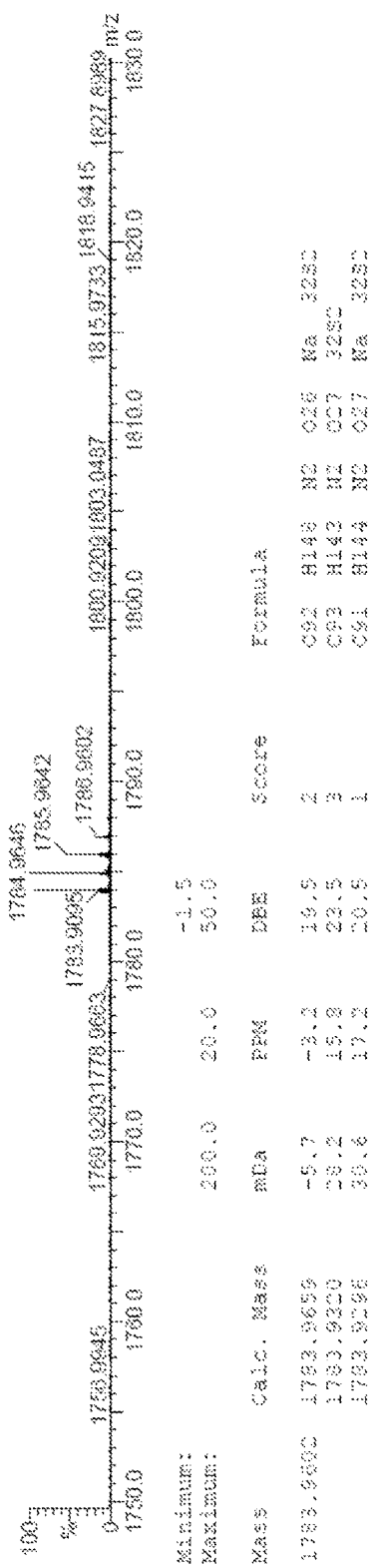

$^1$H NMR and HRMS are shown in FIG. 27.

Plasmid Construction

All DNA fragments were amplified by PCR performed with PHUSION DNA Polymerase (New England Biolabs Inc., Ipswich, Mass.), PFUULTRA II Fusion HotStart DNA Polymerase (Agilent Technologies, Inc., Santa Clara, Calif.) under S1000 thermal cycler with Dual 48/48 Fast Reaction Module (Bio-Rad Laboratories, Inc., Hercules, Calif.).

For SV-ires-GalDBD-3FKBP12, a DNA construct SV-VP16-Frb-ires-GalDBD-FKBP12x3 (Liang et al. 2011. Sci. Signal., 2011, 4, rs2) was firstly digested by EcoRI and BamHI. The sticky ends of the vector were blunted by DNA Polymerase I Lg (Klenow) Fragment (New England Biolabs Inc., Ipswich, Mass.) in the presence of dNTPs. Finally, the blunt ends were ligated by T4 DNA Ligase (New England Biolabs Inc., Ipswich, Mass.).

For SV-VP16-FKBP12x2, the DNA construct was first made as SV-VP16-FKBP12. SV-VP16-Frb-ires-GalDBD-FKBP12x3 was firstly digested by AscI and NotI. The PCR product of FKBP12 was inserted into the vector by recombination using the In-Fusion HD Enzyme Premix (Clontech Laboratories, Inc., Mountain View, Calif.). The second copy of FKBP12 was inserted via the AcsI site using T4 DNA ligase.

Cell Culture and Transfection

CHO cells were cultured in Dulbecco's modified Eagle's medium (DMEM, GIBCO, Life Technologies, Thermo Fisher Scientific, Inc., Grand Island, N.Y.) with 10% Fetal Bovine Serum (FBS, Atlanta Biologicals, Inc., Flowery Branch, Ga.), 1xglutamate (GIBCO, Life Technologies, Thermo Fisher Scientific, Inc., Grand Island, N.Y.) and 1x penicillin/streptomycin (GIBCO, Life Technologies, Thermo Fisher Scientific, Inc., Grand Island, N.Y.).

Cells were plated with the starting concentration of 50,000 cells per well in a 24-well plate (Greiner Bio-One North America, Inc., Monroe, N.C.) the day before transfection. 0.2 µg of each DNA construct was mixed with Opti-MEM (GIBCO, Life Technologies, Thermo Fisher Scientific, Inc., Grand Island, N.Y.) and poly(ethylenimine). After incubation at room temperature for 15 minutes, the mixture was added to the cells and cultured for 24 hours.

Then tacrolimus, FK1012-DT, or FK1012-ZE dissolved in DMSO was added into the cell culture with the final concentration of 200 nM, 100 nM, or 100 nM, respectively. Each experiment, including the one with transfected DNA but without drugs, was carried out as triplets. After an incubation of 10 hours, the cells were harvested and washed by PBS buffer (GIBCO, Life Technologies, Thermo Fisher Scientific, Inc., Grand Island, N.Y.) three times.

Luciferase Assay

Cells in 24-well plates were lysed with 100 µL of 1x Passive Lysis Buffer (Promega Corporation, Madison, Wis.) at room temperature for 10 minutes on a shaker. Cell lysates were then collected and centrifuged in tubes and 10 µL of supernatant was added separately into a 96 well plate. 90 µL of Luciferase substrate solution (5 mg of D-luciferin and 7 mg of coenzyme A in 33mL of Luciferase reading buffer, which includes 20 mM tricine, 1.07 mM (MgCO$_3$)$_4$Mg(OH)$_2$.5H$_2$O, 2.67 mM MgSO$_4$, 0.1 mM EDTA, 33.3 mM dithiothreitol and 0.53 mM ATP in water) was added into each well with cell lysates. The signal was read with a 3 s delay and 1 s integration with GLOMAX multi-detection system (Promega Corp., Madison, Wis.). Obtained data were analyzed by KALEIDAGRAPH (Synergy Software, Reading, Pa.).

The results shown in FIG. 13(b) are from three experimental repeats.

The term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one, and the recitations of numerical ranges by endpoints include all numbers subsumed within that range (e.g., 1 to 5 includes 1, 1.5, 2, 2.75, 3, 3.80, 4, 5, etc.).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description has been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

| Sequence Listing Free Text |
|---|
| SEQ ID NO: 1 |
| guugaaucuc augg |
| SEQ ID NO: 2 |
| uuugccucca acug |
| SEQ ID NO: 3 |
| gauuuugaaa aggu |
| SEQ ID NO: 4 |
| ugauaugugc aucu |
| SEQ ID NO: 5 |
| cacacccacc acug |
| SEQ ID NO: 6 |
| accugaugcu cacg |
| SEQ ID NO: 7 |
| aagauucuaa aauu |
| SEQ ID NO: 8 |
| agggaagcga gucu |
| SEQ ID NO: 9 |
| guguucuaua uaaa |
| SEQ ID NO: 10 |
| uucugguggu accc |
| SEQ ID NO: 11 |
| aggacuccca aauu |
| SEQ ID NO: 12 |
| ugugacacuu caaa |
| SEQ ID NO: 13 |
| uguucguuag gcaa |
| SEQ ID NO: 14 |
| guggcaugga guuc |
| SEQ ID NO: 15 |
| gugcaggucc caau |
| SEQ ID NO: 16 |
| gagcaauagu aagg |
| SEQ ID NO: 17 |
| ugguguggag ucuu |
| SEQ ID NO: 18 |
| cucauaccca acca |
| SEQ ID NO: 19 |
| uggauuacuu ugcu |
| SEQ ID NO: 20 |
| uuucccagcu ugac |

What is claimed is:

1. A modular RNA regulator molecule comprising:
   a recognition module comprising a chemical moiety that recognizes at least a portion of a preselected pre-RNA, but does not inhibit nuclease processing of the preselected pre-RNA;
   an inhibition module comprising a moiety that inhibits nuclease processing of the preselected pre-RNA to a mature RNA; and
   a linker module linking the recognition module and the inhibition module, the linking module comprising non-nucleotide small molecule moiety.

2. The modular RNA regulator molecule of claim 1 wherein the recognition module comprises a morpholino, a locked nucleic acid (LNA), a peptide nucleic acid (PNA), a phosphorothioate (S-oligo), or a synthetic/natural molecule that specifically recognizes the preselected pre-mRNA.

3. The modular RNA regulator molecule of claim 1 wherein at least a portion of the recognition module forms a duplex with at least a portion of the preselected pre-RNA.

4. The modular RNA regulator molecule of claim 1 wherein the recognition module comprises a morpholino having no more than 14 nucleotides.

5. The modular RNA regulator molecule of claim 1 wherein the inhibition module comprises a moiety that directly inhibits the enzymatic activity of the nuclease.

6. The modular RNA regulator molecule of claim 1 wherein the nuclease comprises Dicer.

7. The modular RNA regulator molecule of claim 1 wherein the inhibition module comprises a moiety that indirectly interferes with the nuclease.

8. The modular RNA regulator molecule of claim 7 wherein the inhibition module comprises a ligand that selectively binds to a compound that directly interferes with the nuclease.

9. The modular RNA regulator molecule of claim 8 wherein the ligand comprises a synthetic ligand of FKBP (SLF), tacrolimus, a molecule that binds FKBP12 selectively, or a ligand that can selectively recruit an endogenous protein.

10. The modular RNA regulator molecule of claim 9 wherein the endogenous protein comprises FKBP12.

11. The modular RNA regulator molecule of claim 1 wherein the linker module is light-cleavable.

12. The modular RNA regulator molecule of claim 1 further comprising an accessory module.

13. The modular RNA regulator molecule of claim 1 wherein the preselected pre-RNA comprises a pre-miRNA.

14. The modular RNA regulator molecule of claim 6, wherein the inhibition module comprises a moiety comprising three atoms configured to coordinate $Mg^{2+}$ ions in the Dicer active site.

15. The modular RNA regulator molecule of claim 13 wherein the inhibition module comprises an N-hydroxyphthalimide moiety.

* * * * *

UNITED STATES PATENT AND TRADEMARK OFFICE
CERTIFICATE OF CORRECTION

PATENT NO. : 10,093,929 B2
APPLICATION NO. : 15/029307
DATED : October 9, 2018
INVENTOR(S) : Fu-Sen Liang Page 1 of 1

It is certified that error appears in the above-identified patent and that said Letters Patent is hereby corrected as shown below:

In the Claims

Column 34, Line 62, Claim 14, --$Mg^{2+}$ ions-- should read --$Mg^{2+}$ ions--.

Column 34, Line 64, Claim 15, --molecule of claim 13-- should read --molecule of claim 14--.

Signed and Sealed this
Fourth Day of June, 2019

Andrei Iancu
*Director of the United States Patent and Trademark Office*

```
                           SEQUENCE LISTING

<160> NUMBER OF SEQ ID NOS: 20

<210> SEQ ID NO 1
<211> LENGTH: 14
<212> TYPE: RNA
<213> ORGANISM: artificial
<220> FEATURE:
<223> OTHER INFORMATION: RNA sequence for targeting pre-miRNA

<400> SEQUENCE: 1
guugaaucuc augg                                                    14

<210> SEQ ID NO 2
<211> LENGTH: 14
<212> TYPE: RNA
<213> ORGANISM: artificial
<220> FEATURE:
<223> OTHER INFORMATION: RNA sequence for targeting pre-miRNA

<400> SEQUENCE: 2
uuugccucca acug                                                    14

<210> SEQ ID NO 3
<211> LENGTH: 14
<212> TYPE: RNA
<213> ORGANISM: artificial
<220> FEATURE:
<223> OTHER INFORMATION: RNA sequence for targeting pre-miRNA

<400> SEQUENCE: 3
gauuuugaaa aggu                                                    14

<210> SEQ ID NO 4
```

-continued

```
<211> LENGTH: 14
<212> TYPE: RNA
<213> ORGANISM: artificial
<220> FEATURE:
<223> OTHER INFORMATION: RNA sequence for targeting pre-miRNA

<400> SEQUENCE: 4
ugauaugugc aucu                                                       14

<210> SEQ ID NO 5
<211> LENGTH: 14
<212> TYPE: RNA
<213> ORGANISM: artificial
<220> FEATURE:
<223> OTHER INFORMATION: RNA sequence for targeting pre-miRNA

<400> SEQUENCE: 5
cacacccacc acug                                                       14

<210> SEQ ID NO 6
<211> LENGTH: 14
<212> TYPE: RNA
<213> ORGANISM: artificial
<220> FEATURE:
<223> OTHER INFORMATION: RNA sequence for targeting pre-miRNA

<400> SEQUENCE: 6
accugaugcu cacg                                                       14

<210> SEQ ID NO 7
<211> LENGTH: 14
<212> TYPE: RNA
<213> ORGANISM: artificial
<220> FEATURE:
<223> OTHER INFORMATION: RNA sequence for targeting pre-miRNA

<400> SEQUENCE: 7
aagauucuaa aauu                                                       14

<210> SEQ ID NO 8
<211> LENGTH: 14
<212> TYPE: RNA
<213> ORGANISM: artificial
<220> FEATURE:
<223> OTHER INFORMATION: RNA sequence for targeting pre-miRNA

<400> SEQUENCE: 8
agggaagcga gucu                                                       14

<210> SEQ ID NO 9
<211> LENGTH: 14
<212> TYPE: RNA
<213> ORGANISM: artificial
<220> FEATURE:
<223> OTHER INFORMATION: RNA sequence for targeting pre-miRNA

<400> SEQUENCE: 9
guguucuaua uaaa                                                       14

<210> SEQ ID NO 10
<211> LENGTH: 14
<212> TYPE: RNA
<213> ORGANISM: artificial
<220> FEATURE:
<223> OTHER INFORMATION: RNA sequence for targeting pre-miRNA

<400> SEQUENCE: 10
``` uucuggugguaccc          14

<210> SEQ ID NO 11
<211> LENGTH: 14
<212> TYPE: RNA
<213> ORGANISM: artificial
<220> FEATURE:
<223> OTHER INFORMATION: RNA sequence for targeting pre-miRNA

<400> SEQUENCE: 11 aggacucccaaauu          14

<210> SEQ ID NO 12
<211> LENGTH: 14
<212> TYPE: RNA
<213> ORGANISM: artificial
<220> FEATURE:
<223> OTHER INFORMATION: RNA sequence for targeting pre-miRNA

<400> SEQUENCE: 12 ugugacacuucaaa          14

<210> SEQ ID NO 13
<211> LENGTH: 14
<212> TYPE: RNA
<213> ORGANISM: artificial
<220> FEATURE:
<223> OTHER INFORMATION: RNA sequence for targeting pre-miRNA

<400> SEQUENCE: 13 uguucguuaggcaa          14

<210> SEQ ID NO 14
<211> LENGTH: 14
<212> TYPE: RNA
<213> ORGANISM: artificial
<220> FEATURE:
<223> OTHER INFORMATION: RNA sequence for targeting pre-miRNA

<400> SEQUENCE: 14 guggcauggaguuc          14

<210> SEQ ID NO 15
<211> LENGTH: 14
<212> TYPE: RNA
<213> ORGANISM: artificial
<220> FEATURE:
<223> OTHER INFORMATION: RNA sequence for targeting pre-miRNA

<400> SEQUENCE: 15 gugcaggucccaau          14

<210> SEQ ID NO 16
<211> LENGTH: 14
<212> TYPE: RNA
<213> ORGANISM: artificial
<220> FEATURE:
<223> OTHER INFORMATION: RNA sequence for targeting pre-miRNA

<400> SEQUENCE: 16 gagcaauaguaagg          14

<210> SEQ ID NO 17
<211> LENGTH: 14
<212> TYPE: RNA

```
<213> ORGANISM: artificial
<220> FEATURE:
<223> OTHER INFORMATION: RNA sequence for targeting pre-miRNA

<400> SEQUENCE: 17
ugguguggag ucuu                                                    14

<210> SEQ ID NO 18
<211> LENGTH: 14
<212> TYPE: RNA
<213> ORGANISM: artificial
<220> FEATURE:
<223> OTHER INFORMATION: RNA sequence for targeting pre-miRNA

<400> SEQUENCE: 18
cucauaccca acca                                                    14

<210> SEQ ID NO 19
<211> LENGTH: 14
<212> TYPE: RNA
<213> ORGANISM: artificial
<220> FEATURE:
<223> OTHER INFORMATION: RNA sequence for targeting pre-miRNA

<400> SEQUENCE: 19
uggauuacuu ugcu                                                    14

<210> SEQ ID NO 20
<211> LENGTH: 14
<212> TYPE: RNA
<213> ORGANISM: artificial
<220> FEATURE:
<223> OTHER INFORMATION: RNA sequence for targeting pre-miRNA

<400> SEQUENCE: 20
uuucccagcu ugac                                                    14
```